US011938295B2

(12) United States Patent
Shimizu et al.

(10) Patent No.: US 11,938,295 B2
(45) Date of Patent: *Mar. 26, 2024

(54) INGESTIBLE DEVICE FOR DELIVERY OF THERAPEUTIC AGENT TO THE GASTROINTESTINAL TRACT

(71) Applicant: Biora Therapeutics, Inc., San Diego, CA (US)

(72) Inventors: Jeffrey A. Shimizu, Poway, CA (US); Mitchell Lawrence Jones, La Jolla, CA (US); Mark Sasha Drlik, Victoria (CA); Iman Niknia, Victoria (CA); Nathan John Muller, Victoria (CA); Tuyen Nguyen, Victoria (CA); Christopher Loren Wahl, San Diego, CA (US); Edward Mudge, Cambridgeshire (GB); Nicholas Mark Salt, Cambridgeshire (GB); Nia Eleri Stevens, Cambridgeshire (GB); Stuart Robert Abercrombie, Cambridgeshire (GB); Christopher Ian Bunce, Cambridgeshire (GB); Ryan Elliott Jones, Turks and Caicos Island (CA); Kevin Howe, London (GB); Pejman Rahimian, Colleyville, TX (US); Nelson Quintana, Temecula, CA (US)

(73) Assignee: Biora Therapeutics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/945,890

(22) Filed: Sep. 15, 2022

(65) Prior Publication Data

US 2023/0017603 A1 Jan. 19, 2023

Related U.S. Application Data

(63) Continuation of application No. 17/784,453, filed as application No. PCT/US2020/064590 on Dec. 11, 2020, now Pat. No. 11,707,610.

(60) Provisional application No. 63/086,630, filed on Oct. 2, 2020, provisional application No. 63/027,427, filed on May 20, 2020, provisional application No. 62/948,082, filed on Dec. 13, 2019.

(51) Int. Cl.
*A61J 3/07* (2006.01)
*A61K 9/48* (2006.01)
*A61M 31/00* (2006.01)
*A61M 37/00* (2006.01)

(52) U.S. Cl.
CPC ......... *A61M 31/002* (2013.01); *A61K 9/4808* (2013.01); *A61M 37/0015* (2013.01); *A61M 2037/0061* (2013.01); *A61M 2210/1042* (2013.01)

(58) Field of Classification Search
None
See application file for complete search history.

(56) References Cited

U.S. PATENT DOCUMENTS

| | | |
|---|---|---|
| 3,057,344 A | 10/1962 | Alberto |
| 3,118,439 A | 1/1964 | Barana |
| 3,315,660 A | 4/1967 | Abella |
| 3,485,235 A | 12/1969 | Felson |
| 4,036,214 A | 7/1977 | Bucalo |
| 4,172,446 A | 10/1979 | Bucalo |
| 4,239,040 A | 12/1980 | Hosoya |
| 4,425,117 A | 1/1984 | Hugeman |
| 4,481,952 A | 11/1984 | Pawelec |
| 4,507,115 A | 3/1985 | Kambara |
| 4,522,625 A | 6/1985 | Edgren |
| 5,167,626 A | 12/1992 | Casper et al. |
| 5,170,801 A | 12/1992 | Casper |
| 5,217,449 A | 6/1993 | Yuda Shunichi et al. |
| 5,279,607 A | 1/1994 | Schentag |
| 5,316,015 A | 5/1994 | Sinaiko |
| 5,318,557 A | 6/1994 | Gross |
| 5,395,366 A | 3/1995 | D'Andrea et al. |
| 5,604,531 A | 2/1997 | Iddan et al. |
| 5,738,110 A | 4/1998 | Beal et al. |
| 5,858,001 A | 1/1999 | Tsals et al. |
| 5,951,538 A | 9/1999 | Joshi |
| 5,971,942 A | 10/1999 | Gu et al. |
| 6,632,216 B2 | 10/2003 | Houzego |
| 6,884,239 B2 | 4/2005 | Houzego et al. |

(Continued)

FOREIGN PATENT DOCUMENTS

| | | |
|---|---|---|
| CN | 1856290 B | 11/2006 |
| CN | 108784634 A | 11/2018 |

(Continued)

OTHER PUBLICATIONS

International Search Report and Written Opinion for PCT/US2020/064590, dated Apr. 7, 2021, 15 pages.

(Continued)

*Primary Examiner* — Susan T Tran
(74) *Attorney, Agent, or Firm* — Perkins Coie LLP

(57) ABSTRACT

Ingestible devices can directly deliver therapeutic agents to desired tissue(s) of the GI tract of a subject, such as the submucosa, the mucosa, and/or the mucus layer of the GI tract, and methods of using the same. The ingestible devices can deliver therapeutic agents in a safe, effective, and reliable manner. The disclosure also provides pharmaceutical compositions for use in methods of treating a disease or condition in a subject in need thereof.

20 Claims, 37 Drawing Sheets

(56) References Cited

U.S. PATENT DOCUMENTS

| | | |
|---|---|---|
| 6,950,690 B1 | 9/2005 | Meron et al. |
| 7,144,366 B2 | 12/2006 | Takizawa et al. |
| 7,160,258 B2 | 1/2007 | Imran et al. |
| 7,611,480 B2 | 11/2009 | Levy |
| 7,662,093 B2 | 2/2010 | Gilad et al. |
| 7,717,862 B2 | 5/2010 | Stoltz |
| 7,763,014 B2 | 7/2010 | Houzeao et al. |
| 7,946,979 B2 | 5/2011 | Gilad et al. |
| 8,005,536 B2 | 8/2011 | Imran |
| 8,216,130 B2 | 6/2012 | Glukhovsky et al. |
| 8,360,976 B2 | 1/2013 | Imran |
| 8,597,279 B2 | 12/2013 | Dijksman et al. |
| 8,626,268 B2 | 1/2014 | Adler |
| 8,696,602 B2 | 4/2014 | Semler et al. |
| 8,740,774 B2 | 6/2014 | Takizawa et al. |
| 8,809,271 B2 | 8/2014 | Imran |
| 8,926,526 B2 | 1/2015 | Shuck |
| 9,072,834 B2 | 7/2015 | Vogt |
| 9,456,737 B2 | 10/2016 | Pascal |
| 9,511,121 B2 | 12/2016 | Imran |
| 10,172,598 B2 | 1/2019 | Amoako-Tuffour et al. |
| 10,588,608 B2 | 3/2020 | Jones et al. |
| 10,632,251 B2 | 4/2020 | Imran et al. |
| 10,765,360 B2 | 9/2020 | Euliano et al. |
| 10,835,152 B2 | 11/2020 | Jones et al. |
| 11,007,356 B2 | 5/2021 | Shimizu et al. |
| 11,439,802 B2 | 9/2022 | Shimizu et al. |
| 2002/0198470 A1 | 12/2002 | Imran et al. |
| 2004/0162469 A1 | 8/2004 | Imran |
| 2004/0199054 A1 | 10/2004 | Wakefield et al. |
| 2004/0253304 A1 | 12/2004 | Gross et al. |
| 2005/0158246 A1 | 7/2005 | Takizawa |
| 2007/0043320 A1 | 2/2007 | Kenany |
| 2008/0051635 A1 | 2/2008 | Tanaka et al. |
| 2009/0275923 A1 | 11/2009 | Shimizu et al. |
| 2010/0063486 A1 | 3/2010 | Dilksman et al. |
| 2010/0324381 A1 | 12/2010 | Glukhovsky et al. |
| 2011/0046458 A1 | 2/2011 | Pinedo |
| 2011/0092959 A1 | 4/2011 | Zou et al. |
| 2011/0106063 A1 | 5/2011 | Diiksman et al. |
| 2012/0136209 A1 | 5/2012 | Kostenich et al. |
| 2015/0011874 A1 | 1/2015 | Amoaka-Tuffour et al. |
| 2015/0051589 A1 | 2/2015 | Sako et al. |
| 2015/0065926 A1 | 3/2015 | Nakamura et al. |
| 2016/0213234 A1 | 7/2016 | Poon |
| 2016/0235663 A1 | 8/2016 | Zou et al. |
| 2016/0375232 A1 | 12/2016 | Kugler et al. |
| 2017/0050006 A1 | 2/2017 | Imran et al. |
| 2017/0106099 A1 | 4/2017 | Bellinger et al. |
| 2017/0296092 A1 | 10/2017 | Jones et al. |
| 2018/0049725 A1 | 2/2018 | Jones et al. |
| 2018/0052084 A1 | 2/2018 | Jones et al. |
| 2018/0070857 A1 | 3/2018 | Jones et al. |
| 2018/0160950 A1 | 6/2018 | Rabinovitz et al. |
| 2018/0279908 A1 | 10/2018 | Jones et al. |
| 2018/0318496 A1 | 11/2018 | Zou et al. |
| 2019/0083073 A1 | 3/2019 | Amoaka-Tuffour et al. |
| 2020/0094031 A1 | 3/2020 | Jones et al. |
| 2020/0245897 A1 | 8/2020 | Jones et al. |
| 2020/0038268 A1 | 10/2020 | Imran |
| 2020/0316352 A1 | 10/2020 | Aran et al. |
| 2021/0015398 A1 | 1/2021 | Jones et al. |
| 2021/0038872 A1* | 2/2021 | Shimizu ............... C07K 16/241 |
| 2021/0093248 A1 | 4/2021 | Euliano et al. |
| 2021/0161805 A1 | 6/2021 | Zou et al. |
| 2021/0283385 A1* | 9/2021 | Shimizu ............... C07K 16/241 |
| 2022/0072286 A1 | 3/2022 | Bonner et al. |

FOREIGN PATENT DOCUMENTS

| | | |
|---|---|---|
| DE | 19801573 A1 | 7/1999 |
| EP | 1530950 A1 | 5/2005 |
| EP | 2201938 A1 | 6/2010 |
| EP | 2515992 B1 | 10/2012 |
| JP | 2005073888 A | 3/2005 |
| WO | WO2008014439 A2 | 1/2008 |
| WO | WO2009104110 A1 | 8/2009 |
| WO | WO2011018753 A1 | 2/2011 |
| WO | WO2013003824 A1 | 1/2013 |
| WO | 2018049133 A1 | 3/2018 |
| WO | WO2018049133 A1 | 3/2018 |
| WO | WO2018183934 A1 | 10/2018 |
| WO | WO2018213588 A1 | 11/2018 |
| WO | WO2020041774 A1 | 2/2020 |
| WO | WO2020157324 A1 | 8/2020 |
| WO | WO2020160399 A1 | 8/2020 |
| WO | 2021119482 A1 | 6/2021 |

OTHER PUBLICATIONS

Examination Report for European Application No. 20834101.6; dated Nov. 28, 2022; 4 pages.

* cited by examiner

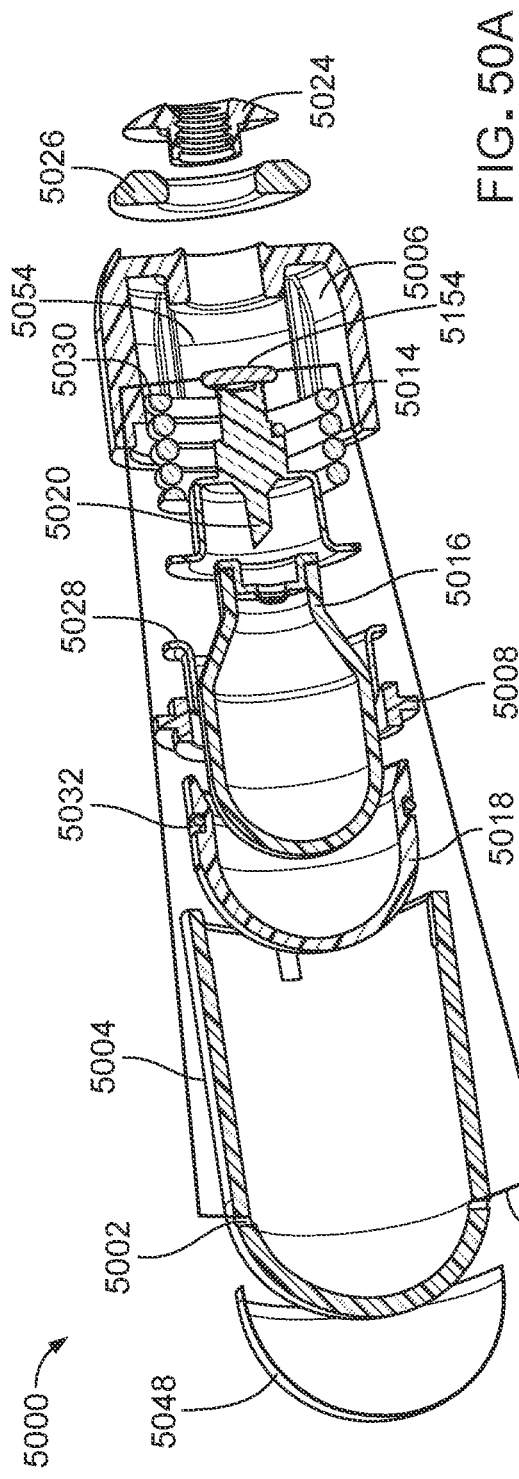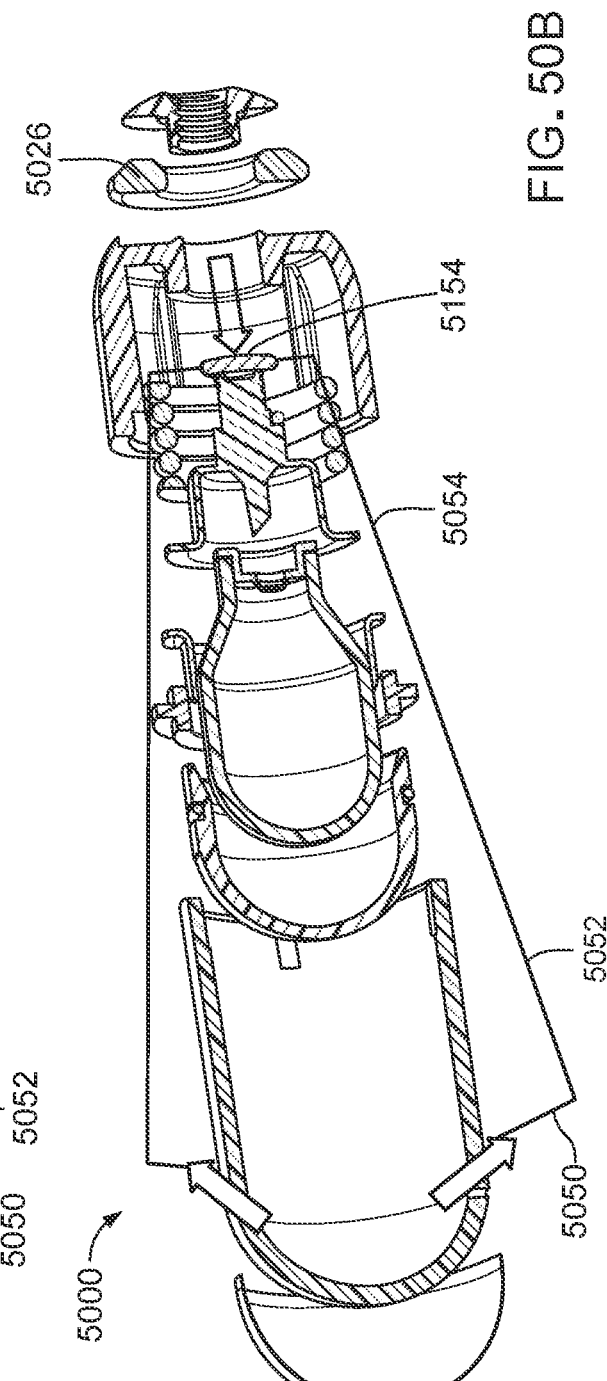

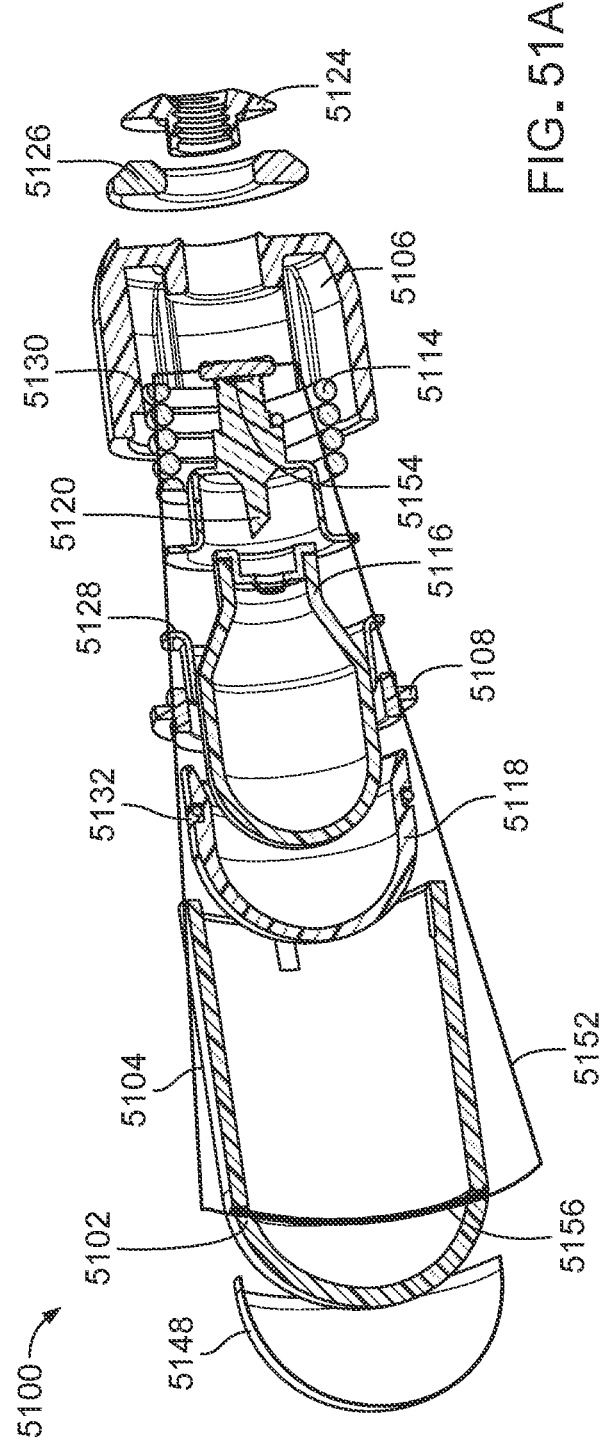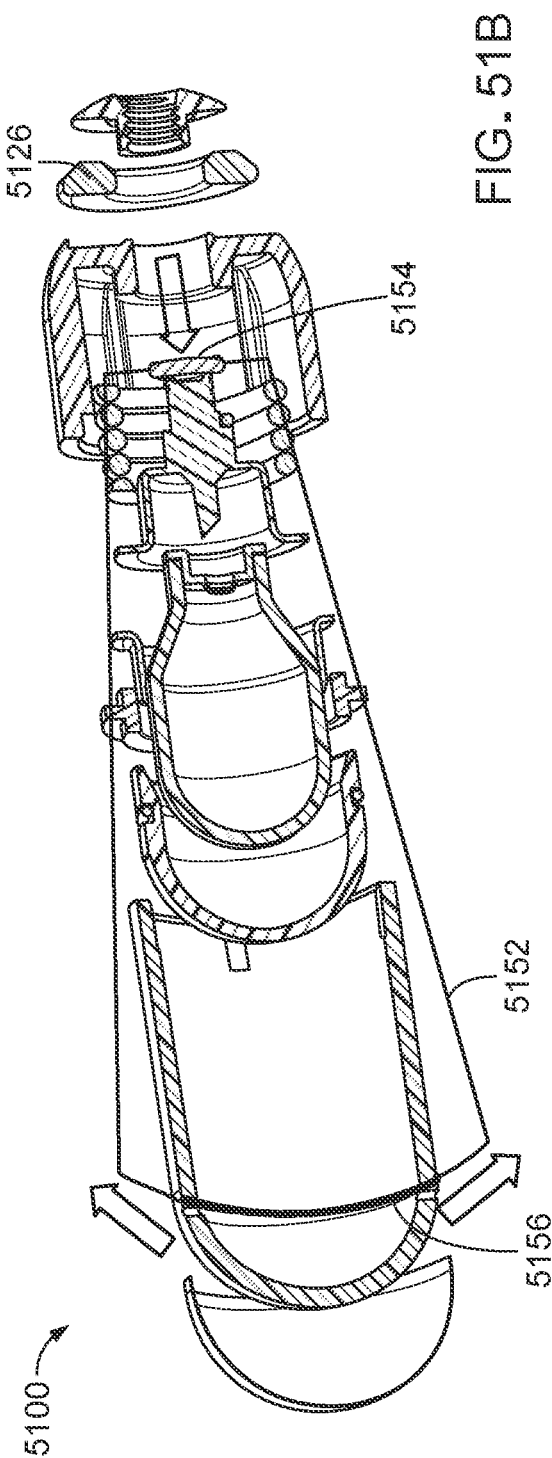

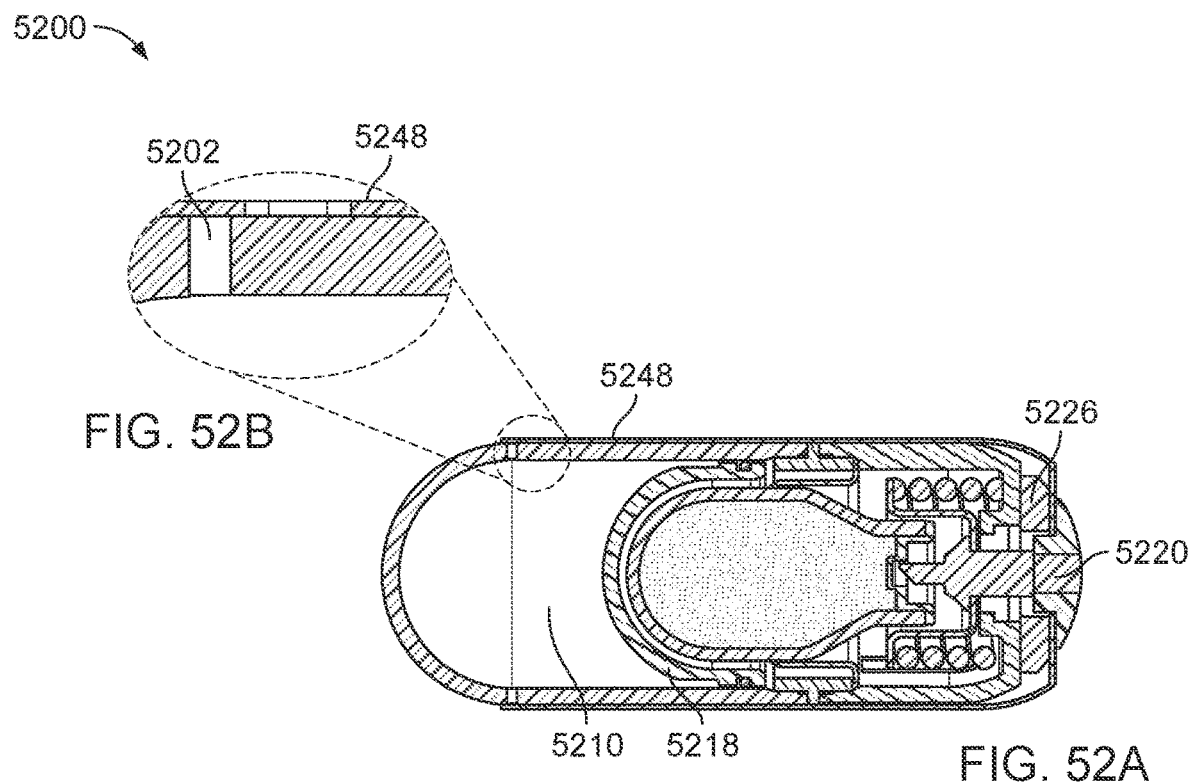
FIG. 52B
FIG. 52A
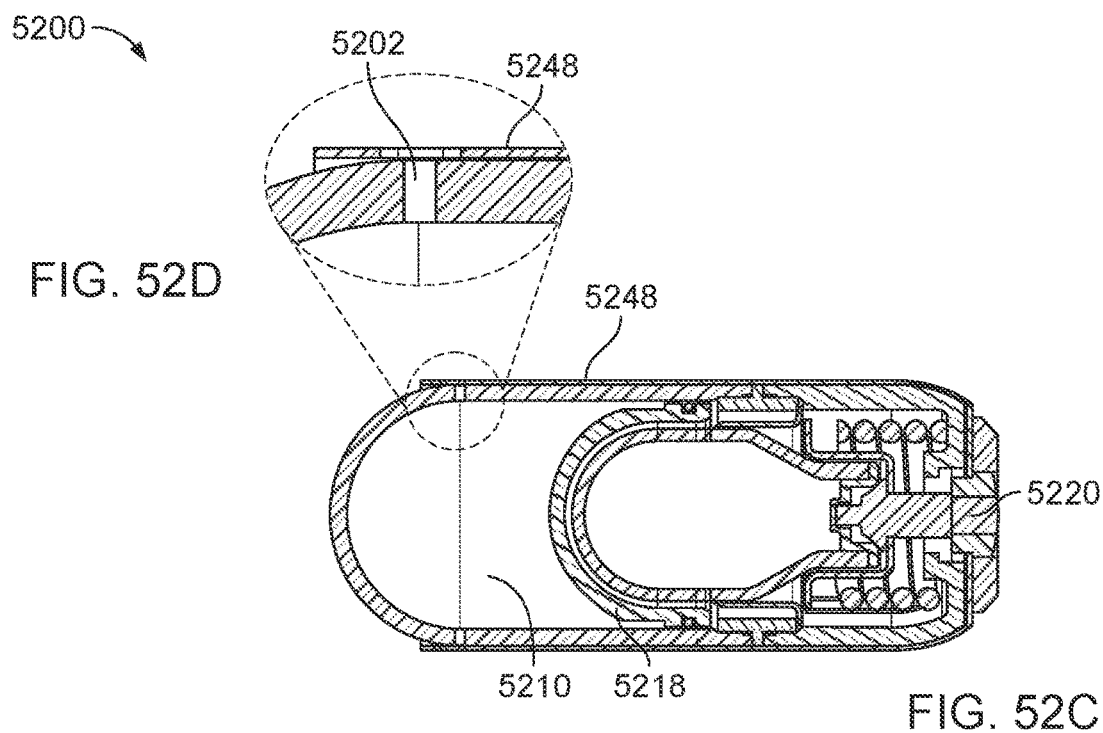
FIG. 52D
FIG. 52C

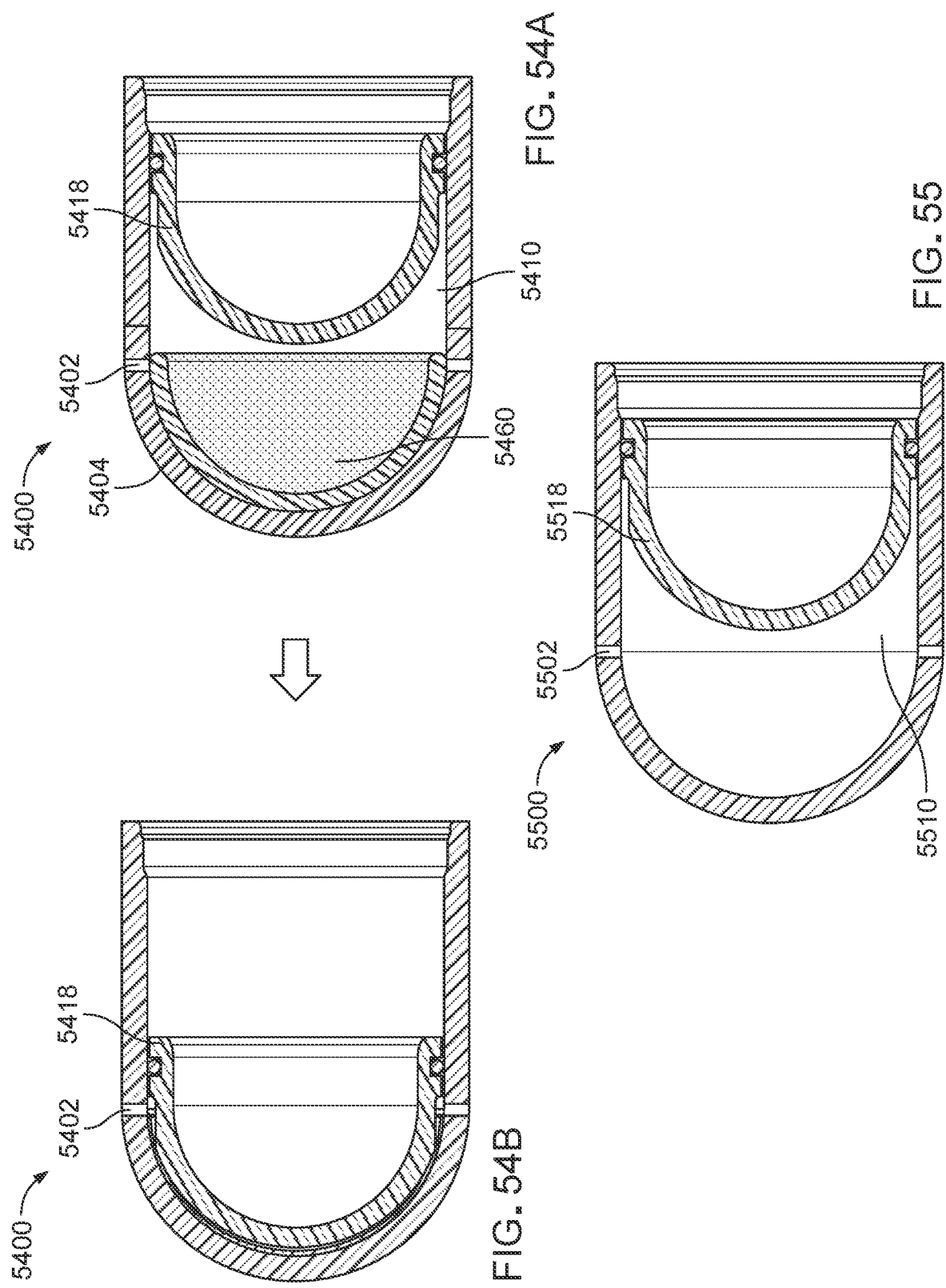

INGESTIBLE DEVICE FOR DELIVERY OF THERAPEUTIC AGENT TO THE GASTROINTESTINAL TRACT

CROSS-REFERENCE TO RELATED APPLICATIONS

This application is a continuation of U.S. application Ser. No. 17/784,453 filed Jun. 10, 2022, now U.S. Pat. No. 11,707,610 B2, which is a § 371 of International Application No. PCT/US2020/064590, which claims priority to U.S. Application No. 62/948,082, filed Dec. 13, 2019, U.S. Application No. 63/027,427, filed May 20, 2020, and U.S. Application No. 63/086,630, filed Oct. 2, 2020, The entire disclosure of each of these applications is incorporated by reference herein.

TECHNICAL FIELD

The disclosure generally relates to ingestible devices capable of delivering a dispensable substance, such as a therapeutic agent, as well as related components, systems and methods.

BACKGROUND

The gastrointestinal (GI) tract generally provides a therapeutic medium for an individual's body. At times, it is desirable to dispense therapeutic agents to the GI tract to treat a medical condition.

SUMMARY

The disclosure provides ingestible devices that can directly deliver therapeutic agents to desired tissue(s) of the GI tract of a subject, such as the submucosa, the mucosa, and/or the mucus layer of the GI tract, and methods of using the same. The ingestible devices can deliver therapeutic agents in a safe, effective, and reliable manner. The disclosure also provides pharmaceutical compositions for use in methods of treating a disease or condition in a subject in need thereof.

TECHNICAL FIELD

The disclosure generally relates to ingestible devices capable of delivering a dispensable substance, such as a therapeutic agent, as well as related components, systems and methods.

BACKGROUND

The gastrointestinal (GI) tract generally provides a therapeutic medium for an individual's body. At times, it is desirable to dispense therapeutic agents to the GI tract to treat a medical condition.

SUMMARY

The disclosure provides ingestible devices that can directly deliver therapeutic agents to desired tissue(s) of the GI tract of a subject, such as the submucosa, the mucosa, and/or the mucus layer of the GI tract, and methods of using the same. The ingestible devices can deliver therapeutic agents in a safe, effective, and reliable manner. The disclosure also provides pharmaceutical compositions for use in methods of treating a disease or condition in a subject in need thereof.

Ingestible devices of the present disclosure are configured to provide at least three different modes of direct delivery of therapeutic agents to the GI tract of a subject, referred to herein as trans-epithelial, epithelial, and topical delivery. Direct delivery, as used herein, refers to a force-driven delivery mechanism.

Thus, in one aspect, this disclosure relates to trans-epithelial delivery of a therapeutic agent to the GI tract of a subject. Accordingly, the disclosure provides an ingestible device that can directly deliver a therapeutic agent past the epithelial cell layer of the mucosa of the GI tract of a subject to yield systemic exposure of the therapeutic agent to the subject. In such embodiments, the ingestible device is configured to directly deliver the therapeutic agent past the epithelial cell layer of the mucosa and into the submucosa and/or into a region of the mucosa beneath the epithelial layer (e.g., into the lamina propria) of the GI tract, where it is available for systemic uptake. This can be particularly relevant when the oral bioavailability of the therapeutic agent is otherwise low. In some embodiments, systemic exposure of the therapeutic agent is achieved by trans-epithelial delivery of the therapeutic agent into the submucosa and/or into a region of the mucosa beneath the epithelial layer (e.g., into the lamina propria) of the small intestine, for example, in the duodenum, the jejunum, and/or the ileum. In further embodiments, the trans-epithelial delivery directly delivers the therapeutic agent into the submucosa submucosa and/or into a region of the mucosa beneath the epithelial layer (e.g., into the lamina propria) of the GI tract such that the percent systemic uptake of the trans-epithelial delivery relative to intravenous or subcutaneous administration is at least about 10% (e.g., at least about 15%, at least about 20%, at least about 25% or more).

Without wishing to be bound by theory, it is believed that trans-epithelial delivery to the submucosa and/or into a region of the mucosa beneath the epithelial layer (e.g., into the lamina propria) of the GI tract is achieved by using an appropriate value for one or more performance parameters associated with the ingestible device configured for such use. Such performance parameters include, for example, internal pressure of the ingestible device, peak fluid pressure of the ingestible device, nozzle pressure of the ingestible device, peak jet power of the dispensable substance (e.g., a pharmaceutical formulation containing the therapeutic agent) delivered from the ingestible device, peak jet velocity of the dispensable substance (e.g., a pharmaceutical formulation containing the therapeutic agent) delivered from the ingestible device, peak jet pressure of the dispensable substance (e.g., a pharmaceutical formulation containing the therapeutic agent) delivered from the ingestible device, peak jet force of the dispensable substance (e.g., a pharmaceutical formulation containing the therapeutic agent) delivered from the ingestible device, peak jet stable length of the dispensable substance (e.g., a pharmaceutical formulation containing the therapeutic agent) delivered from the ingestible device, nozzle shape, nozzle length and nozzle diameter.

In another aspect, this disclosure relates to epithelial delivery of a therapeutic agent to the GI tract of a subject. Accordingly, the disclosure provides an ingestible device configured to directly deliver the therapeutic agent into the mucus and/or onto the epithelial layer, but not past the epithelial layer of the mucosa, of the small or large intestine, from which it can act locally, and in some cases away from the site of direct delivery. In some embodiments, the device is configured so that the therapeutic agent is delivered from the device with sufficient force to provide the epithelial delivery, the force being lower than that required for trans-epithelial delivery.

In yet another aspect, this disclosure relates to topical delivery of a therapeutic agent to the GI tract of a subject. Accordingly, the disclosure provides an ingestible device configured to deliver the therapeutic agent into the lumen and/or onto the mucus or other surface of the GI tract facing the lumen of the small or large intestine, from which it can act locally, and in some cases away from the site of delivery. In some embodiments, the device is configured so that the therapeutic agent is delivered from the device with sufficient force so that the therapeutic agent is delivered topically, the force being lower than that required for the epithelial or the trans-epithelial delivery.

The ingestible device, whether configured for trans-epithelial, epithelial or topical delivery, can have a streamlined and/or relatively simple mechanical design, be relatively small, and/or be inexpensive to manufacture. In general, the device protects a dispensable substance (e.g., a therapeutic agent, or a pharmaceutical formulation comprising the therapeutic agent) until the device reaches a desired location of the subject. As an example, the device can be designed to deliver dispensable substance to a desired location in the GI tract of a subject, and the device can be designed so that the dispensable substance is not subject to constituents of the GI tract (e.g., acids, enzymes) prior to reaching the desired location in the GI tract. As another example, the device can be designed to deliver dispensable substance such that the therapeutic properties of the dispensable substance are not altered during delivery (e.g., the dispensable substance is a therapeutic agent that binds its therapeutic target after delivery).

The present disclosure provides ingestible devices that can directly deliver therapeutic agents to desired tissue(s) of the GI tract of a subject (such as the submucosa, the mucosa, and/or the mucus layer of the GI tract), e.g., to treat a particular class of disease, or a specific disease. Relatedly, methods of using the device to deliver the therapeutic agents to desired tissue(s) of the GI tract, e.g., to treat a particular class of disease, or a specific disease, are disclosed. These disclosures also inherently provide disclosures of corresponding medical uses—that is, disclosures of the recited therapeutic agents for use in a method of treating the recited class of disease, or specific disease, by using the device to deliver the recited agents to desired tissue(s) of the GI tract of a subject.

In an aspect, the disclosure provides an ingestible device that includes: a housing comprising an interior and an opening; a gas cylinder in the interior of the housing, the gas cylinder having a breakable seal; a spring in the interior of the housing; a piston in the interior of the housing; a piercer in the interior of the housing; a retainer; and a trigger exposed to an environment external to the housing. In a first state of the ingestible device: the trigger holds the retainer in a first position; the retainer holds the piercer in a first position in which the piercer does not break the breakable seal of the gas cylinder; and the interior of the ingestible device is configured to contain a dispensable substance without the dispensable substance being delivered from the ingestible device via the opening in the housing.

In some embodiments, in a second state of the ingestible device: the trigger is at least partially dissolved, degraded and/or eroded so that the trigger is unable to hold the retainer in its first position; and the retainer is unable to hold piercer in its first position.

In some embodiments, in the second state of the ingestible device: the spring applies a force to the piercer to move the piercer so that the piercer breaks the breakable seal of the gas cylinder; a gas is released from the gas cylinder; the gas applies a force to the piston so that the piston applies a force to the dispensable substance; and the dispensable substance is delivered out of the ingestible device via the opening in the housing.

The ingestible device can further include a seal between the piston and the housing, and/or a seal between the piercer and the housing.

In an aspect, the disclosure provides an ingestible device that includes: a housing configured to contain a dispensable substance comprising a therapeutic agent in an interior of the housing; a gas cylinder in the interior of the housing; a spring in the interior of the housing; a piston in the interior of the housing; a seal between the piston and the housing; a piercer in the interior of the housing; a retainer; and a trigger exposed to an environment external to the housing.

In an aspect, the disclosure provides an ingestible device that includes: a housing configured to contain a dispensable substance comprising a therapeutic agent in an interior of the housing; a gas cylinder in the interior of the housing; a spring in the interior of the housing; a piston in the interior of the housing; a piercer in the interior of the housing; a retainer; a seal between the retainer and the housing; and a trigger exposed to an environment external to the housing.

In an aspect, the disclosure provides an ingestible device that includes: a housing configured to contain a dispensable substance comprising a therapeutic agent in an interior of the housing; a gas cylinder in the interior of the housing; a spring in the interior of the housing; a piston in the interior of the housing; a first seal between the piston and the housing; a piercer in the interior of the housing; a retainer; a second seal between the retainer and the housing; and a trigger exposed to an environment external to the housing.

An ingestible device can be 00 sized device.

The trigger can include an enteric material.

The housing can include first and second housing parts, with the piston and the dispensable substance inside the first housing part, and the spring and the retainer inside the second housing part.

In some embodiments, at least one of the following holds: the ingestible device is configured for trans-epithelial delivery of the dispensable subject to the GI tract of a subject; the ingestible device is configured for epithelial delivery of the dispensable subject to the GI tract of a subject; and the ingestible device is configured for topical delivery of the dispensable subject to the GI tract of a subject.

An ingestible device can further include the dispensable substance. In some embodiments, the dispensable substance is a solution or a suspension.

In some embodiments, at least one of the following holds: the ingestible device is configured to deliver the dispensable substance to tissue of the GI tract of a subject as a jet with a peak jet power of from about one Watt to about three Watts; the ingestible device is configured to deliver the dispensable substance at a peak jet velocity of from about 25 meters per second to about 45 meters per second; the ingestible device is configured to deliver the dispensable substance to tissue of the GI tract of a subject at a peak jet pressure of from about 100 psig to about 250 psig; the ingestible device is configured to deliver the dispensable substance to tissue of the GI tract of a subject at a peak jet force of from about 0.09 N to about 0.15 N; the ingestible device is configured to deliver the dispensable substance as a jet having jet stable length of at least about 0.5 millimeter; the ingestible device is configured to provide an internal pressure of from about 225 psig to about 425 psig; and the ingestible device is configured to contain the dispensable substance at a peak fluid pressure of from about 200 psig to about 400 psig.

In some embodiments, at least one component of an ingestible device includes a cylic olefin polymer. In some embodiments, the breakable seal is scored.

In some embodiments, the breakable seal has a varying thickness.

In some embodiments, the gas cylinder has a burst pressure of from about 2,800 psig to about 4,500 psig.

In some embodiments, the gas cylinder contains at least one gas selected from the group consisting of air, nitrogen, oxygen, carbon dioxide, hydrofluorocarbon gases and noble gases.

In some embodiments, an ingestible device further includes an element having a first state in which the element at least partially covers the opening in the housing and a second state in which the element does not cover the opening in the housing, wherein the ingestible device is configured so that, when the piston moves, the element moves from its first state to its second state. The element can move synchronously with the piston. When the piston moves a distance, the element can move the same distance. The ingestible device can further include a seal mechanically coupled with the piston and element. The seal can be configured to cause the movement of the piston to result in the movement of the element. The element can conform to an inner radius of the housing.

In some embodiments, the ingestible device further includes a covering over the opening in the housing. The covering can be removable from the ingestible device. The covering can be configured to be removed from the housing due to pressure applied by the dispensable substance. The covering can include an enteric material. The covering can be a film, a foil, a band, a plug, or a patch. The covering has a burst pressure of at most 420 psig. In some embodiments, the ingestible device further includes a second piston configured so that, when the first piston applies the force on the dispensable substance, the dispensable substance applies a force on the second piston to slide the second piston to expose the openings and the dispensable substance is forced out of the ingestible device via the openings.

In some embodiments, the ingestible device further includes a removable cap affixed to the ingestible device and configured so that, when the piston moves to apply the force on the dispensable substance, the dispensable substance applies a force on the cap to slide the cap to expose the opening in the housing.

In some embodiments, the ingestible device further includes an inflated membrane volume covering the opening and configured so that, when the piston moves to apply force on the dispensable substance, the dispensable substance applies force on the inflated membrane volume and the inflated membrane volume is compressed to expose the opening in the housing.

In an aspect, the disclosure provides a method that includes using an ingestible device according to the disclosure to deliver a dispensable substance to the GI tract of a subject.

The details of one or more embodiments of the device and methods are set forth in the accompanying drawings and the description below. Other features and advantages will be apparent from the description and drawings, and from the claims.

BRIEF DESCRIPTION OF THE DRAWINGS

FIGS. 42A-47C show aspects of an ingestible device.
FIGS. 50A and 50B show exploded views of an ingestible device.
FIGS. 51A and 51B show exploded views of an ingestible device.
FIGS. 52A-52D show views of an ingestible device.
FIGS. 54a and 54B show views of a portion of an ingestible device.
FIG. 55 shows a view of a portion of an ingestible device.

DETAILED DESCRIPTION

Incorporation by Reference

Figure 1A:
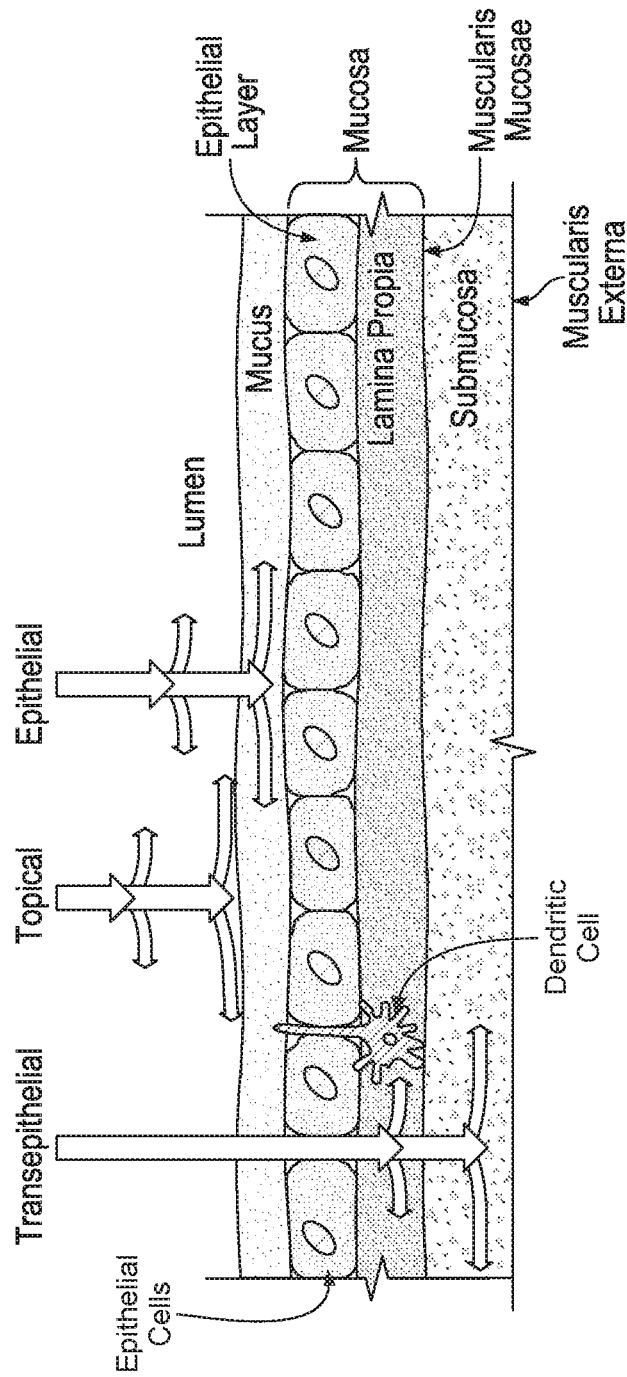
FIG. 1A is a schematic cross section of the different regions of healthy intestinal tissue.

This application incorporates by reference the following patent applications in their entirety: U.S. Ser. No. 62/769,496, filed Nov. 19, 2018, and entitled "Ingestible Device With High Pressure Substance Delivery to the Gastrointestinal Tract"; U.S. Ser. No. 62/818,731, filed Mar. 14, 2019, and entitled "Ingestible Device With High Pressure Substance Delivery to the Gastrointestinal Tract"; U.S. Ser. No. 62/819,513, filed Mar. 15, 2019, and entitled "Ingestible Device With High Pressure Substance Delivery to the Gastrointestinal Tract"; and U.S. Ser. No. 62/932,459, filed Nov. 7, 2019, and entitled "Ingestible Device and Method of Use to Deliver Therapeutic Agent to the Gastrointestinal Tract."

Definitions

"Ingestible," as used herein in reference to the device, means that the device can be swallowed whole.

"Dispensable" as used herein with reference to any substance, refers to any substance that may be released from an ingestible device as disclosed herein, or from a component of the device such as a reservoir.

As used herein, the term "enteric" refers a material that permits transition to a desired location in the GI tract (e.g., through the stomach to the intestine) before being dissolved/degraded/eroded due to exposure of certain conditions (e.g., pH, temperature, enzymes) of the GI tract. An enteric material may prevent a drug from degradation by gastric fluid and enzymes.

The term "jet," as used herein, refers to a collimated stream of fluid, e.g., liquid or suspension, that is stable without breaking up into a spray. A jet may be formed by forcing the fluid, e.g., liquid or suspension, through an opening in an ingestible device. Generally, a jet maintains a stable form and is capable of achieving its intended purpose by maintaining appropriate properties (e.g., to penetrate a surface), such as its diameter and/or velocity.

As used herein, "jet diameter" is the cross-sectional diameter of a jet at a given location.

As used herein, "average jet diameter" refers to the average cross-sectional diameter of a jet between the location where the jet is formed (e.g., a nozzle opening through which the dispensable substance is delivered from the ingestible device) and the location where the jet impacts the GI tissue of the subject.

"Jet stable length," as used herein, refers to the distance from an opening (e.g., nozzle opening) of an ingestible device that a dispensable substance delivered through the opening remains in the form of a jet.

"Jet velocity," as used herein is the average fluid velocity across the cross-section of a jet at a given point in time.

As used herein, "peak jet velocity," refers to the maximum jet velocity of a jet at the interface of the lumen and the surface of the GI tract facing the lumen. In general, the peak jet velocity is achieved at the time of initial delivery of the dispensable substance from the ingestible device.

As used herein, "minimum jet velocity," refers to the minimum velocity of a jet at the interface of the lumen and the surface of the GI tract facing the lumen. In general, the minimum jet velocity is achieved at the end of delivery of the dispensable substance from the ingestible device.

"Mean jet velocity" and "average jet velocity," as used herein, refer to the average velocity of a jet at the interface of the lumen and the surface of the GI tract facing the lumen as determined over the time that the ingestible device delivers the dispensable substance.

As used herein, "peak jet power" refers to the maximum power of a jet at the interface of the lumen and the surface of the GI tract facing the lumen. In general, the peak jet power is achieved at the time of initial delivery of the dispensable substance from the ingestible device.

As used herein, "minimum jet power," refers to the minimum power of a jet at the interface of the lumen and the surface of the GI tract facing the lumen. In general, the minimum jet power is achieved at the end of delivery of the dispensable substance from the ingestible device.

"Mean jet power" and "average jet power," as used herein, refer to the average power of a jet at the interface of the lumen and the surface of the GI tract facing the lumen as determined over the time that the ingestible device delivers the dispensable substance.

"Jet power during delivery," as used herein, refers to the power of a jet at the interface of the lumen and the mucosa of the GI tract of a subject.

"Jet pressure," as used herein, refers to the pressure of a jet at the interface of the lumen and the surface of the GI tract facing the lumen. As an example, the jet pressure can be the pressure by the jet measured at the intestinal wall. In some embodiments, jet pressure is referred to herein as "impact pressure."

"Peak jet pressure," as used herein, refers to the maximum pressure of a jet at the interface of the lumen and the surface of the GI tract facing the lumen. In general, the peak jet pressure is achieved at the time of initial delivery of the dispensable substance from the ingestible device.

As used herein, "minimum jet pressure," refers to the minimum pressure of a jet at the interface of the lumen and the surface of the GI tract facing the lumen. In general, the minimum jet pressure is achieved at the end of delivery of the dispensable substance from the ingestible device.

"Mean jet pressure" and "average jet pressure," as used herein, refer to the average pressure of a jet at the interface of the lumen and the surface of the GI tract facing the lumen as determined over the time that the ingestible device delivers the dispensable substance.

"Jet force," as used herein, refers to the force of a jet at the interface of the lumen and the surface of the GI tract facing the lumen. In some embodiments, jet force is referred to herein as "impact force."

"Peak jet force," as used herein, refers to the maximum force of a jet at the interface of the lumen and the surface of the GI tract facing the lumen. In general, the peak jet force is achieved at the time of initial delivery of the dispensable substance from the ingestible device. In some embodiments, peak jet force is referred to herein as "impact force."

As used herein, "minimum jet force," refers to the minimum force of a jet at the interface of the lumen and the mucosa of the GI tract of a subject. In general, the minimum jet force is achieved at the end of delivery of the dispensable substance from the ingestible device.

"Mean jet force" and "average jet force," as used herein, refer to the average pressure of a jet at the interface of the lumen and the surface of the GI tract facing the lumen as determined over the time that the ingestible device delivers the dispensable substance.

As used herein, "fluid volume" refers to the volume of the dispensable substance contained in the ingestible device.

"Initial fluid volume," as used herein, refers to the volume of the dispensable substance contained in the ingestible device just prior to delivery of the dispensable substance from the ingestible device.

"Final fluid volume," as used herein, refers to the volume of the dispensable substance contained in the ingestible device just after delivery of the dispensable substance from the ingestible device has ended.

As herein, "delivered fluid volume" refers to the volume of dispensable substance delivered from the ingestible device. In some embodiments, the delivered fluid volume is less than the fluid volume.

"End round" as used herein is the radius on the curve at the end of the housing of the ingestible device.

"Fluid pressure" as used herein refers to the pressure in the fluid volume.

As used herein, "peak fluid pressure" refers to maximum pressure generated in the fluid volume. Generally, the peak fluid pressure is achieved at initial delivery of the dispensable substance from the ingestible device. In some embodiments, peak fluid pressure is referred to herein as "internal pressure on the pharmaceutical formulation in the device, prior to release from the device."

As used herein, "minimum fluid pressure" refers to minimum pressure generated in the fluid volume. Generally, the minimum fluid pressure is achieved at the end of delivery of the dispensable substance from the ingestible device.

"Fluid pressure during delivery," as used herein, refers to the pressure in the fluid volume as it decreases during the delivery process.

As used herein, "nozzle" refers to a channel between a fluid reservoir space and an external environment. Generally, in embodiments in which a nozzle is used, pressure in the fluid volume generates a high speed flow of fluid through the nozzle to produce a fluid jet at the opening of the nozzle through which the dispensable substance leaves the ingestible device and enters an environment exterior to the ingestible device.

"Nozzle diameter," as used herein, refers to the diameter of the opening of the nozzle at the opening of the nozzle through which the dispensable substance leaves the ingestible device and enters an environment exterior to the ingestible device.

As used herein, "nozzle length" refers to the length of the opening of the nozzle.

"Nozzle stand-off distance," as used herein, refers to the distance between: 1) the opening of the nozzle through which the dispensable substance leaves the ingestible device and enters an environment exterior to the ingestible device; and 2) the interface of the lumen and the surface of the GI tract facing the lumen.

As used herein, the "internal pressure" of an ingestible device refers to the pressure applied to a dispensable substance, such as a therapeutic agent, or a formulation containing a therapeutic agent, contained in the ingestible device prior to delivery of the dispensable substance from the ingestible device. In some embodiments, the internal pressure is provided by the drive force generator of the ingestible device. In certain embodiments, the internal pressure is greater than the fluid pressure. This may be due, for example, to friction, such as O-ring friction, acting on the drive coupling of the ingestible device. This friction is referred to herein as the "piston friction."

"Nozzle pressure" as used herein refers to the pressure of a dispensable substance at a nozzle opening as measured at the surface facing the interior of the nozzle as the dispensable substance is delivered from the ingestible device. In general, for a given ingestible device at a given point in time, the nozzle pressure is approximately the same as the fluid pressure.

"Topical delivery" or "topical administration," as used herein, refers to a route of administration of a dispensable substance (for example, a therapeutic agent or a pharmaceutical formulation containing a therapeutic agent) where the dispensable substance is delivered to a localized area of the body or to the surface of a body part, regardless of the location of the effect; more particularly, the topical administration of the dispensable substance comprises releasing the dispensable substance to the lumen of the GI tract, a surface of the GI tract facing the lumen, a mucous membrane and/or a lining of the gastrointestinal tract of a subject, including, but not limited to, a surface, mucous membrane or lining containing one or more disease sites, such as gastrointestinal mucosal lesions. The effect of the topical delivery or topical administration of the dispensable substance may be local to, or away from (e.g., distal to), the site of the topical administration.

"Epithelial delivery" or "epithelial administration," as used herein, refers to a route of administration of a dispensable substance (for example, a therapeutic agent or a pharmaceutical formulation containing a therapeutic agent) where the dispensable substance is directly delivered into the mucus or onto the epithelium, but not past the epithelial layer, of the GI tract of a subject, such as the small or large intestine, from which the dispensable substance can act locally or peripherally. In some embodiments of epithelial delivery or epithelial administration, the therapeutic agent can move deeper into the GI tissue (i.e., past the epithelial layer) away from the site of direct delivery, such as, for example, via diffusion or active transport.

"Trans-epithelial delivery" or "trans-epithelial administration," as used herein, refers to a route of administration of a dispensable substance (for example, a therapeutic agent or a pharmaceutical formulation containing a therapeutic agent) where the dispensable substance is directly delivered through the epithelial layer of the mucosa of the GI tract to the submucosa of the GI tract of a subject; optionally, at least a portion of the dispensable substance is directly delivered past the epithelial layer to a region of the mucosa beneath the epithelial layer. In embodiments of trans-epithelial delivery in which a portion of the dispensable substance is directly delivered to a region of the mucosa beneath the epithelial layer, at least some (e.g., all) of the portion of the dispensable substance is directly delivered to the lamina propria. Once the therapeutic agent or a pharmaceutical formulation containing a therapeutic agent is directly delivered past the epithelial layer of the GI tract, it is available for systemic exposure of the therapeutic agent to the subject.

General Introduction

Figure 1B:
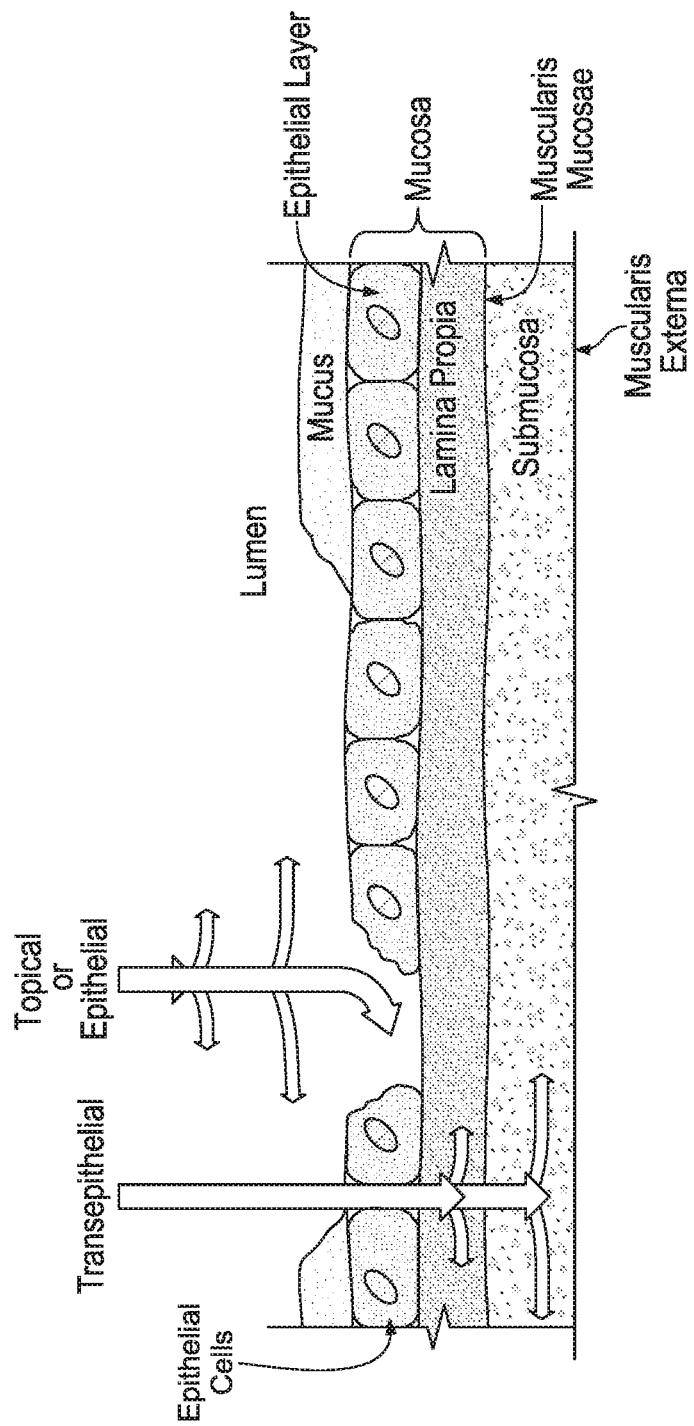
FIG. 1B is a schematic cross section corresponding to FIG. 1A but for diseased intestinal tissue.

FIG. 1A schematically describes the different regions of healthy intestinal tissue, presented in a cross section. The regions include the lumen of the GI tract, the mucus of the GI tissue, the mucosa of the GI tissue and the submucosa of the GI tissue. The mucosa of the GI tissue includes the epithelial layer and the lamina propria. The muscularis mucosae separates the mucosa from the submucosa. The muscularis extrema is below the submucosa. FIG. 1B schematically describes corresponding regions of diseased intestinal tissue, presented in a cross section.

An ingestible device described herein can deliver a therapeutic agent via topical delivery (without being directly delivered to the mucus, mucosa or submucosa), epithelial delivery (directly delivered to the mucus or epithelium without being directly delivered past the epithelial layer to the mucosa or submucosa) or trans-epithelial delivery (directly delivered to the submucosa and/or into a region of the mucosa beneath the epithelial layer, such as the lamina propria.

In general, the form of delivery may depend on the design of the ingestible device and parameters used with the device (e.g., internal pressure, fluid pressure, number of nozzles, design of nozzles). Holding other parameters constant, at relatively low fluid pressures and/or internal pressures, the therapeutic agent may be topically delivered, while higher fluid pressures and/or internal pressures may result in epithelial delivery, and still higher fluid pressures and/or internal pressure may result in trans-epithelial delivery. During trans-epithelial delivery, a bolus of the therapeutic agent initially contained in the dispensable substance may form within the submucosa and/or into a region of the mucosa beneath the epithelial layer, such as the lamina propria.

In some embodiments, the following holds. The ingestible device is designed to deliver a dispensable substance, for example, a therapeutic agent or a pharmaceutical formulation containing a therapeutic agent through the epithelial layer of the mucosa of the GI tract. In some embodiments, the dispensable substance is a solution formulation; optionally, a suspension. In some embodiments, the dispensable substance enters the submucosa and/or into a region of the mucosa beneath the epithelial layer, such as the lamina propria, of the small intestine, where it can be absorbed systemically. After the patient swallows the device, it passes through the GI tract and eventually reaches the small intestine. The device includes a restraining mechanism, an optionally a triggering mechanism (e.g., a degradable and/or erodible coating, such as an enteric coating, that partially or completely degrades and/or erodes when the device reaches the desired location in the GI tract). The desired location can be the small intestine or the large intestine. When the device is configured for trans-epithelial GI tract delivery to the submucosa submucosa and/or into a region of the mucosa beneath the epithelial layer, such as the lamina propria, the preferred location can be the small intestine. With the restraining element is removed, relative movement between certain components (e.g., sliding of a component) occurs such that one or more openings in the ingestible device (e.g., in a compartment containing the dispensable substance, such as a reservoir, sometimes referred to herein as the "drug reservoir," "storage reservoir" or "substance reservoir") become aligned with one or more additional openings (e.g., one or more nozzles) in the ingestible device (e.g., in the housing). With the ingestible device now in this open position, a force (e.g., generated by a force generator and/or transferred by a drive coupling, such as a membrane or a piston) forces the dispensable substance from the drug reservoir out of the device via the one or more openings (e.g., the one or more nozzles). The dispensable substance is delivered as a jet of fluid (e.g., liquid) through the epithelial layer of the mucosa and directly into the submucosa and/or into a region of the mucosa beneath the epithelial layer, such as the lamina propria, of the GI tract in the form of single or multiple boluses. After swallowing the device, the device travels through the GI tract (mouth, esophagus, stomach, duodenum, jejunum, ileum, cecum and colon), ultimately exiting the GI tract via the anus.

T As used herein, "minimum jet force," refers to the minimum force of a jet at the interface of the lumen and the mucosa of the GI tract of a subject. In general, the minimum jet force is achieved at the end of delivery of the dispensable substance from the ingestible device.

"Mean jet force" and "average jet force," as used herein, refer to the average pressure of a jet at the interface of the lumen and the surface of the GI tract facing the lumen as determined over the time that the ingestible device delivers the dispensable substance.

As used herein, "fluid volume" refers to the volume of the dispensable substance contained in the ingestible device.

"Initial fluid volume," as used herein, refers to the volume of the dispensable substance contained in the ingestible device just prior to delivery of the dispensable substance from the ingestible device.

"Final fluid volume," as used herein, refers to the volume of the dispensable substance contained in the ingestible device just after delivery of the dispensable substance from the ingestible device has ended.

Thus, in general, the ingestible devices disclosed herein provide delivery of therapeutic agent to the GI tract of a subject. In one aspect, the disclosure relates to trans-epithelial delivery of a dispensable substance (e.g., a therapeutic agent or a formulation comprising a therapeutic agent) to the GI tract of a subject. Accordingly, the disclosure provides an ingestible device that can directly deliver a dispensable substance (e.g., a therapeutic agent or a formulation comprising a therapeutic agent) to the submucosa and/or into a region of the mucosa beneath the epithelial layer, such as the lamina propria, of the GI tract of a subject, which may result in systemic exposure of the therapeutic agent to the subject. In such embodiments, the ingestible device is configured to directly deliver the dispensable substance past the epithelial cell layer of the mucosa and into the submucosa and/or into a region of the mucosa beneath the epithelial layer, such as the lamina propria, of the GI tract, where the therapeutic agent so delivered is available for systemic uptake. In some embodiments, systemic exposure of the therapeutic agent is achieved by trans-epithelial delivery of the dispensable substance into the submucosa and/or into a region of the mucosa beneath the epithelial layer, such as the lamina propria, of the small intestine, for example, in the duodenum, the jejunum, and/or the ileum. In some further embodiments, the trans-epithelial delivery directly delivers the dispensable substance into the submucosa and/or into a region of the mucosa beneath the epithelial layer, such as the lamina propria, of the GI tract such that the percent systemic uptake of the therapeutic agent via the trans-epithelial delivery relative to intravenous or subcutaneous administration is at least about 10% (e.g., at least about 15%, at least about 20%, at least about 25% or more).

In some embodiments, the direct delivery of the therapeutic agent to the submucosa and/or into a region of the mucosa beneath the epithelial layer, such as the lamina propria, via trans-epithelial delivery may also or alternatively provide therapeutic effects locally and/or away from (e.g., distal to) the site of the direct delivery.

In some embodiments, the trans-epithelial delivery may directly deliver a first portion of the dispensable substance to the submucosa of the GI tract, and a second portion of the dispensable substance to the mucosa, all or a further portion of which may be directly delivered to the lamina propria. In some embodiments, the second portion of the dispensable substance delivered to the mucosa, such as the lamina propria, of the GI tract via the trans-epithelial delivery may provide therapeutic effects locally and/or away from (e.g., distal to) the site of the direct delivery.

In another aspect, the disclosure relates to epithelial delivery of a dispensable substance (e.g., a therapeutic agent or a formulation comprising a therapeutic agent) to the GI tract of a subject. Accordingly, the disclosure provides an ingestible device configured to directly deliver a dispensable substance (e.g., a therapeutic agent or a formulation comprising a therapeutic agent) into the mucus, but not past the epithelial layer of the mucosa, of the small or large intestine, from which it may provide therapeutic effects locally and/or away from (e.g., distal to) the site of the direct delivery. In some further embodiments, the ingestible device directly delivers the dispensable substance such that it contacts the surface of the epithelial cell layer of the mucosa facing the lumen, but as previously noted, the epithelial delivery does not directly delivery the dispensable substance past the epithelial layer of the mucosa. In some embodiments, the device is configured so that the dispensable substance is delivered from the device with sufficient force to provide the epithelial delivery, the force being lower than that required for trans-epithelial delivery to the GI tract. In some further embodiments, the epithelial delivery directly delivers the dispensable substance into the mucus of the GI tract such that the percent systemic uptake of the therapeutic agent via the epithelial delivery relative to intravenous or subcutaneous administration is greater than that for topical delivery, but less than for trans-epithelial delivery. In other embodiments, the epithelial delivery directly delivers the dispensable substance into the mucus of the GI tract such that the percent systemic uptake of the therapeutic agent via the epithelial delivery relative to intravenous or subcutaneous administration is about 0.5% to about 10% or more (e.g., about 0.5%, about 2%, about 3%, about 4%, about 5%, about 6%, about 7%, about 8%, about 9%, about 10%, or more).

In some embodiments of epithelial delivery, the therapeutic agent directly delivered into the mucus of the GI tract via the epithelial delivery may undergo active or passive transport or diffusion past the epithelial layer. Once past the epithelial layer, the therapeutic agent may provide therapeutic effects locally and/or away from (e.g., distal to) the site of the direct delivery. In some embodiments, the therapeutic agent binds to a therapeutic target present in the GI epithelial layer or elicits other pharmacodynamic effects locally or away from the site of delivery via immune cells or tissue in the GI tract (e.g., dendritic cells, lymphocytes, mucosa-associated lymphoid tissue).

In yet another aspect, this disclosure relates to topical delivery of a dispensable substance (e.g., a therapeutic agent or a formulation comprising a therapeutic agent) to the GI tract of a subject. Accordingly, the disclosure provides an ingestible device configured to deliver the dispensable substance (e.g., a therapeutic agent or a formulation comprising a therapeutic agent) into the lumen and/or onto the mucus or other surface (e.g., a diseased surface) of the GI tract facing the lumen of the small or large intestine, from which it may provide therapeutic effects locally and/or away from (e.g., distal to) the site of delivery. In some embodiments, the device is configured so that the dispensable substance is delivered from the device with sufficient force so that the dispensable substance is delivered topically, the force being lower than that required for the epithelial or the trans-epithelial delivery to the GI tract. In some embodiments, the topical delivery to the GI tract results in reduced systemic uptake of the therapeutic agent compared to trans-epithelial delivery to the GI tract, intravenous or subcutaneous delivery.

In some further embodiments, topical delivery delivers the dispensable substance into the lumen and/or onto the mucus or the other surface facing the lumen of the GI tract such that the percent systemic uptake of the therapeutic agent via the topical delivery relative to intravenous or subcutaneous administration is less than about 20%, less than about 10%, less than about 5%, less than about 4%, less than about 3%, less than about 2% or less than about 1%.

In some embodiments, the topical delivery to the GI tract results in negligible or no systemic uptake of the therapeutic agent compared to trans-epithelial delivery to the GI tract, intravenous or subcutaneous delivery. In some embodiments, the topically delivered dispensable substance may spread over the mucus or other surface facing the lumen of the GI tract, thereby coating the surface of the GI tract at or away from (e.g., distal to) the site of delivery. In some embodiments, upon or after the dispensable substance has been topically delivered, the therapeutic agent may undergo transport (e.g., diffusion) from the surface of the mucus into the mucus, and optionally, active or passive transport or diffusion past the epithelial layer of the mucosa.

In some embodiments, the mucus and/or epithelial layer of the mucosa may be disrupted or even absent, such as in a patient having a disease or condition of the GI tract. In such embodiments, the topical delivery of the dispensable substance to the GI tract of the patient may provide direct delivery of the dispensable substance to the surface of the GI tract facing the lumen, such as mucosal tissue exposed by said disruption and/or absence (e.g., both the mucus layer and/or epithelial layer are completely or partially absent or compromised in portions of the GI tract due to a disease or condition). For example, in some embodiments, the topical delivery of the dispensable substance to the GI tract of the patient may provide topical delivery to one or more lesions of the GI tract. In some embodiments, the disease or condition is an inflammatory bowel disease. In some further embodiments, the inflammatory bowel disease is ulcerative colitis. In some other embodiments, the inflammatory bowel disease is Crohn's disease.

Accordingly, provided herein are new systemic delivery devices and methods that deliver therapeutic agents into the small intestinal mucosa and/or submucosa by jet injection. Current methods of administration for most large molecule therapeutic agents are subcutaneous (SC), intramuscular (IM), or bolus intravenous (IV) injection targeting the systemic circulation. The devices and methods described herein provide an alternative route of administration to current injectable medications, which can lead to greater convenience and compliance since they minimize or avoid the logistical challenges, patient compliance and adherence challenges, pain, and discomfort associated with traditional routes of administration.

Also, by providing a higher concentration of therapeutic in GI tissue, the devices and methods described herein are particularly well-suited for treatment of diseases and conditions of the endoderm, including the liver.

Device Description

General

In general, the ingestible device is suitable for swallowing by a patient and for safely and effectively passing through the GI tract of the patient. Generally, the device can be in the shape of a capsule, a pill or any other swallowable form that may be orally consumed by the subject. In some embodiments, the ingestible device can be swallowed voluntarily under medical supervision or in a home use environment with instruction provided ahead of subsequent ingestion. Generally, ingestible devices are intended for single subject, single use. The ingestible device can have a density high enough to cause the ingestible device to sink within human stomach fluid, e.g., the unfilled ingestible device can have a density of greater than 1.01 g/cm$^3$. The ingestible device can have maximum dimensions that allow the ingestible device to pass through an average human GI tract. In some embodiments, the ingestible device is configured to prevent tumbling in the small intestine of a human. For example, the ingestible device is of sufficient length whereby it will not tumble in the small intestine of a human before, during, or after the dispensable substance is released. Generally, the ingestible device is configured to deliver a sufficient amount of therapeutic agent contained in the dispensable substance to be effective for its intended purpose. In general, the ingestible device's patient-contacting portions (e.g., exterior surface) and dispensable substance-contacting portions are biocompatible. Preferably, the device can withstand an indirect bite force without damaging the housing damage or resulting in leakage. As an example, when containing the dispensable substance, the ingestible device can withstand a bite force of at least about 60 Newtons (N). Generally, unless otherwise intended (see discussion below) components of the ingestible device can withstand exposure to a pH range expected in the human GI tract without substantial loss of functionality, substantial structural damage, or substantial leakage. As an example, in some embodiments, the ingestible device can withstand submersion in a pH 1.5±0.5 fluid environment for at least about 24 hours without substantial loss of functionality, substantial structural damage, or substantial leakage. In general, the ingestible device can maintain an external fluid barrier between the inside of the ingestible device and the GI tract of the subject during transit therethrough. Generally, the ingestible device can withstand external fluid pressures to which it is exposed during use without substantial loss of functionality, substantial structural damage, or substantial leakage. As an example, in some embodiments, the ingestible device undergoes no substantial loss of functionality, substantial structural damage, or substantial leakage when exposed to a sustained pressure of at least about 2 psig for at least about 24 hours and/or when exposed to a momentary pressure of at least about 5 psig momentary pressure for at least about 1 minute. In general, an ingestible device disclosed herein includes the following features.

Housing

In some embodiments, the ingestible device comprises a housing configured to maintain its mechanical integrity during use of the ingestible device. In some embodiments, the housing has a first portion and a second portion. In some further embodiments, the housing has a first actuation component on the housing, and a second actuation component within the housing. In some embodiments, a storage reservoir is located within the housing, wherein the storage reservoir is configured to store a dispensable substance. In some embodiments, the housing has an opening in fluid communication with the storage reservoir. In some embodiments, the ingestible device employs an electrolytic mechanism for creating one or more openings in the ingestible device, wherein a substance can be dispensed through said opening as described in PCT Application Number PCT/US2019/021814, which published as WO2019178071, and which is incorporated by reference herein. For example, the housing may comprise an external electrolytic circuit (electrolytically erodible surface being on the exterior of the device), whereby the surrounding gastric fluids are the electrolyte that completes an electrolytic circuit between anode and cathode. With sufficient bias voltage (e.g., 1.5-15 volts, such as 3-5 volts), the anode will dissolve or erode electrolytically and thus create an opening in the housing within a desired time interval. In some embodiments, the one or more openings created by an electrolytic mechanism are coupled to one or more nozzles, thereby allowing for trans-epithelial, epithelial, or topical delivery as described herein. In some embodiments an ingestible device includes an enteric coating on the housing. In certain embodiments, the enteric coating covers only certain regions of the housing. The housing may be designed to withstand the chemical and mechanical environment of the GI tract (e.g., effects of muscle contractile forces and concentrated hydrochloric acid in the stomach).

Nozzles

In some embodiments, an ingestible device includes one or more nozzles in fluid communication with the one or more openings in the ingestible device. The nozzle(s) is(are) configured so that the dispensable substance through the nozzle(s) when the dispensable substance is delivered from the ingestible device. In general, a nozzle can have any desired size and shape appropriate for the desired type of delivery of a dispensable substance from the ingestible device. In certain embodiments, a nozzle has a shape and/or size appropriate for trans-epithelial delivery, epithelial delivery or topical delivery. In some embodiments, an ingestible device includes more than one nozzle.

Restraining Mechanism

In some embodiments, the ingestible device comprises a restraining mechanism. Generally, a restraining mechanism has a first state in which it is configured to prevent the dispensable substance from exiting the ingestible device via the opening(s), and a second state in which it is configured so that it does not prevent the dispensable substance from exiting the ingestible device via the opening(s). The restraining mechanism can be configured to transition from its first state to its second state when it is exposed to a triggering condition. The restraining mechanism may be provided by one or more restraining elements. The restraining elements can have a first state in which they are configured to prevent the dispensable substance from exiting the ingestible device via the openings, and a second state in which they are configured to allow the dispensable substance to exit the ingestible device via the openings. The restraining elements can be configured to transition from the first state to the second state when the restraining elements are exposed to a triggering condition. In some embodiments, the restraining elements comprise a first type of restraining element and a second type of restraining element different from the first type of restraining element. The first type of restraining element can be configured to transition to its second state before the second type of restraining element transitions to its second state. In some embodiments, a restraining elements comprises a lid, a pin, a band, a plug, a dowel, a clasp, a clamp, a flange, a rivet, an annulus, a torus, a ring, a wafer, a cylinder, an asymmetric shape such as a partial annulus, a partial torus, a partial ring, a partial wafer, a partial cylinder, or any combination thereof (e.g., two partial tori). Optionally, a restraining element can have a filled interior (e.g., no hole). Optionally, a restraining element can have a varying thickness (e.g., a center region that is thinner than the edges). In some embodiments, the restraining elements comprise a plasticizer such as triethyl citrate (TEC). In some embodiments, the restraining elements comprise a degradable and/or erodible material, such as, for example, an enteric material. The enteric material may be degradable and/or erodible in the small intestine of the GI tract, or may be degradable and/or erodible in the large intestine of the GI tract, for example, the colon. In some embodiments, a restraining mechanism can be a mechanism that prevents the dispensable substance from being delivered from the ingestible device even when the drive force generator (or optionally the drive coupling) applies an internal force. For example, such a restraining can be an element (e.g., a pin, a band, a plug) in the opening (e.g., nozzle opening) through which the dispensable substance can be delivered from the ingestible device. Such a restraining element can be formed, for example, of a material that degrades and/or erodes as discussed above.

In general, a restraining mechanism includes a material that will lose a sufficient degree of its mechanical strength at the desired location to cause the ingestible device to deliver the dispensable substance. The material may undergo loss of mechanical strength to any appropriate mechanism or combination of mechanisms, including, for example, moisture ingress, solubility, swelling, leaching, eroding and/or the like.

In some embodiments, a restraining mechanism includes a degradable and/or erodible material such as a water soluble material, optionally with one or more coatings of one or more enteric materials. The degradable and/or erodible material is designed to lose its mechanical strength in the presence of moisture (e.g., liquid present in the GI tract).

Generally, an enteric material erodes after being swallowed, e.g., in the small intestine or in the large intestine. In some embodiments, the degradable and/or erodible material is coated with an enteric material that limits the amount of moisture or fluid reaching the degradable and/or erodible material, whereby the degradable and/or erodible material is able to resist a trigger load, for example, for at least two hours at a pH of 1.1

Triggering Mechanism

In some embodiments, the ingestible device comprises a triggering mechanism. In some embodiments, a triggering mechanism is configured to cause the dispensable substance within the fluid volume to be released under one or more triggering conditions. In some embodiments, a triggering mechanism initiates a drive force generator. In some embodiments, a triggering mechanism incorporates a mechanical feature like a restraining mechanism. As an example, one or more restraining elements degrade and/or erode in the presence of certain GI tract conditions (e.g., pH greater than 5), thereby triggering a drive force generator, such as a compressed spring. As another example, a spring may have a piercing element that pierces a cylinder with compressed gas, whereby the released gas acts as a force applied to a dispensable substance. In certain embodiments, a triggering mechanism incorporates an electrical feature. For example, an enteric coating degrades and/or erodes in the presence of certain GI tract conditions (e.g., pH greater than 5), thereby exposing conductors to intestinal fluid, which acts as a liquid conductor to triggering the drive force generator. In some embodiments, a triggering condition relates to a condition of the GI tract. In some embodiments, the condition of the GI tract comprises at least one condition selected from the group consisting of temperature, pH, presence of one or more enzymes, and time.

Generally, the gas within the gas cylinder can be a single gas or a mixture of two or more gases. Exemplary gases include air, nitrogen, oxygen, carbon dioxide, hydrofluorocarbon gases, and noble gases (e.g., helium, neon, argon, krypton, xenon). In some embodiments, the gas within the gas cylinder is a mixture of gases that include helium (e.g., nitrogen/helium mixture, argon/helium mixture). Optionally, such gas mixtures include at most about 5% helium. The presence of helium in a gas mixture can allow for leak checking the gas cylinder based on the presence of helium gas adjacent the exterior of the gas cylinder.

In some embodiments, the element (e.g., piercer) has a contact point on the breakable seal. Optionally, the contact point is concentrated in a relatively small local area. For example, the piercer may be a needle or a thin rod element that is cut at an angle to initially generate a single point contact. Relative to the breakable seal, the point of initial contact may be on-center or off-center. Having the point of initial contact off-center relative to the breakable seal can result in a reduced force applied by the element (e.g., piercer).

Drive Force Generator

The drive force generator is configured to provide the requisite force to the dispensable substance such that, when the restraining mechanism is removed, the dispensable substance is delivered from the ingestible device as desired. The drive force generator can apply force using different mechanisms, including, for example, a compressed gas, a gas generated by chemical reaction, a spring, a liquid-gas mixture, an impact ram, a sudden expansion caused by a controlled exothermic reaction, or the like. When the drive force generator is a spring, the spring can have one or more of the following properties: the outer diameter of the spring is smaller than the inner diameter of the ingestible device; the compressed length of the spring is minimized to leave more space for dispensable substance; the spring is of a conical shape, potentially with a reduction in the solid length of the spring; the free length of the spring is maximized and larger than the free length of the inner cavity of the ingestible device to ensure an acceptable driving pressure is provided throughout the entire time step of delivery; and the spring rate is large enough to provide acceptable pressure from the beginning until the end of delivery of the dispensable substance. Examples of springs include parallel springs, wave springs and conical springs. Examples of compressed gas include a gas charged within the ingestible device, and a container (e.g., cylinder) of compressed gas. In some embodiments, the compressed gas is a gas cylinder from Picocyl. Exemplary gas cylinders are disclosed, for example, in US 2017-0258583, which is incorporated by reference herein.

Drive Coupling

In general, the drive force coupling transfers a force from the drive force generator to the dispensable substance. Examples of a drive coupling include a piston and a membrane. Examples of membranes include balloons and elastomeric materials. An example of a piston is an O-ring sealed piston. In some embodiments, a piston is provided by a gas cylinder, e.g., with added O-rings or a custom housing.

Storage Reservoir

In some embodiments, an ingestible device includes a storage reservoir configured to store a dispensable substance. In some embodiments, the storage reservoir stores the dispensable substance. In some embodiments, the storage reservoir is completely disposed within the housing.

Figure 2:
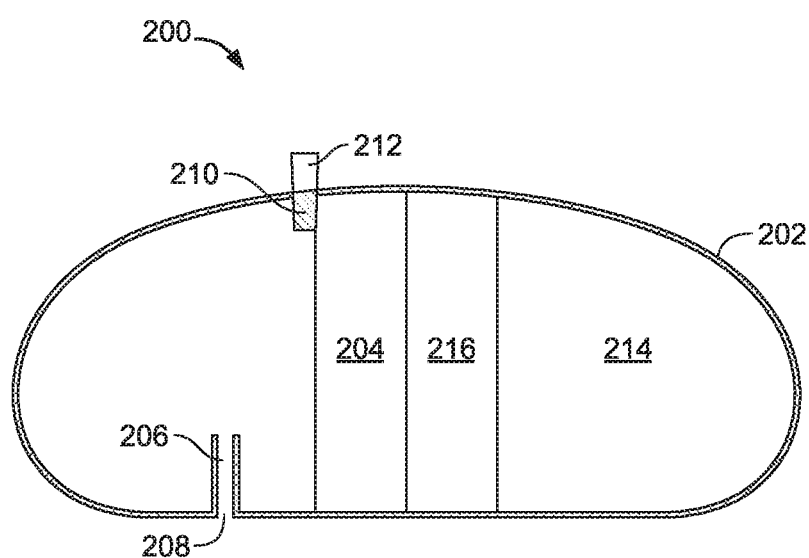
FIG. 2 is a cross section of an ingestible device.

FIG. 2 is a schematic representation of an ingestible device 200 which includes a housing 202, a fluid volume 204 containing a dispensable substance, a nozzle 206 with a nozzle opening 208, a restraining mechanism 210, a triggering mechanism 212, a drive force generator 214 and drive coupling 216. During use, ingestible device 200 is swallowed by a subject and traverses the GI tract. At an appropriate location, the triggering mechanism 212 is triggered, allowing the drive force generator to apply pressure to the drive coupling 216, which then applies pressure to the fluid volume such that at least some of the dispensable substance is delivered out of fluid volume 204, through the nozzle 206, and out of the device 200 via the nozzle opening 208. In some embodiments, the internal pressure is applied, even before the triggering mechanism 212 is triggered. As an example, at an appropriate location, the triggering mechanism 212 is triggered, allowing the drive coupling 216 to apply pressure to the fluid volume 204. In certain embodiments, the internal pressure is not applied until the triggering mechanism 212 is triggered.

Device for Trans-Epithelial Delivery

Generally, trans-epithelial delivery can be achieved at any desired location within the GI tract of a subject. In some embodiments, trans-epithelial delivery is achieved in the small intestine of the subject, such as, for example, in the duodenum, the jejunum and/or the ileum. In certain embodiments, trans-epithelial delivery is achieved in the large intestine of the subject, such as, for example, the cecum or the colon.

In general, an ingestible device for trans-epithelial delivery is configured to deliver a jet of the dispensable substance having a peak jet power of from at least about 1 Watt (e.g., at least about 1.1 Watts, at least about 1.2 Watts, at least about 1.3 Watts, at least about 1.4 Watts, at least about 1.5 Watts, at least about 1.6 Watts, at least about 1.7 Watts, at least about 1.8 Watts) and/or at most about 3 Watts (e.g., at most about 2.9 Watts, at most about 2.8 Watts, at most about 2.7 Watts, at most about 2.6 Watts, at most about 2.5 Watts, at most about 2.4 Watts, at most about 2.3 Watts, at most about 2.2 Watts, at most about 2.1 Watts). In some embodiments, an ingestible device for trans-epithelial delivery is configured to deliver a jet of the dispensable substance having a peak jet power of from about 1 Watt to about 3

Watts (e.g., of from about 1.3 Watts to about 2.8 Watts, of from about 1.5 Watts to about 2.5 Watts).

In general, an ingestible device for trans-epithelial delivery is configured to deliver a jet of the dispensable substance having an average jet power of at least about 0.5 W (e.g., about 0.8 W, about 1 W) and/or at most about 2 W (e.g., at most about 1.7 W, at most about 1.5 W). In some embodiments, a device for trans-epithelial delivery is configured to deliver a jet of the dispensable substance having an average jet power of from about 0.5 W to about 2 W (e.g., from about 0.8 W to about 1.7 W, from about 1 W to about 1.5 W). Generally, an ingestible device for trans-epithelial delivery is configured to deliver a jet of the dispensable substance having a peak jet pressure of at least about 100 psig (e.g., at least about 110 psig, at least about 120 psig, at least about 130 psig, at least about 140 psig, at least about 150 psig, at least about 160 psig, at least about 170 psig, at least about 180 psig, at least about 190 psig) and/or at most about 250 psig (e.g., at most about 240 psig, at most about 230 psig, at most about 220 psig, at most about 210 psig). In certain embodiments, an ingestible device for trans-epithelial delivery is configured to deliver a jet of the dispensable substance having a peak jet pressure of from about 100 psig to about 250 psig (e.g., from about 140 psig to about 225 psig, from about 180 psig to about 205 psig).

In general, an ingestible device for trans-epithelial delivery is configured to deliver a jet of the dispensable substance having an average jet pressure of 60 psig (e.g., at least about 80 psig, at least about 100 psig) and/or at most about 160 psig (e.g., at most about 140 psig, at most about 120 psig). In some embodiments, an ingestible device for trans-epithelial delivery is configured to deliver a jet of the dispensable substance having an average jet pressure of from about 60 psig to about 160 psig (e.g., from about 80 psig to about 140 psig, from about 100 psig to about 120 psig).

Generally, an ingestible device for trans-epithelial delivery is configured to deliver a jet of the dispensable substance having a peak jet velocity of at least about 25 meters per second (m/s) (e.g., at least about 26 m/s, at least about 27 m/s, at least about 28 m/s, at least about 29 m/s, at least about 30 m/s, at least about 31 m/s, at least about 32 m/s, at least about 34 m/s, at least about 35 m/s, at least about 36 m/s) and/or at most about 45 m/s (e.g., at most about 44 m/s, at most about 43 m/s, at most about 42 m/s, at most about 41 m/s, at most about 40 m/s, at most about 39 m/s, at most about 38 m/s, at most about 37 m/s). In some embodiments, an ingestible device for trans-epithelial delivery is configured to deliver a jet of the dispensable substance having a peak jet velocity of from about 25 m/s to about 45 m/s (e.g., from about 30 m/s to about 42 m/s, from about 34 m/s to about 39 m/s, about 36.5 m/s).

In general, an ingestible device for trans-epithelial delivery is configured to deliver a jet of the dispensable substance having a minimum jet velocity of at least about 15 m/s (e.g., at least about 16 m/s, at least about 17 m/s) and/or at most about 22 m/s (e.g., at most about 21 m/s, at most about 20 m/s). In some embodiments, an ingestible device for trans-epithelial delivery is configured to deliver a jet of the dispensable substance having a minimum jet velocity of from about 15 m/s to about 22 m/s (e.g., from about 16 m/s to about 21 m/s, from about 17 m/s to about 20 m/s).

In general, an ingestible device for trans-epithelial delivery is configured to deliver a jet of the dispensable substance having an average jet velocity of at least about 20 m/s (e.g., at least about 25 m/s) and/or at most about 35 m/s (e.g., at most about 30 m/s). In some embodiments, an ingestible device for trans-epithelial delivery is configured to deliver a jet of dispensable substance having an average jet velocity of from about 20 m/s to about 30 m/s (e.g., about 20 m/s, about 21 m/s, about 22 m/s, about 23 m/s, about 24 m/s, about 25 m/s, about 26 m/s, about 27 m/s, about 28 m/s about 29 m/s, about 30 m/s). In certain embodiments, an ingestible device for trans-epithelial delivery is configured to deliver a jet of dispensable substance having an average jet velocity of from about 25 m/s to about 35 m/s (e.g., about 25 m/s, about 26 m/s, about 27 m/s, about 28 m/s, about 29 m/s, about 30 m/s, about 31 m/s, about 32 m/s, about 33 m/s about 34 m/s, about 35 m/s).

In general, an ingestible device for trans-epithelial delivery is configured to deliver a jet of a dispensable substance having a jet stable length of at least about 0.5 millimeter (mm) (e.g., at least about 1 mm, at least about 1.5 mm, at least about 2 mm, at least about 2.5 mm, at least about 3 mm, at least about 3.5 mm, at least about 4 mm, at least about 4.5 mm, at least about 5 mm) and/or at most about 20 mm (e.g., at most about 15 mm, at most about 10 mm). In certain embodiments, an ingestible device for trans-epithelial delivery is configured to deliver a jet of a dispensable substance having a jet stable length of from about 0.5 mm to about 20 mm (e.g., from about 2 mm to about 20 mm, from about 5 mm to about 20 mm).

In some embodiments, an ingestible device for trans-epithelial delivery is configured to deliver a jet of a dispensable substance having a jet diameter of at least about 0.1 mm (e.g., at least about 0.2 mm, at least about 0.3 mm, at least about 0.4 mm) and/or at most about 2 mm (e.g., at most about 1.5 mm, at most about 1 mm, at most about 0.9 mm, at most about 0.8 mm, at most about 0.7 mm, at most about 0.6 mm, at most about 0.5 mm). For example, such an ingestible device for trans-epithelial delivery is configured to deliver a jet of a dispensable substance having a jet diameter of from about 0.1 mm to about 2 mm (e.g., from about 0.2 mm to about 0.5 mm, from about 0.3 mm to about 0.4 mm, from about 0.3 mm to about 0.5 mm, about 0.35 mm).

In general, an ingestible device for trans-epithelial delivery is configured to provide an internal pressure of at least about 225 psig (e.g., at least about 235 psig, at least about 245 psig, at least about 255 psig, at least about 265 psig, at least about 275 psig, at least about 285 psig, at least about 295 psig, at least about 305 psig, at least about 315 psig) and/or at most about 425 psig (e.g., at most about 400 psig, at most about 390 psig, at most about 380 psig, at most about 375 psig, at most about 370 psig, at most about 360 psig, at most about 350 psig, at most about 340 psig, at most about 330 psig). In certain embodiments, an ingestible device for trans-epithelial delivery is configured to provide an internal pressure of from about 225 psig to about 400 psig (e.g., from about 250 psig to about 375 psig, from about 300 psig to about 340 psig).

In general, an ingestible device for trans-epithelial delivery is configured to have a nozzle pressure at least about 150 psig (e.g., at least about 175 psig, at least about 200 psig, at least about 210 psig, at least about 220 psig, at least about 225 psig, at least about 230 psig, at least about 240 psig, at least about 250 psig, at least about 260 psig, at least about 270 psig, at least about 275 psig, at least about 280 psig, at least about 290 psig, at least about 300 psig, at least about 325 psig) and/or at most about 400 psig (e.g., at most about 375 psig, at most about 365 psig, at most about 355 psig, at most about 350 psig, at most about 345 psig, at most about 335 psig, at most about 325 psig, at most about 315 psig, at most about 305 psig). In certain embodiments, an ingestible device for trans-epithelial delivery is configured to have a nozzle pressure encompassed by any of the endpoints noted in the preceding sentence (e.g., of from about 150 psig to about 400 psig).

Generally, an ingestible device for trans-epithelial delivery is configured to contain a dispensable substance at a peak fluid pressure of at least about 150 psig (e.g., at least about 175 psig, at least about 200 psig, at least about 210 psig, at least about 220 psig, at least about 225 psig, at least about 230 psig, at least about 240 psig, at least about 250 psig, at least about 260 psig, at least about 270 psig, at least about 275 psig, at least about 280 psig, at least about 290 psig, at least about 300 psig, at least about 325 psig) and/or at most about 400 psig (e.g., at most about 375 psig, at most about 365 psig, at most about 355 psig, at most about 350 psig, at most about 345 psig, at most about 335 psig, at most about 325 psig, at most about 315 psig, at most about 305 psig). In certain embodiments, an ingestible device for trans-epithelial delivery is configured to contain a dispensable substance at a peak fluid pressure having any of the endpoints noted in the preceding sentence (e.g., from about 150 psig to about 400 psig).

Generally, an ingestible device for trans-epithelial delivery is configured to contain a dispensable substance at a minimum fluid pressure of at least about 50 psig (e.g., at least about 60 psig, at least about 70 psig) and/or at most about 100 psig (e.g., at most about 90 psig, at most about 80 psig). In some embodiments, an ingestible device for trans-epithelial delivery is configured to contain a dispensable substance at a minimum fluid pressure from about 50 psig to about 100 psig (e.g., from about 60 psig to about 90 psig, from about 70 psig to about 80 psig).

In general, an ingestible device for trans-epithelial delivery is configured to have a piston friction of at least about 1 N (e.g., at least about 2 N, at least about 3 N) and/or at most about 20 N (e.g., at most about 15 N, at most about 12 N).

In certain embodiments, an ingestible device for trans-epithelial delivery is configured to have a piston friction of from 1 N to 20 N (e.g., from 2 N to 15 N, from about 3N to about 12N). In general, an ingestible device for trans-epithelial delivery contains the dispensable substance at an initial fluid volume of at least about 50 microliters (μL) (e.g., at least about 100 μL, at least about 150 μL, at least about 200 μL, at least about 250 μL) and/or at most about 800 μL (e.g., at most about 700 μL, at most about 600 μL, at most about 500 μL, at most about 400 μL). In some embodiments, an ingestible device for trans-epithelial delivery contains the dispensable substance at an initial fluid volume of from about 50 μL to about 800 μL (e.g., from about 100 μL to about 600 μL, from about 200 μL to about 400 μL).

Generally, an ingestible device for trans-epithelial delivery is configured to provide a delivered fluid volume of dispensable substance of at least about 50 microliters (μL) (e.g., at least about 100 μL, at least about 150 μL, at least about 200 μL, at least about 250 μL) and/or at most about 800 μL (e.g., at most about 700 μL, at most about 600 μL, at most about 500 μL, at most about 400 μL). In some embodiments, an ingestible device for trans-epithelial delivery has a fluid volume of dispensable substance of from about 50 μL to about 800 μL (e.g., from about 50 μL to about 500 μL, from about 100 μL to about 450 μL, from about 100 μL to about 600 μL, from about 200 μL to about 400 μL, from about 250 μL to about 400 μL, from about 300 μL to about 400 μL).

In general, an ingestible device for trans-epithelial delivery contains the dispensable substance at a final fluid volume of at most about 100 microliters (μL) (e.g., at least about 90 μL, at least about 80 μL, at least about 70 μL, at least about 60 μL) and/or at most least 5 μL (e.g., at most about 10 μL, at most about 20 μL, at most about 30 μL, at most about 40 μL). In some embodiments, an ingestible device for trans-epithelial delivery contains the dispensable substance at a fluid volume of from about 30 μL to about 70 μL (e.g., from about 40 μL to about 60 μL, from about 45 μL to about 55 μL). In general, an ingestible device for trans-epithelial delivery is configured to directly deliver at least about 50% (e.g., at least about 60%, at least about 70%, at least about 80%, at least about 90%, at least about 95%, at least about 97%) of the dispensable substance from the ingestible device to the submucosa and/or the mucosa (e.g., into the lamina propria).

In general, an ingestible device for trans-epithelial delivery has at least 1 opening for delivery of dispensable substance (e.g. at least 2 openings for delivery of dispensable substance, at least 3 openings for delivery of dispensable substance, at least 4 openings for delivery of dispensable substance) and/or most about 8 openings for delivery of dispensable substance (e.g., at most 7 openings for delivery of dispensable substance, at most 6 openings for delivery of dispensable substance, at most 5 openings for delivery of dispensable substance, at most 4 openings for delivery of dispensable substance). In certain embodiments, an ingestible device for trans-epithelial delivery has from 1 to 8 openings for delivery of dispensable substance (e.g., from 2 to 4 openings for delivery of dispensable substance, 2 opening for delivery of dispensable substance). In some embodiments, an ingestible device for trans-epithelial delivery has one or more nozzles, with each nozzle having a nozzle opening for delivering dispensable substance. In such embodiments, the ingestible device can have at least 1 nozzle (e.g., at least 2 nozzles, at least 3 nozzles, at least 4 nozzles) and/or at most 8 nozzles (e.g., at most 7 nozzles, at most 6 nozzles, at most 5 nozzles, at most 4 nozzles). For example, the ingestible device can have from 1 to 8 nozzles (e.g., from 1 to 5 nozzles, from 2 to 4 nozzles, 2 nozzles). In embodiments in which an ingestible device for trans-epithelial delivery includes one or more nozzles, each nozzle can have a nozzle length of at least about 0.2 mm (e.g., at least about 0.5 mm, at least about 0.7 mm, at least about 1 mm, at least about 2 mm, at least about 3 mm) and/or at most about 5 mm (e.g., at most about 4 mm). In some embodiments, each nozzle can have a nozzle length of from about 0.2 mm to about 5 mm. In embodiments in which an ingestible device for trans-epithelial delivery includes one or more nozzles, each nozzle can have a nozzle diameter of at least about 0.1 mm (e.g., at least about 0.2 mm, at least about 0.3 mm) and/or at most about 2 mm (e.g., at most about 1 mm, at most about 0.8 mm, at most bout 0.5 mm, at most about 0.4 mm). In some embodiments, each nozzle can have a nozzle diameter of from about 0.1 mm to about 2 mm (e.g., from about 0.1 mm to about 1 mm, from about 0.15 mm to about 0.5 mm, from about 0.2 mm to about 0.8 mm, from about 0.25 mm to about 0.45 mm, from about 0.3 mm to about 0.4 mm, from about 0.3 mm to about 0.5 mm, from about 0.34 mm to about 0.36 mm, about 0.35 mm).

In general, an ingestible device for trans-epithelial delivery is configured to provide a delivered fluid volume per opening for delivery of dispensable substance (e.g., per nozzle) of at least about 20 microliters (μL) (e.g., at least about 25 μL, at least about μL, at least about 50 μL, at least about 75 μL, at least about 100 μL) and/or at most about 800 μL (e.g., at most about 700 μL, at most about 600 μL, at most about 500 μL, at most about 400 μL, at most about 300 μL). In some embodiments, an ingestible device for trans-epithelial delivery is configured to provide a delivered fluid volume per opening for delivery of dispensable substance (e.g., per nozzle) of from about 25 µL to about 400 µL (e.g., from about 25 µL to about 300 µL, from about 100 µL to about 300 µL).

In one example, an ingestible device with a nozzle having a nozzle diameter of 0.35 mm diameter and containing a dispensable substance at a peak fluid pressure of 150 psig can deliver a jet of the dispensable substance at an average jet velocity of about 20 m/s and at an average jet impact pressure of about 29 psig.

In another example, an ingestible device having a nozzle pressure of 300 psig can deliver a dispensable substance at an average jet velocity of about 27 m/s and an average jet impact pressure of about 58 psig. In some embodiments, such an arrangement results in piercing of the intestinal wall.

In another example, an ingestible device having a nozzle with a nozzle diameter of 0.35 mm diameter and containing a dispensable substance at a peak fluid pressure of 320 psig can deliver a jet of the dispensable substance having an average jet velocity of about 28 m/s and an average jet impact pressure of about 62.4 psig.

Figure 3:
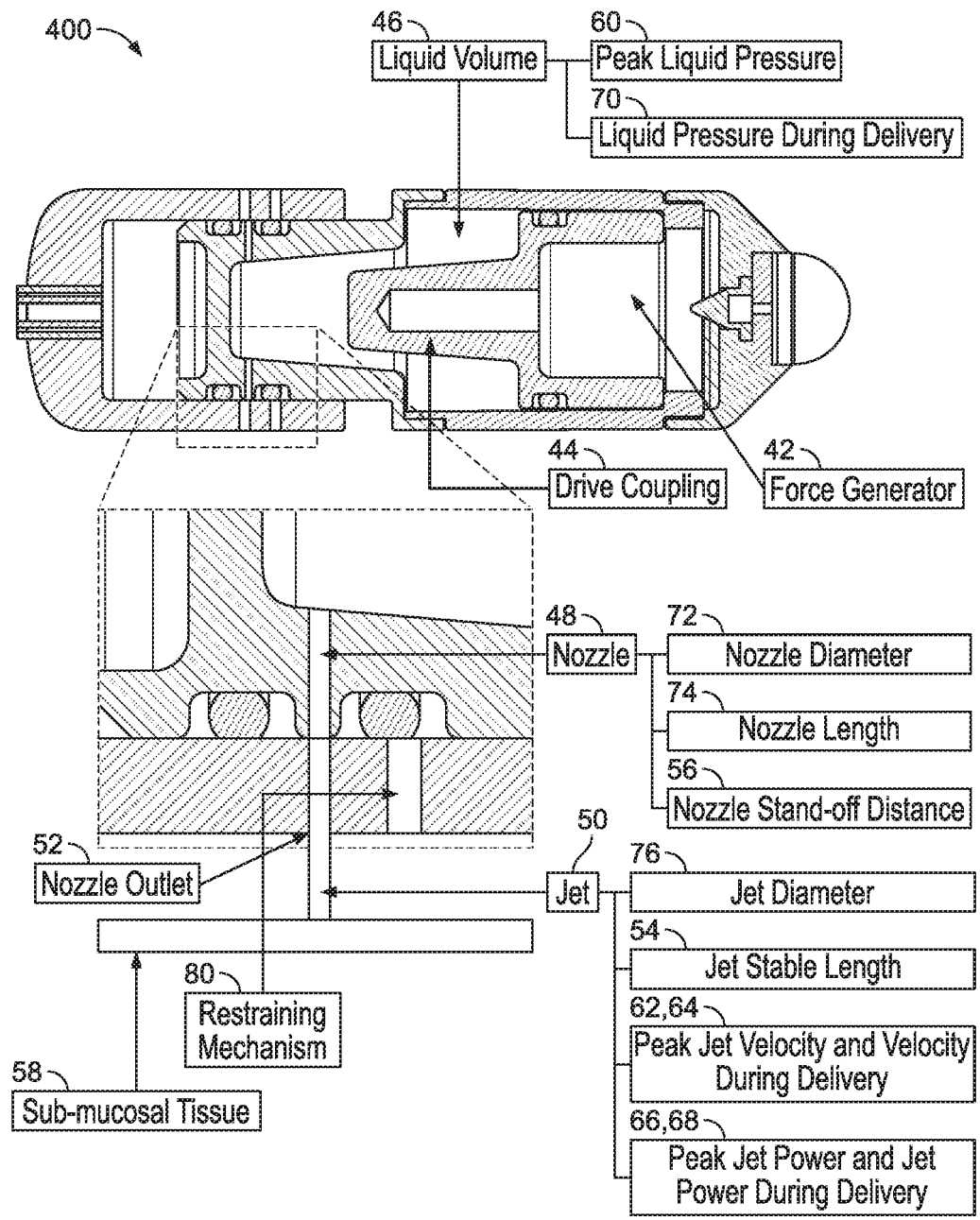
FIG. 3 is a cross section of an ingestible device.

FIG. 3 shows cross sectional views of a representative ingestible device 400 for trans-epithelial delivery, schematically illustrating certain parameters and components of action for the device 400. These include a drive force generator 42 which applies a force (resulting in an internal pressure) to a drive coupling 44. The drive coupling 44 transfers force from the force generator 42 to a fluid volume 46 containing a dispensable substance (e.g., a liquid, a suspension). The force applied to the fluid volume 46 by the drive coupling 44 generates pressure in the fluid volume 46 (fluid pressure). The pressure in the fluid volume 46 generates high-speed flow through an open nozzle 48 to produce a jet 50 of fluid at the nozzle outlet 52 that has a nozzle diameter 72 and the nozzle has a nozzle length 74.

During trans-epithelial delivery, the fluid jet 50 has a jet stable length 54 that is sufficient for the fluid jet 50 to travel across a nozzle stand-off distance 56 to reach the interface of the lumen of the GI tract and the surface of the GI tract facing the lumen. Ultimately, the fluid (e.g., liquid, suspension) impacts the mucosal layer of the GI tract (e.g., the epithelial layer and any mucus that may be present on the epithelial layer) as a stable stream of fluid with little breakup into a spray and is deposited in the submucosal and/or the mucosal tissue 58. That is, between the nozzle outlet 52 and the site of impact at the mucosa, the jet 50 has a jet diameter 76 that can vary in the manner discussed above with respect to the average jet diameter.

The fluid volume 46 experiences a peak fluid pressure 60 that generates the fluid jet 50 that exits the device 40 with a peak jet velocity, and impacts the interface of the lumen of the GI tract and the surface of the GI tract facing the lumen with a peak jet power, peak jet pressure and peak jet force. One of ordinary skill in the art recognizes that these three parameters are interconnected.

The pressure in the fluid volume 46 decreases during delivery so that the fluid pressure during delivery 70 varies, as does the jet power, jet force, and jet pressure. The fluid pressure during delivery 70 maintains the fluid jet 50 at sufficient jet impact force during delivery to continue fluid (dispensable substance including one or more therapeutic agents) delivery from the fluid volume 46 into the submucosal and/or mucosal tissue 58. The surrounding tissue can then absorb the delivered therapeutic agents for systemic delivery of the therapeutic agent.

Even prior to when the subject swallows the ingestible device, the drive coupling 44 transmits force from the force generator 42 to the fluid volume 46. The drive coupling 44 is prevented from moving by a restraining mechanism 80 (e.g., a pin or plug that selectively degrades and/or selectively erodes) until movement of the drive coupling is triggered by a triggering mechanism, and/or an opening becomes open.

Figure 4:
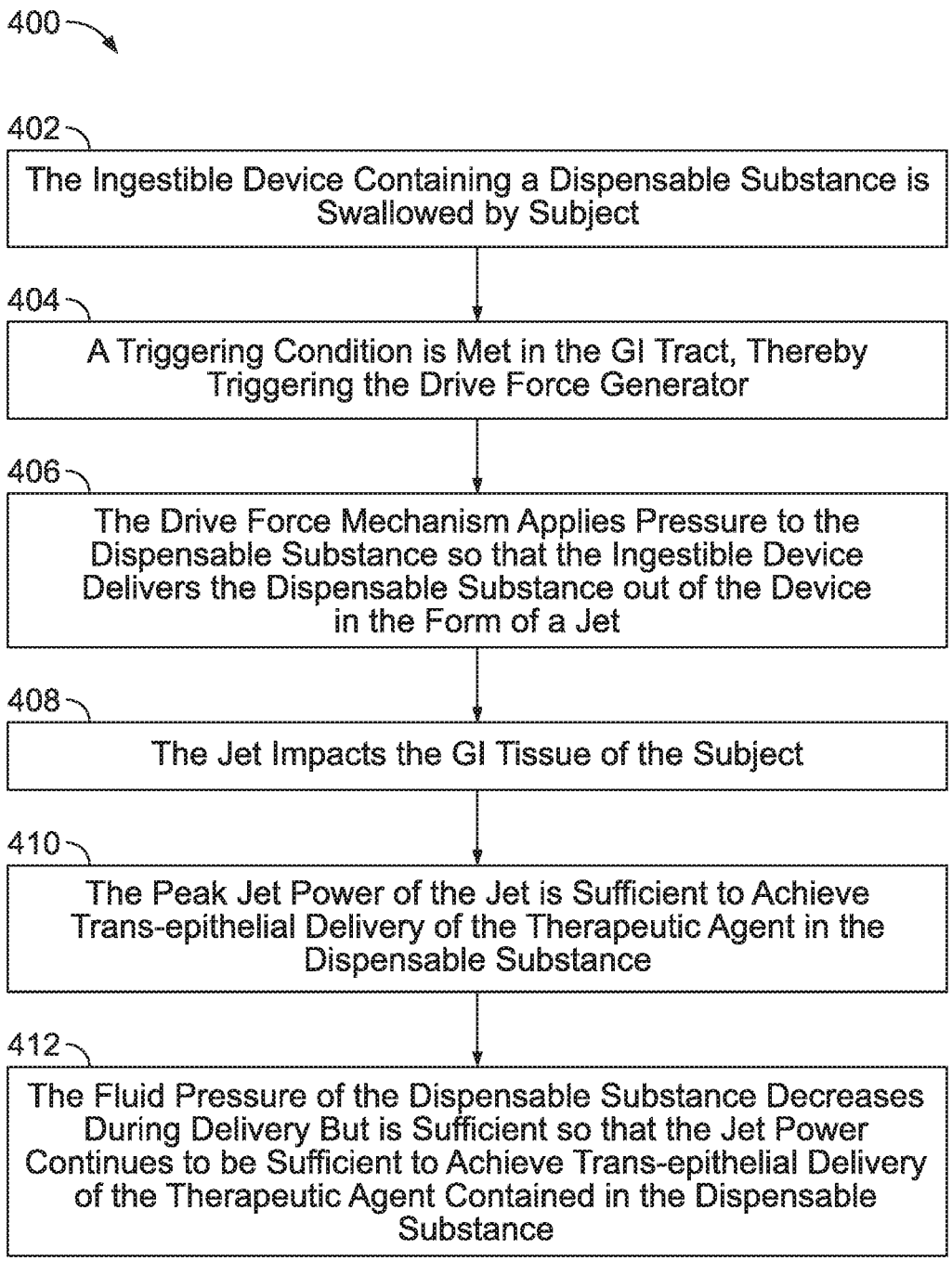
FIG. 4 shows an exemplary process flow chart for use of an ingestible device in which pressure is not applied to the dispensable substance before the subject swallows the ingestible device.

FIG. 4 shows an exemplary process flow chart 400 for use of an ingestible device in which pressure is not applied to the dispensable substance before the subject swallows the ingestible device. The process beings at step 402, when the patient swallows the ingestible device. In step 404, a triggering condition (e.g., pH, change in pH, presence of certain enzyme, concentration of certain enzyme) is met in the GI tract, thereby triggering the drive force generator. In step 406, the drive force mechanism applies pressure to the dispensable substance, resulting delivery of a jet of the dispensable substance from the ingestible device for each opening. In step 408, the jet has a sufficient jet stable length for the jet to impact the GI tissue of the subject. In step 410, the peak jet power of the jet is sufficient to achieve trans-epithelial delivery of the therapeutic agent contained in the dispensable substance. In step 412, the fluid pressure of the dispensable substance decreases during delivery but is sufficiently so that the peak jet power continues to be sufficient to achieve trans-epithelial delivery of the therapeutic agent contained in the dispensable substance.

Figure 5A:
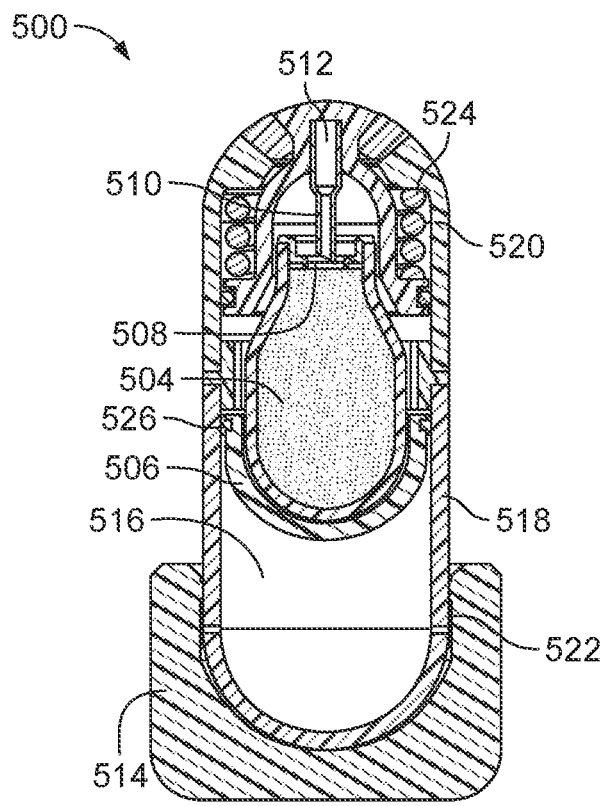
FIGS. 5A-5C show an ingestible device with aspects similar to those shown in FIG. 4.
Figure 5B:
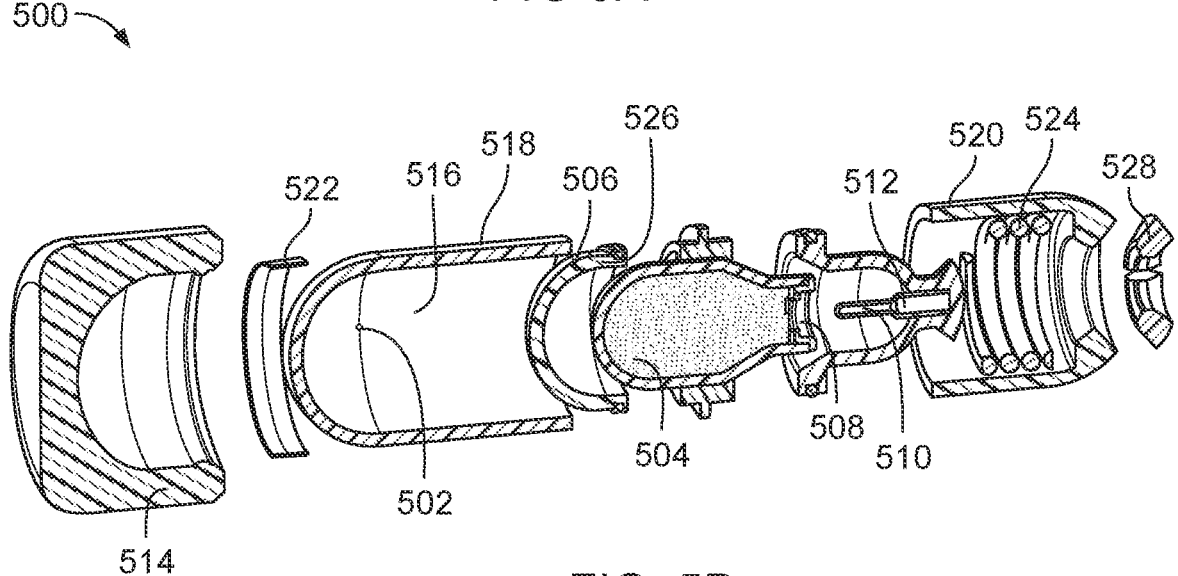
Figure 5C:
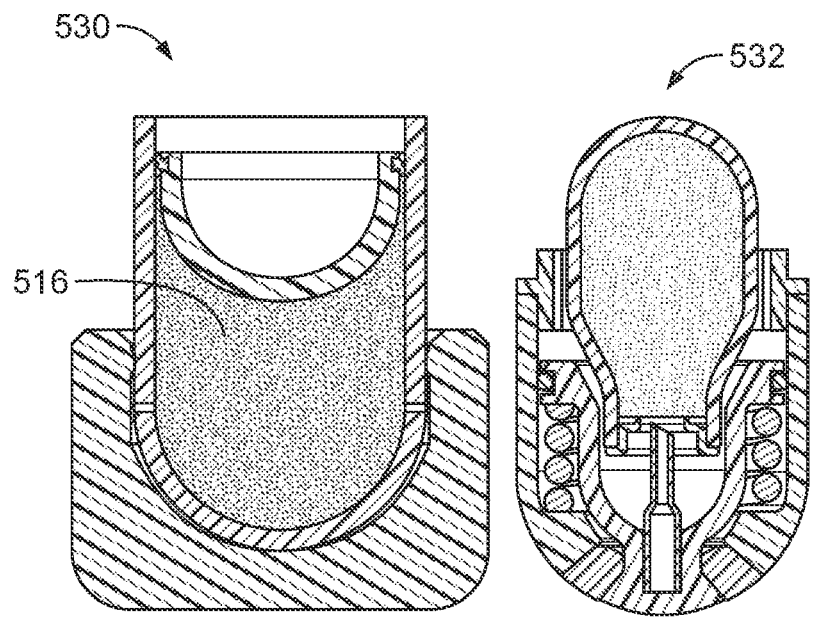

FIGS. 5A-5C show, respectively, a view of an ingestible device 500 as assembled, an exploded of the ingestible device, and aspects of a process of assembly for the ingestible device. Ingestible device 500 includes, a nozzle 502, gas cylinder 504, piston 506, seal 508, pierce pin 510, and piercer 512. A removable cap 514 can be secured over a portion of the ingestible device 500 and removed prior to swallowing. The ingestible device 500 may be used for trans-epithelial delivery. The ingestible device 500 is configured so that a dispensable substance 516 retained within the device that is not under pressure when the subject swallows the ingestible device 500. The ingestible device has two housing parts, a primary container 518 and a secondary container 520. The primary container 518, which includes a fluid volume containing the dispensable substance, can be formed of a cyclic olefin copolymer (COC), such as a molded COC. The primary container 518 includes nozzles 502 with nozzle openings. In some embodiments, the nozzle lengths are about equal to the primary container wall thickness. Exemplary nozzle lengths include about 0.2 mm, about 0.3 mm, about 0.4 mm, about 0.5 mm, about 0.6 mm, about 0.7 mm, about 0.8 mm, about 0.9 mm, and about 1.0 mm. In some embodiments, the nozzle lengths are about 0.7 mm. The ingestible device also includes coverings 522 over the nozzle openings, a spring 524, a gas cylinder 504 having a breakable seal, a piston 506 (e.g., made of a COC), a piercer 512, and an O-ring 526. Nozzle covering 522 can be an integral nozzle cover for gastric protection and can be softened after the ingestible device 500 is ingested, e.g., by gastric fluids, such that the coverings 522 dissolve/degrade and expose the nozzles 502. In some embodiments, O-ring 526 may be lubricated. Similarly, any O-ring disclosed elsewhere herein can optionally be lubricated.

The ingestible device 500 also includes a collar-shaped trigger element 528 which is the triggering mechanism. Although FIG. 5B depicts the trigger element 528 as being collar-shaped, other shapes may be used. In general, the trigger element 528 can have any appropriate shape. Examples of shapes for the trigger element include a complete annulus, an annulus partitioned into two pieces. In some embodiments, the trigger element includes two or more sectors of an annulus with gaps between the sectors. In some embodiments, such a design can increase surface exposure to the environment (e.g., water environment) to promote degradation. For example, FIG. 5C shows a split two-piece collar, e.g., separate assembly modules 530 and 532 which are assembled to form ingestible device 500.

Figure 6A:
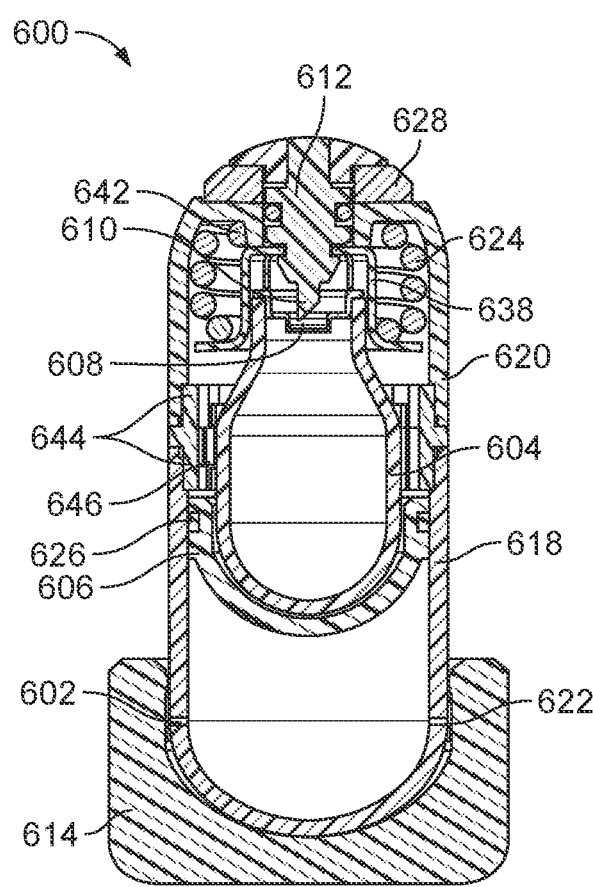
FIGS. 6A-6C shows an ingestible device with aspects similar to those shown in FIGS. 4 and 5.
Figure 6B:
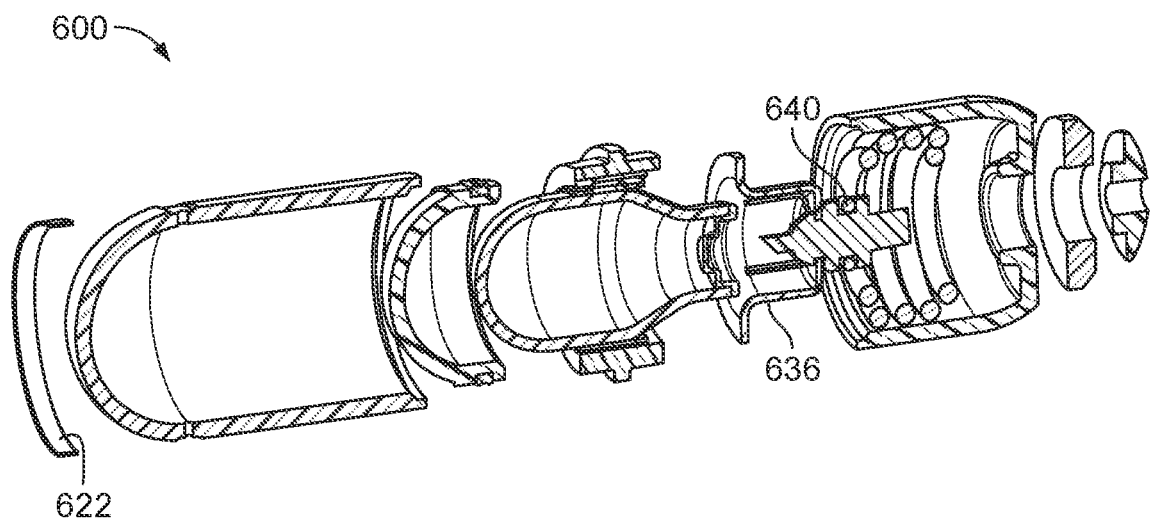
Figure 6C:
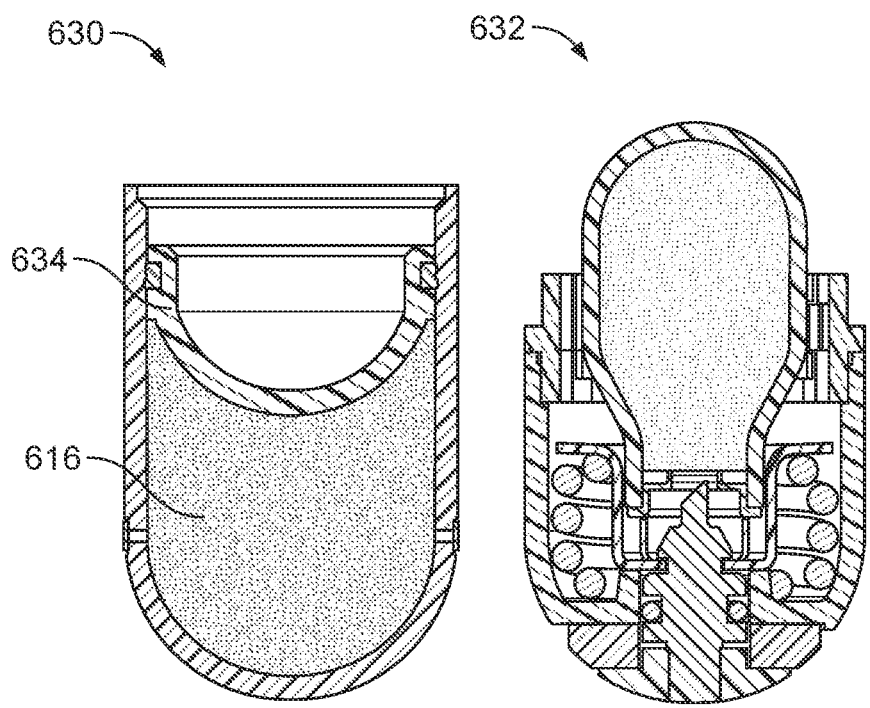
Figure 8:
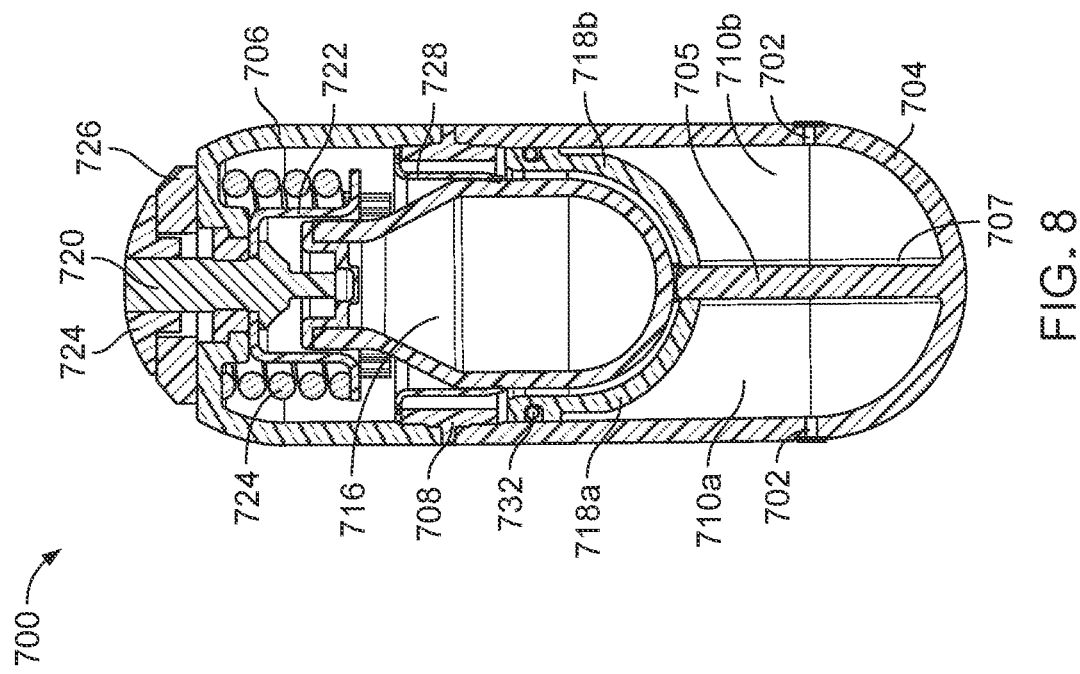
FIGS. 7-13 show an ingestible device having multiple chambers for one or more dispensable substances.
Figure 7:
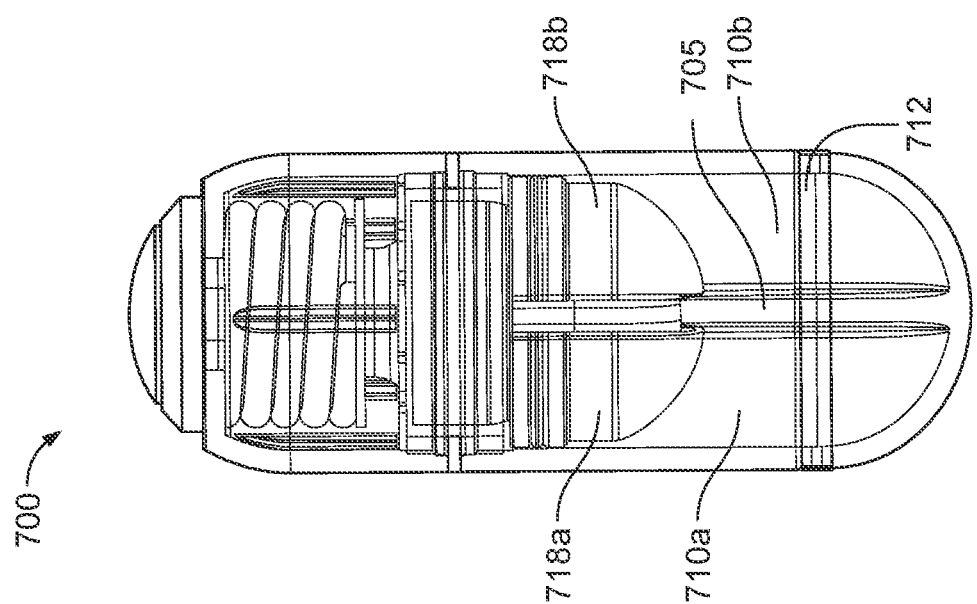
Figure 9:
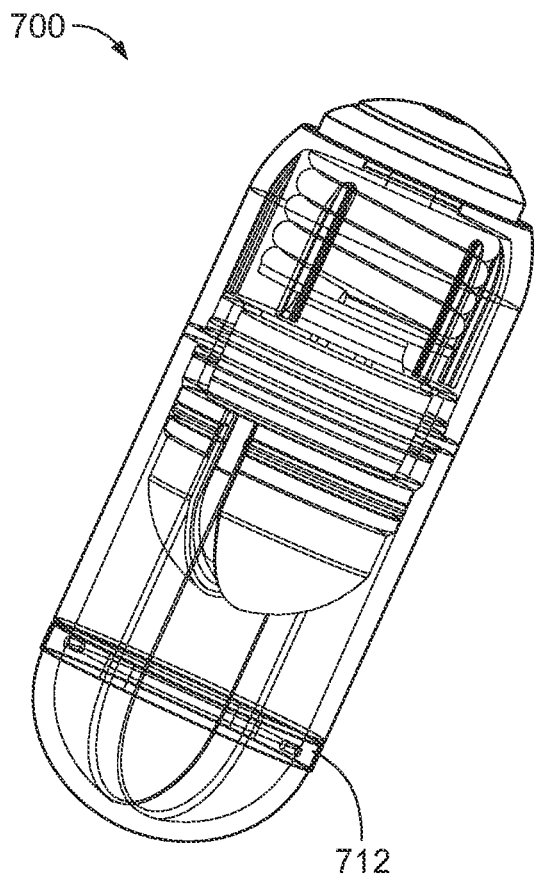
Figure 10:
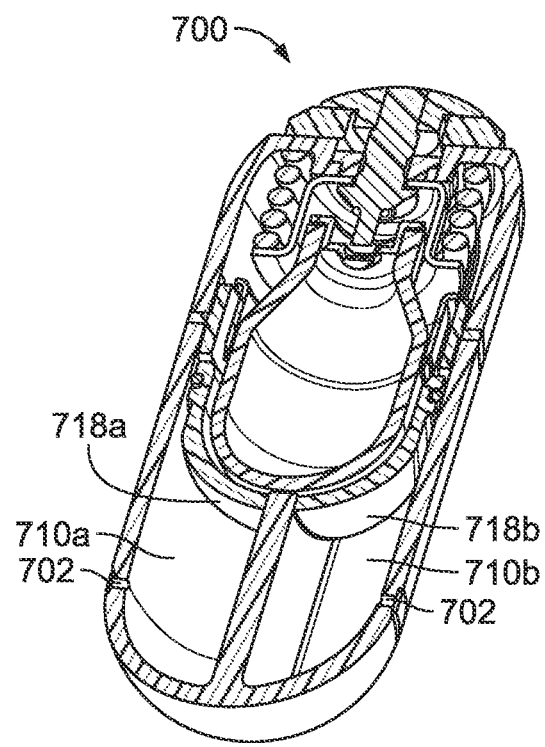
Figure 11:
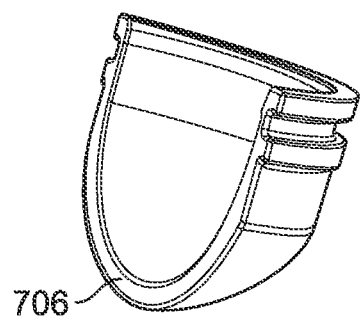
Figure 13:
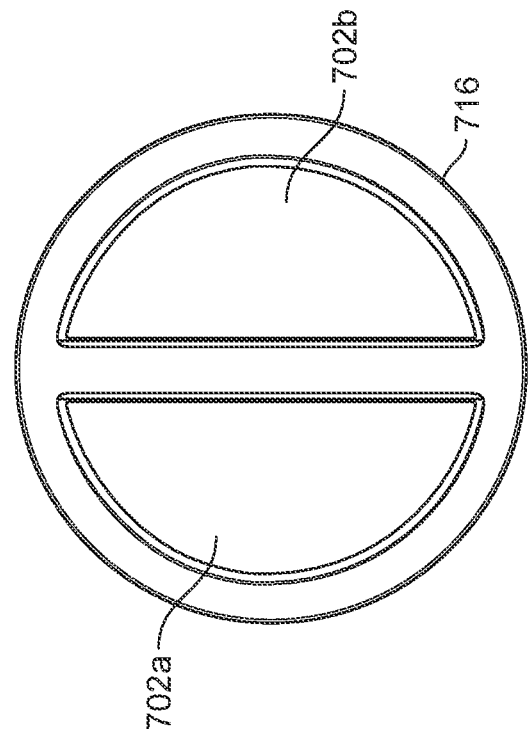
Figure 12:
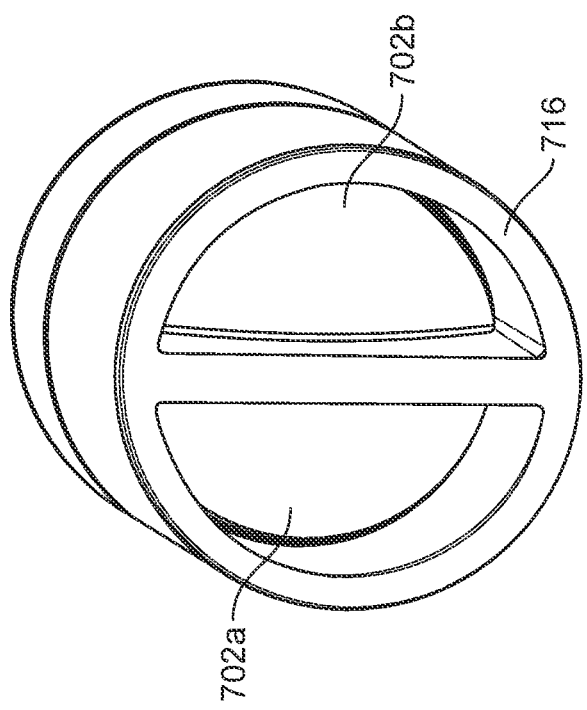

FIGS. 6A-6C, respectively, show view of an ingestible device 600 as assembled, an exploded of the ingestible device 600, and aspects of a process of assembly for the ingestible device 600. The ingestible device 600 may be used for trans-epithelial delivery or for other forms of delivery as appropriate as discussed elsewhere herein. Ingestible device 600 includes, a nozzle 602, gas cylinder 604, piston 606, seal 608, pierce pin 610, and piercer 612. A removable cap 614 can be secured over a portion of the ingestible device 600 and removed prior to swallowing. The ingestible device is configured so that the dispensable substance 616 in the device is not under pressure when the subject swallows the ingestible device. The ingestible device has two housing parts, a primary container 618 and a secondary container 620. The primary container 618, which includes a fluid volume containing the dispensable substance, can be formed of a cyclic olefin copolymer (COC), such as a molded COC, or any other appropriate material as disclosed elsewhere herein. The primary container 618 includes nozzles 602 with nozzle openings. In some embodiments, the nozzle lengths are about equal to the primary container wall thickness. Exemplary nozzle lengths include about 0.3 mm, about 0.4 mm, about 0.5 mm, about 0.6 mm, about 0.7 mm, about 0.8 mm, about 0.9 mm, and about 1.0 mm. In some embodiments, the nozzle lengths are about 0.7 mm. The ingestible device 600 also includes coverings 622 over the nozzle openings, a spring 624, a gas cylinder 604 having a breakable seal 608, a piston 606 (e.g., made of a COC, or another appropriate material), a two-part piercer, and an O-ring 626. The ingestible device also includes a collar-shaped trigger element 628 which is the triggering mechanism, which can be made of any appropriate material as discussed elsewhere herein. Although FIGS. 6A-6C depict the trigger element 628 as being collar-shaped, other shapes may be used, as disclosed elsewhere herein. The device shown in FIGS. 6A-6C has an enhanced piston stabilization length 634 (e.g., about 2 millimeters).

The device shown in FIGS. 6A-6C has a metal spring slider 636, which can enhance space efficiency. The device shown in FIGS. 6A-6C has a piercer slider 638 (e.g., a metal piercer slider) that bottoms out on the spring housing during assembly. This can enhance space efficiency. In the device shown in FIGS. 6A-6C, the two part piercer reduces (e.g., removes) tolerances when manufacturing the trigger element from the piercer clearance with the gas cylinder. In the device shown in FIGS. 6A-6C, the piercer seal 640 (e.g., O-ring) has a relatively small diameter, which can enhance stability and/or reduce resistive pressure build up along its stroke length. In the device shown in FIGS. 6A-6C, the spring 624 has a tapered end coil 642, which can enhance the maximum force potential. In some embodiments, a wave spring may be used. FIGS. 6A-6C shows a gas tight seal 644 (e.g., an ultranonic weld). FIGS. 6A-6C also shows a gas cylinder retention feature 646.

In addition, the ingestible device includes a removable cap 614 which is removed (e.g., by the user) before the ingestible device is swallowed. When the device 600 is swallowed by the subject, the trigger element 628 prevents the dispensable substance 616 in the fluid volume from being under pressure by holding the spring 624 and the piercer 612 in place. When the device reaches the appropriate location in the GI tract, the trigger element 628 at least partially erodes, degrades and/or dissolves (e.g., due to pH, change in pH, presence of certain enzyme, and/or concentration of certain enzyme), and the trigger element 628 is no longer sufficient to hold back the pressure from the spring 624. In some embodiments, the trigger element 628 at least partially erodes, degrades and/or dissolves in the presence of water. In such embodiments, the trigger element may include a covering of a thin film of material that preferentially degrades due to, for example, a change in pH and/or presence of enzyme. The spring 624 forces the pierce pin 610 of piercer 612 into the breakable seal 608, causing the breakable seal to break. This causes gas at elevated pressure to leave the cylinder 604, causing an elevated pressure to bear against the piston 606 and apply pressure to the fluid volume 616. This causes the coverings 622 of the nozzle openings, which are made of a relatively low mechanical strength material (e.g., a foil or a film), to break so that the dispensable substance is delivered out of the nozzle openings in the form of a jet. In certain embodiments, the covering 622 of the nozzle openings are made of a material that erodes, degrades and/or dissolves in the presence of, for example water or elevated pH (e.g., an enteric band or band of water soluble polymer material). The coverings may be partially or completely displaced from the capsule at the time the trigger element actuates. This results in in trans-epithelial delivery of the therapeutic agent contained in the dispensable substance.

FIG. 6C shows aspects of a process for the assembly of the ingestible device, e.g., separate assembly modules 630 and 632 which are assembled to form ingestible device 600. FIG. 6C depicts that the primary container, combined with the cap and nozzle coverings, has the dispensable substance added thereto, followed by adding the piston. This may be done in aseptic environment or other environment appropriate for drug filling and separate from the environment where the mechanical drive assembly is constructed. The other housing part and its components are assembled in a clean environment with the piercer held in place by the trigger element. The gas cylinder 604 is held in place by components of this assembly, including the assembly housing which includes features for locating the gas cylinder in its proper position in the assembled ingestible device. Locating and mounting of the gas cylinder may be aided by the formation of a mounting feature integral to the gas cylinder component such as a flange.

FIGS. 7-13 show various views of an ingestible device 700 and/or aspects of the ingestible device 700. As is apparent, the delivery mechanism of the ingestible device 700 is shown as having a design substantially similar to the device shown in FIG. 5, although, more generally, the ingestible device 700 depicted in FIGS. 7-13 can have a delivery mechanism as described elsewhere herein.

Ingestible device 700 includes a gas cylinder 716, a union ring 708, an o-ring 732, an enteric trigger 726, a piercer 720, a spring 724, a spring retention cup 722, a retention element 728, a drug housing 704, a drive housing 706, and a piercer retainer 724. The ingestible device 700 has two chambers 710a, 710b, each containing a dispensable substance. The chambers are separated by a separator 705, such as a rib, which prevents the dispensable substance in one chamber from entering another chamber, e.g., from 710a to 710b and vice versa. In addition, the ingestible device 700 includes a face seal 707 that seals the separator. The ingestible device also has two pistons 718a, 718b, one for each chamber. Each chamber 710a, 710b has at least nozzle 702 for delivering the dispensable substance from the chamber to an exterior of the ingestible device 700. In general, the dispensable substance in one chamber, e.g., chamber 710*a* can be the same as or different from the dispensable substance in the other chamber, e.g., chamber 710*b*. While shown as having two chambers 710*a*, 710*b*, the disclosure is not limited in this sense. More generally, the ingestible device 700 can have as many chambers as desired (e.g., two chambers, three chambers, four chambers, five chambers, six chambers, seven chambers, eight chambers, nine chambers, 10 chambers, more than 10 chambers). In general, each chamber 710*a*, 710*b* will have a corresponding piston 718*a*, 718*b*, and there will be a separator 705 between adjacent chambers. In some embodiments, each chamber has the same internal volume. In certain embodiments, different chambers can have different volumes. Combinations of such embodiments are also possible.

In some embodiments the disclosure provides an ingestible device that includes an element 712 (e.g., covering) having a first state in which the element 712 at least partially covers the nozzle opening of nozzle 702 in the housing 704 and a second state in which the element 712 does not cover the nozzle opening in the housing 704, where the ingestible device 700 is configured so that, when the drive force coupling (e.g., piston 718*a*, 718*b*) moves, the element 712 moves from its first state to its second state. In certain embodiments, the element 712 conforms to an inner radius of the housing 704, is flexible and/or includes a cylindrical portion. In some embodiments, the element 712 is removable from the ingestible device 700 (e.g., when the element 712 is in its second state, the element 712 is removed from the ingestible device). Such a removable element 712 can be, for example, a cap. Optionally, the element 712 moves can move synchronously with the drive force coupling, e.g., pistons 718*a*, 718*b*. In some embodiments, when the drive force coupling moves a distance, the element 712 moves the same distance. The ingestible device can include a seal 718 (e.g., an O-ring) that mechanically coupled (e.g., sealed) with the drive force coupling and element 712. With this arrangement, the seal 718 can be configured to cause the movement of the drive force coupling to result in the movement of the element 712.

Figure 14:
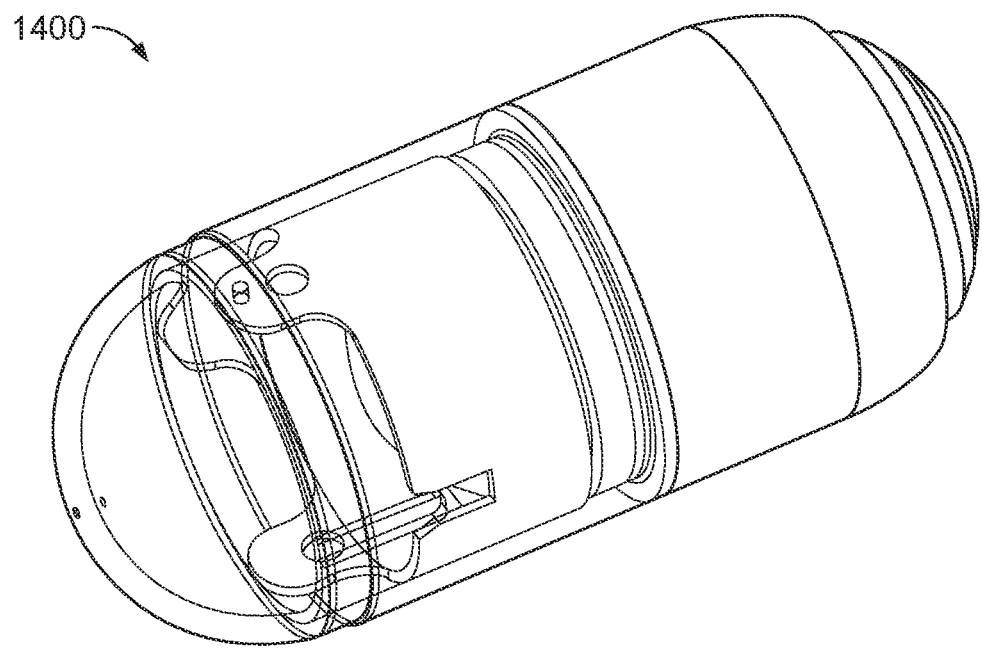
FIGS. 14-17 show an ingestible device.
Figure 15:
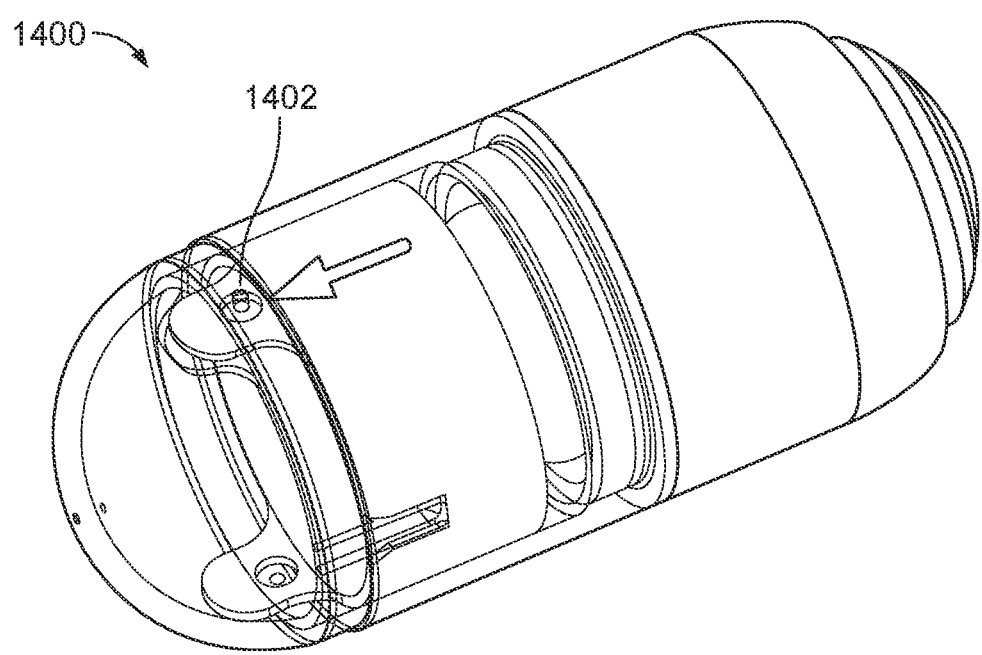

FIGS. 14-18 show an ingestible device 1400 which contains a dispensable substance that is not under pressure when the subject swallows the ingestible device. In FIG. 14, the jet opening 1402 is depicted is covered, and in FIG. 15 the jet opening 1402 is uncovered.

Figure 16:
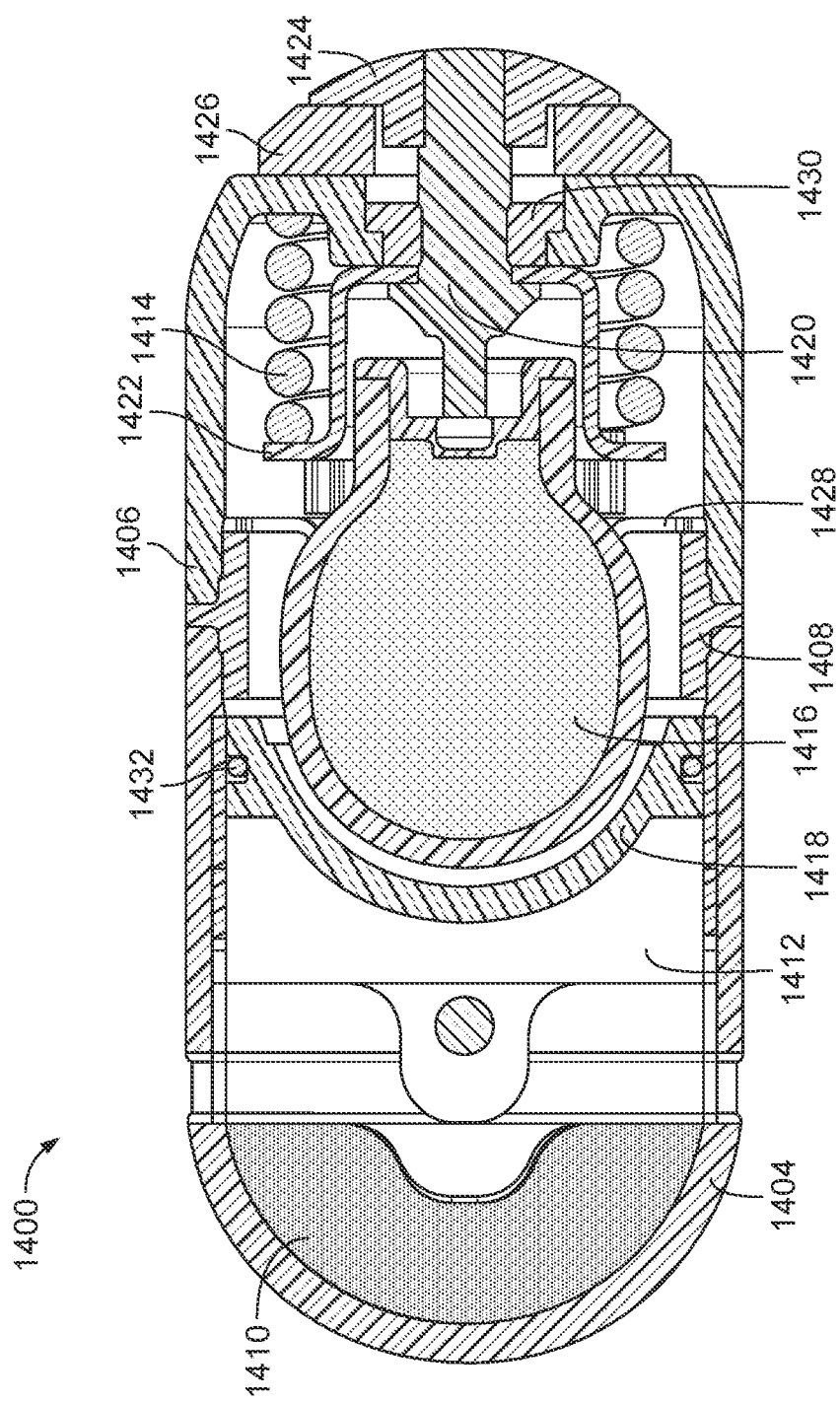
Figure 17:
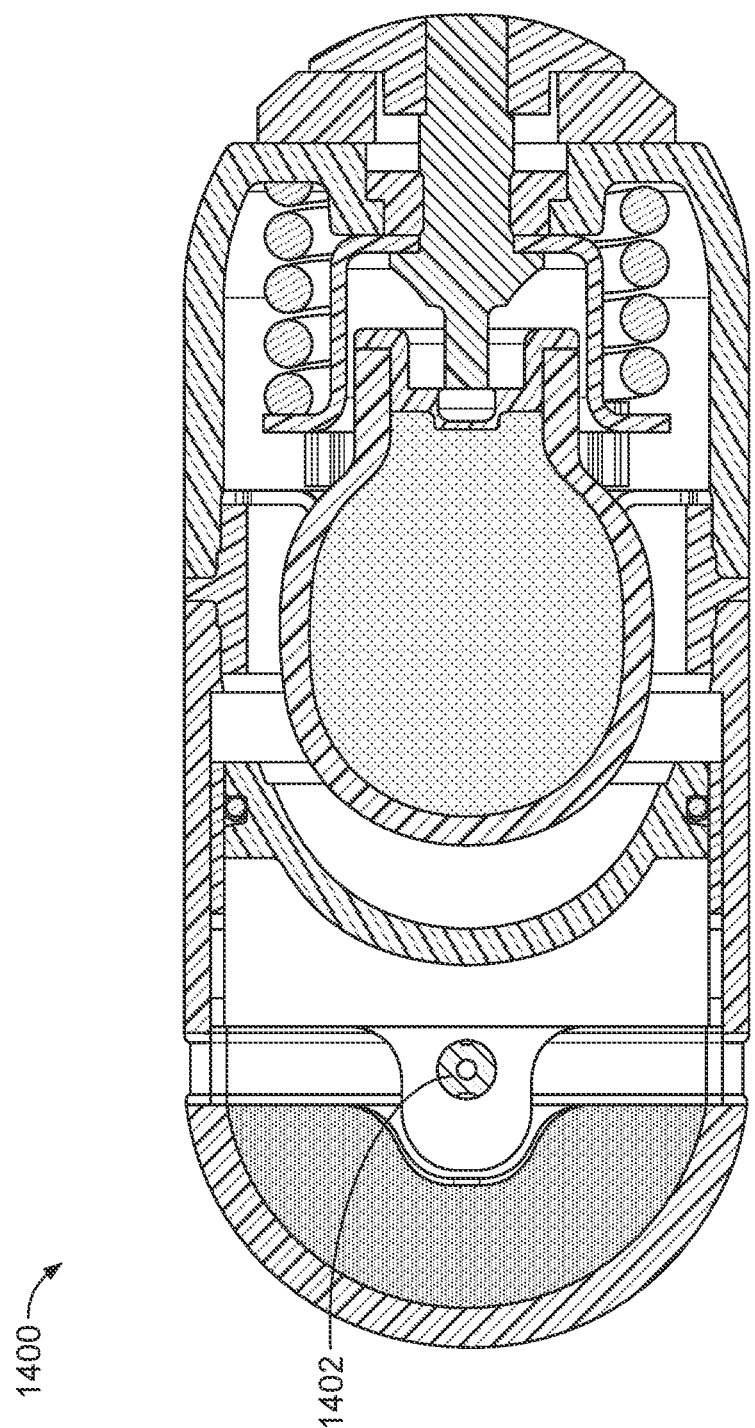

FIGS. 16 and 17 show the ingestible device 1400 in more detail. The ingestible device 1400 has housing parts 1404 and 1406 connected by a union ring 1408 and with a fluid volume 1410 containing a dispensable substance, opening 1402, and a jet covering 1412, e.g., a cylindrical sleeve made of a flexible material which is able to conform to an inside radius of the housing 1406 which slides to open or seal the opening 1402, a spring 1414, a gas cylinder 1416, a piston 1418, a piercer 1420, and an O-ring 1432. Gas cylinder 1416 is retained by retention element 1428. A seal 1430 forms a gas seal between the piercer 1420 and the housing 1404. A spring retention cup 1422 retains the spring-loaded piercer 1420. A piercer retainer 1424 holds the piercer 1420 in place with an enteric trigger 1426 that retains the piercer retainer in place until it dissolves and used as the triggering mechanism. When the device 1400 is swallowed by the subject, the enteric trigger 1426 prevents the dispensable substance in fluid volume 1410 from being under pressure by holding the spring 1414 and the piercer 1420 in place. When the device 1400 reaches the appropriate location in the GI tract, the enteric trigger 1426 degrades and/or dissolves (e.g., due to pH, change in pH, presence of certain enzyme, and/or concentration of certain enzyme) that the pierce pin retainer 1424 is no longer sufficient to hold back the pressure from the spring 1414. The spring 1414 forces the piercer 1420 into the gas cylinder 1416, puncturing the gas cylinder 1416 and causing gas at elevated pressure to leave the cylinder 1416. This causes the gas cylinder 1416 to press against the piston 1418 and apply pressure to the fluid volume 1410. The piston provides friction to slide the jet covering 1412 open exposing the jet openings 1402 such that the dispensable substance is delivered out of the jet opening 1402 in the form of a jet. This results in trans-epithelial delivery of the therapeutic agent contained in the dispensable substance. FIG. 17 shows the embodiment of the ingestible device 1400 in which the jet covering 1412 is slide open to expose the jet openings 1402.

Typically, the ingestible device 1400 is used in trans-epithelial delivery. However, the ingestible device 1400 may be used for either epithelial delivery or topical delivery. Appropriate parameters for the different types of delivery are provided elsewhere herein.

Figure 18:
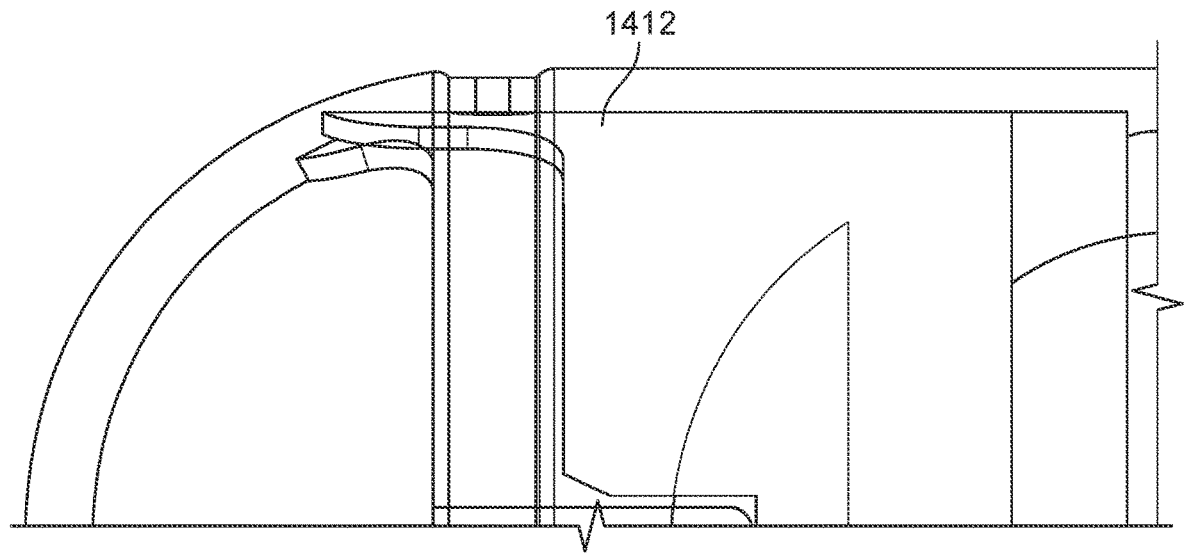
FIG. 18 shows certain elements of an ingestible device of FIG. 19V.

In some embodiments, the housing of the ingestible device 1400 has a diameter from about 9.5 mm to about 10.5 mm (e.g., from about 9.8 mm to about 10 mm), a length from about 23 mm to about 26.5 mm (e.g., from about 23.3 mm to about 26.1 mm), a wall thickness from about 0.4 mm to about 0.6 mm (e.g., about 0.5 mm), a fluid volume from about 425 µL to about 600 µL (e.g., from about 450 µL to about 585 µL), and/or a gas volume in the gas cylinder 1416 from about 150 µL to about 175 µL (e.g., about 160 µL). FIG. 18 shows the ingestible device 1400 where the jet covering 1412 conforms along a radius of the ingestible device 1400.

Figure 19:
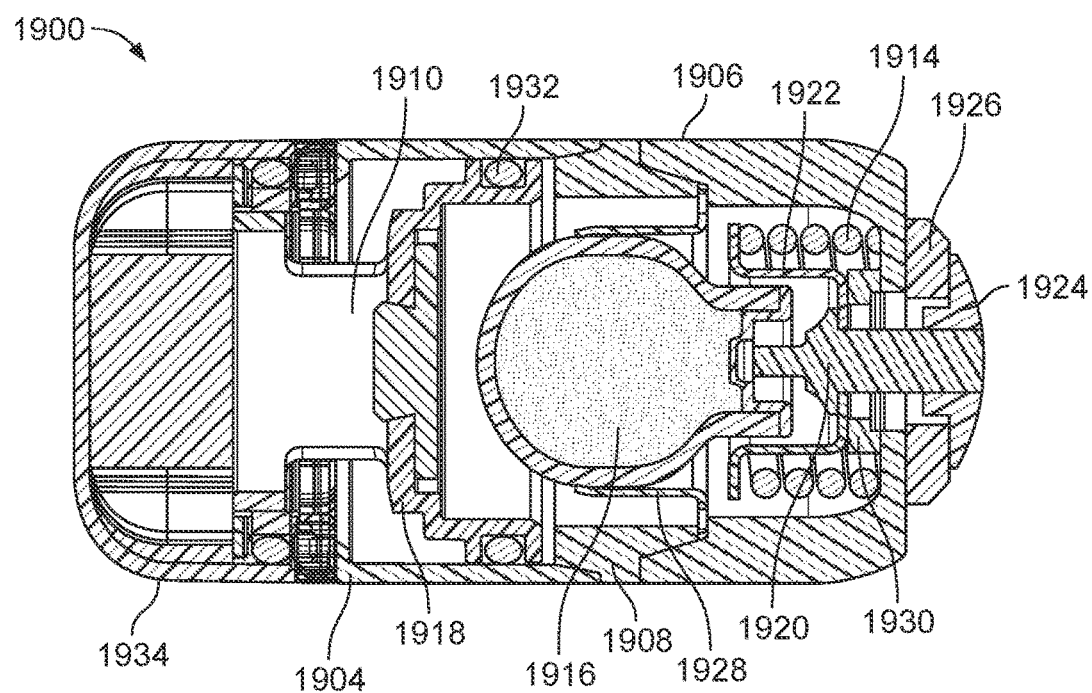
FIGS. 19 and 20 show states of an ingestible device.
Figure 20:
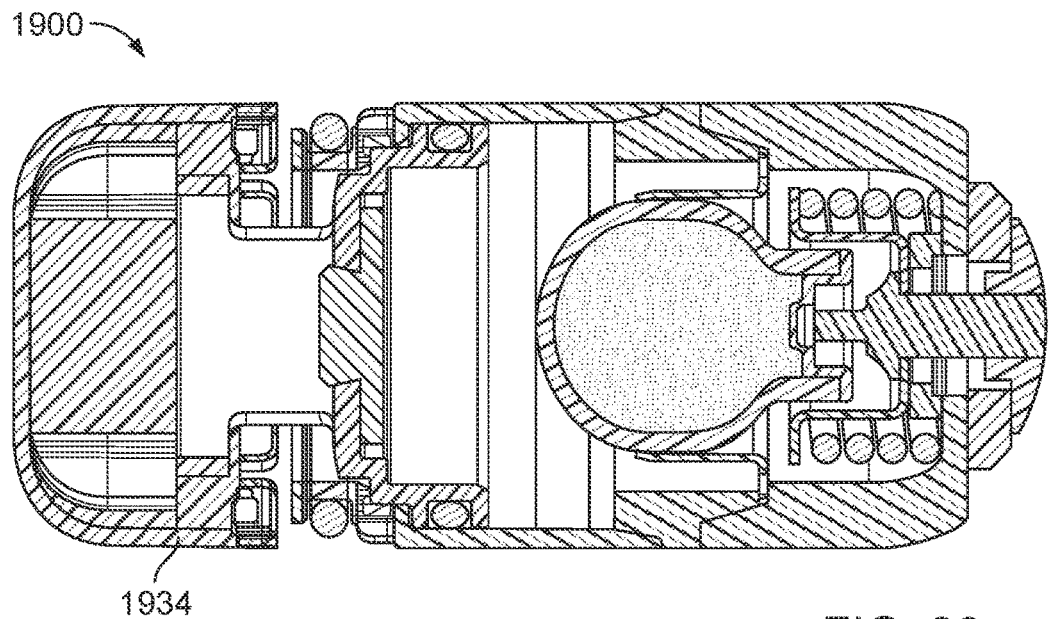

FIGS. 19 and 20 show an ingestible device 1900 in its closed and open states, respectively. The ingestible device 1900 contains a dispensable substance that is not under pressure when the subject swallows the ingestible device. The ingestible device 1900 has housing parts 1904 and 1906 connected by a union ring 1908 and with a fluid volume 1910 containing a dispensable substance, a spring 1914, a gas cylinder 1916, a piston 1918, a piercer 1920, and an O-ring 1932. Gas cylinder 1916 is retained by retention element 1928. A seal 1930 forms a gas seal between the piercer 1920 and the housing 1906. A spring retention cup 1922 retains the spring-loaded piercer 1920. A piercer retainer 1924 holds the piercer 1920 in place with an enteric trigger 1926 that retains the piercer retainer in place until it dissolves and used as the triggering mechanism. When the device 1900 is swallowed by the subject, the enteric trigger 1926 prevents the dispensable substance in fluid volume 1910 from being under pressure by holding the spring 1914 and the piercer 1920 in place. When the device 1900 reaches the appropriate location in the GI tract, the enteric trigger 1926 degrades and/or dissolves (e.g., due to pH, change in pH, presence of certain enzyme, and/or concentration of certain enzyme) that the piercer retainer 1924 is no longer sufficient to hold back the pressure from the spring 1914. The spring 1914 forces the piercer 1920 into the gas cylinder 1916, puncturing the gas cylinder 1916 and causing gas at elevated pressure to leave the cylinder 1916. This causes the gas cylinder 1916 to press against the piston 1918 and apply pressure to the fluid volume 1910. The piston provides friction to cause the cap 1934 to open/deploy such that the dispensable substance is delivered out of the volume 1910. This results in release of the therapeutic agent into the GI tract of the subject.

In some embodiments, the housing of the ingestible device 1900 has a diameter from about 10 mm to about 12 mm (e.g., from about 11.3 mm to about 11.5 mm), a length from about 23 mm to about 26.5 mm (e.g., from about 23.3 mm to about 26.3 mm), a wall thickness from about 0.4 mm to about 0.6 mm (e.g., about 0.5 mm), a fluid volume from about 565 µL to about 630 µL (e.g., from about 574 µL to about 623 µL), and/or a gas volume in the gas cylinder 1916 from about 150 µL to about 175 µL (e.g., about 160 µL).

In general, the ingestible device 1900 is used in topical delivery.

Figure 21:
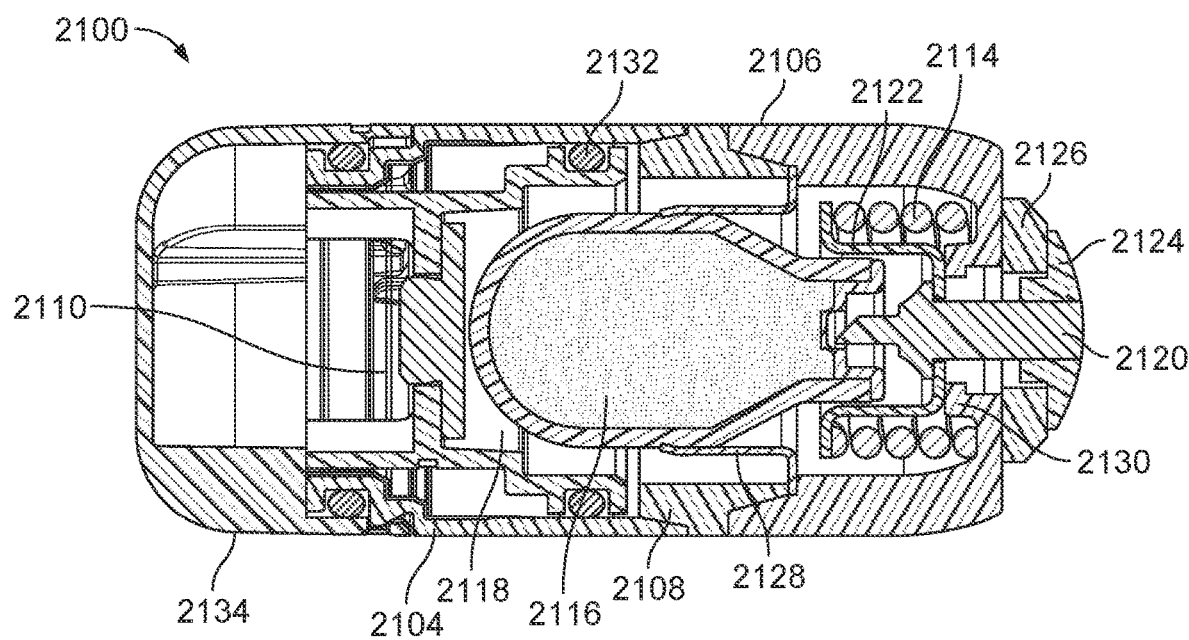
FIGS. 21 and 22 show states of an ingestible device.
Figure 22:
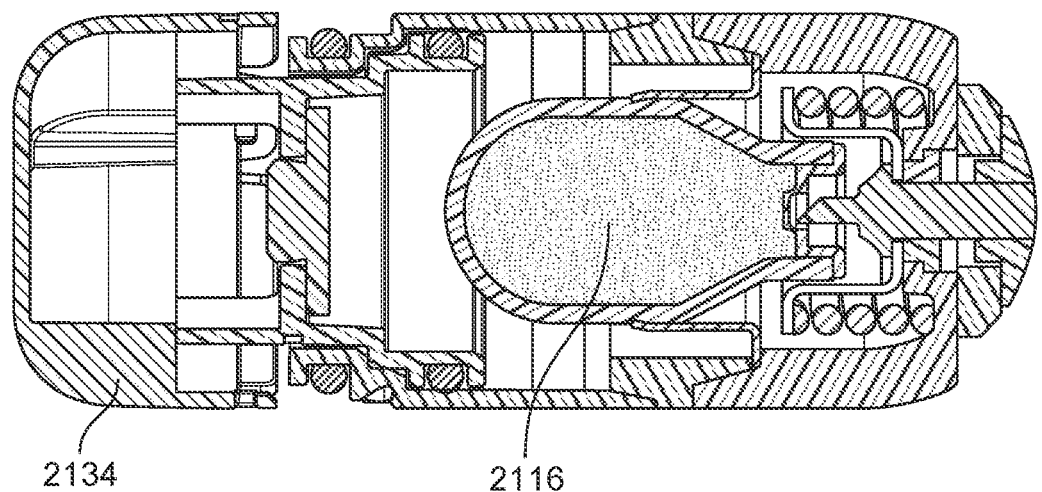

FIGS. 21 and 22 show an ingestible device 2100 in its closed and open states, respectively. The ingestible device 2100 contains a dispensable substance that is not under pressure when the subject swallows the ingestible device. The ingestible device 2100 has housing parts 2104 and 2106 connected by a union ring 2108 and with a fluid volume 2110 containing a dispensable substance, a spring 2114, a gas cylinder 2116, a piston 2118, a piercer 2120, and an O-ring 2132. Gas cylinder 2116 is retained by retention element 2128. A seal 2130 forms a gas seal between the piercer 2120 and the housing 2106. A spring retention cup 2122 retains the spring-loaded piercer 2120. A piercer retainer 2124 holds the piercer 2120 in place with an enteric trigger 2126 that retains the piercer retainer in place until it dissolves and used as the triggering mechanism. When the device 2100 is swallowed by the subject, the enteric trigger 2126 prevents the dispensable substance in fluid volume 2110 from being under pressure by holding the spring 2114 and the piercer 2120 in place. When the device 2100 reaches the appropriate location in the GI tract, the enteric trigger 2126 degrades and/or dissolves (e.g., due to pH, change in pH, presence of certain enzyme, and/or concentration of certain enzyme) that the piercer retainer 2124 is no longer sufficient to hold back the pressure from the spring 2114. The spring 2114 forces the piercer 2120 into the gas cylinder 2116, puncturing the gas cylinder 2116 and causing gas at elevated pressure to leave the cylinder 2116. This causes the gas cylinder 2116 to press against the piston 2118 and apply pressure to the fluid volume 2110. The piston provides friction to cause the cap 2134 to open/deploy such that the dispensable substance is delivered out of the volume 2110. This results in delivery (e.g., topical delivery) of the therapeutic agent contained in the dispensable substance.

In some embodiments, the housing of the ingestible device 2100 has a diameter from about 10 mm to about 12 mm (e.g., from about 11.3 mm to about 11.5 mm), a length from about 23 mm to about 26.5 mm (e.g., from about 23.3 mm to about 26.3 mm), a wall thickness from about 0.4 mm to about 0.6 mm (e.g., about 0.5 mm), a fluid volume from about 565 µL to about 630 µL (e.g., from about 574 µL to about 623 µL), and/or a gas volume in the gas cylinder 2116 from about 150 µL to about 175 µL (e.g., about 160 µL).

Figure 23:
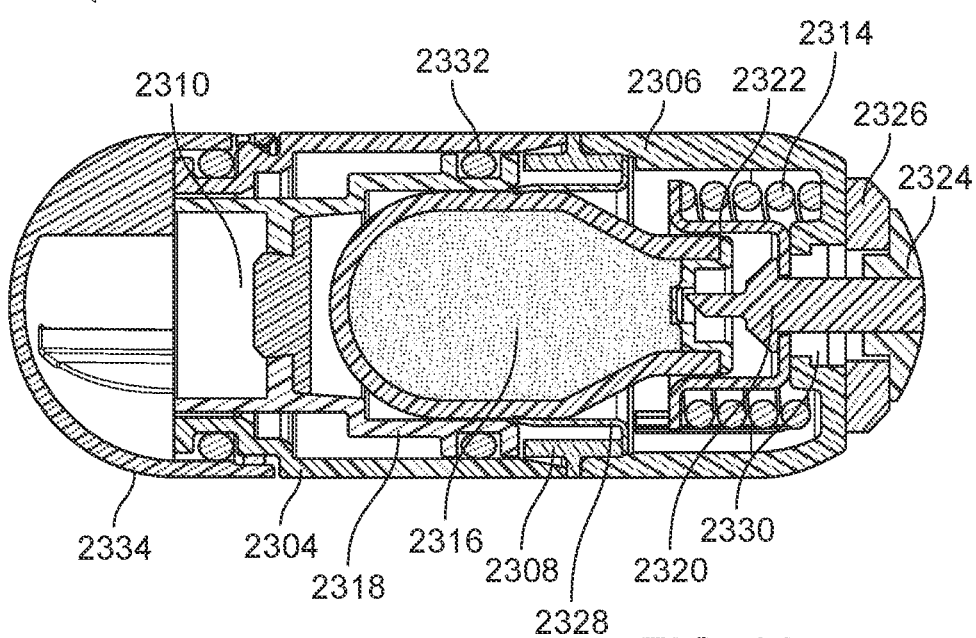
FIGS. 23 and 24 show states of an ingestible device.
Figure 24:
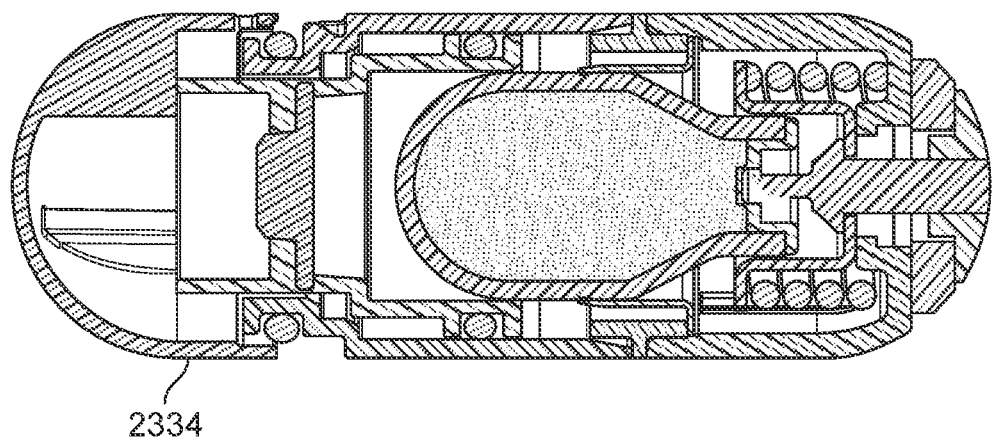

FIGS. 23 and 24 show an ingestible device 2300 in its closed and open states, respectively. The ingestible device 2300 contains a dispensable substance that is not under pressure when the subject swallows the ingestible device. The ingestible device 2300 has housing parts 2304 and 2306 connected by a union ring 2308 and with a fluid volume 2310 containing a dispensable substance, a spring 2314, a gas cylinder 2316, a piston 2318, a piercer 2320, and an O-ring 2332. Gas cylinder 2316 is retained by retention element 2328. A seal 2330 forms a gas seal between the piercer 2320 and the housing 2306. A spring retention cup 2322 retains the spring-loaded piercer 2320. A piercer retainer 2324 holds the piercer 2320 in place with an enteric trigger 2326 that retains the piercer retainer in place until it dissolves and used as the triggering mechanism. When the device 2300 is swallowed by the subject, the enteric trigger 2326 prevents the dispensable substance in fluid volume 2310 from being under pressure by holding the spring 2314 and the piercer 2320 in place. When the device 2300 reaches the appropriate location in the GI tract, the enteric trigger 2326 degrades and/or dissolves (e.g., due to pH, change in pH, presence of certain enzyme, and/or concentration of certain enzyme) that the piercer retainer 2324 is no longer sufficient to hold back the pressure from the spring 2314. The spring 2314 forces the piercer 2320 into the gas cylinder 2316, puncturing the gas cylinder 2316 and causing gas at elevated pressure to leave the cylinder 2316. This causes the gas cylinder 2316 to press against the piston 2318 and apply pressure to the fluid volume 2310. The piston provides friction to cause the cap 2334 to open/deploy such that the dispensable substance is delivered out of the volume 2310. This results in delivery (e.g., topical delivery) of the therapeutic agent contained in the dispensable substance.

In some embodiments, the housing of the ingestible device 2300 has a diameter from about 8 mm to about 11 mm (e.g., from about 9.8 mm to about 10 mm), a length from about 23 mm to about 26.5 mm (e.g., from about 23.3 mm to about 26.3 mm), a wall thickness from about 0.4 mm to about 0.6 mm (e.g., about 0.5 mm), a fluid volume from about 230 µL to about 355 µL (e.g., from about 235 µL to about 349 µL), and/or a gas volume in the gas cylinder 2316 from about 150 µL to about 175 µL (e.g., about 160 µL).

Figure 25:
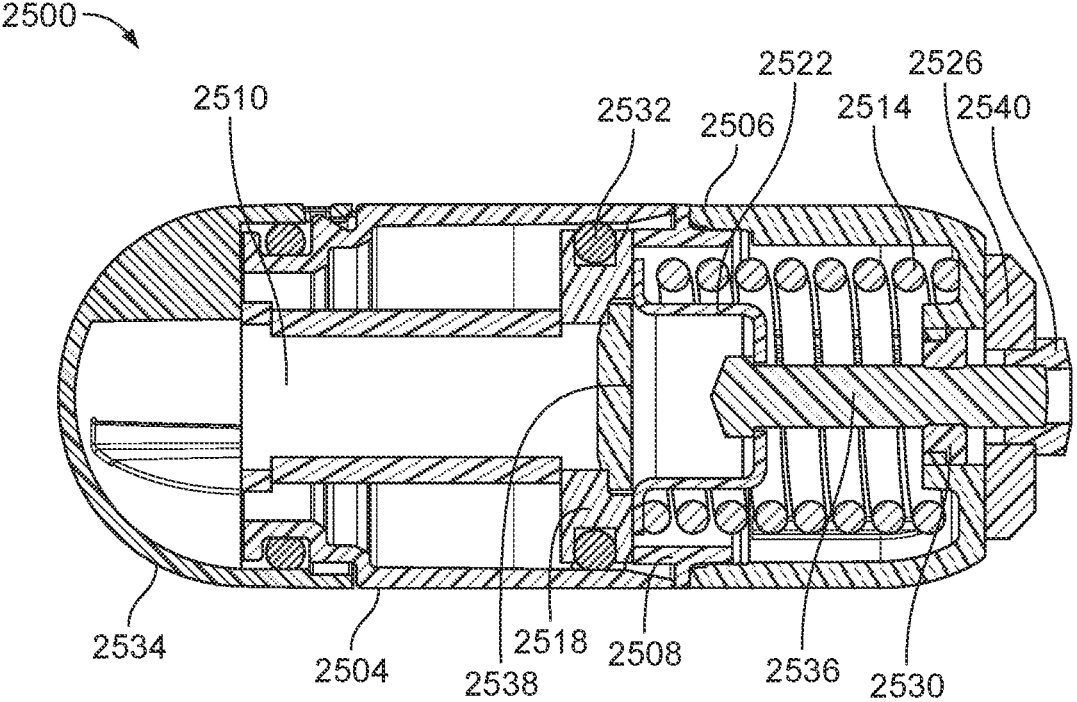
FIGS. 25-27 show ingestible devices.

FIG. 25 shows an embodiment of an ingestible device 2500, which contains a dispensable substance that is not under pressure when the subject swallows the ingestible device. The ingestible device 2500 has housing parts 2504 and 2506 connected by a union ring 2508 and with a fluid volume 2510 containing a dispensable substance, a spring 2514, a piston 2518, a spring retention pin 2536, and an O-ring 2532. A dispensable substance-containing cap 2538 seals in the dispensable substance (e.g., drug-containing liquid) after the housing part 2504 is filled with the dispensable substance (e.g., drug-containing liquid). A seal 2530 forms a gas seal between the spring retention pin 2536 and the housing part 2506. A spring retention cup 2522 retains the spring retention pin 2536. A pin retainer 2540 holds the spring retention pin 2536 in place with an enteric trigger 2526 that retains the pin retainer in place until it dissolves and used as the triggering mechanism. When the device 2500 is swallowed by the subject, the enteric trigger 2526 prevents the dispensable substance in fluid volume 2510 from being under pressure by holding the spring 2514 and the spring retention pin 2536 in place. When the device 2500 reaches the appropriate location in the GI tract, the enteric trigger 2526 degrades and/or dissolves (e.g., due to pH, change in pH, presence of certain enzyme, and/or concentration of certain enzyme) that the pin retainer 2540 is no longer sufficient to hold back the spring retention pin 2536, releasing spring 2514. The spring 2514 pushes against the piston 2518 such that the piston 2518 applies pressure to the fluid volume 2510. The piston provides friction to cause the cap 2534 to open/deploy such that the dispensable substance is delivered out of the volume 2510. This results in delivery (e.g., topical delivery) of the therapeutic agent out of the dispensable substance.

In some embodiments, the housing of the ingestible device 2500 has a diameter from about 8 mm to about 11 mm (e.g., from about 9.8 mm to about 10 mm), a length from about 23 mm to about 26.5 mm (e.g., from about 23.3 mm to about 26.1 mm), a wall thickness from about 0.4 mm to about 0.6 mm (e.g., about 0.5 mm), a fluid volume from about 395 µL to about 570 µL (e.g., from about 403 µL to about 559 µL).

Figure 26:
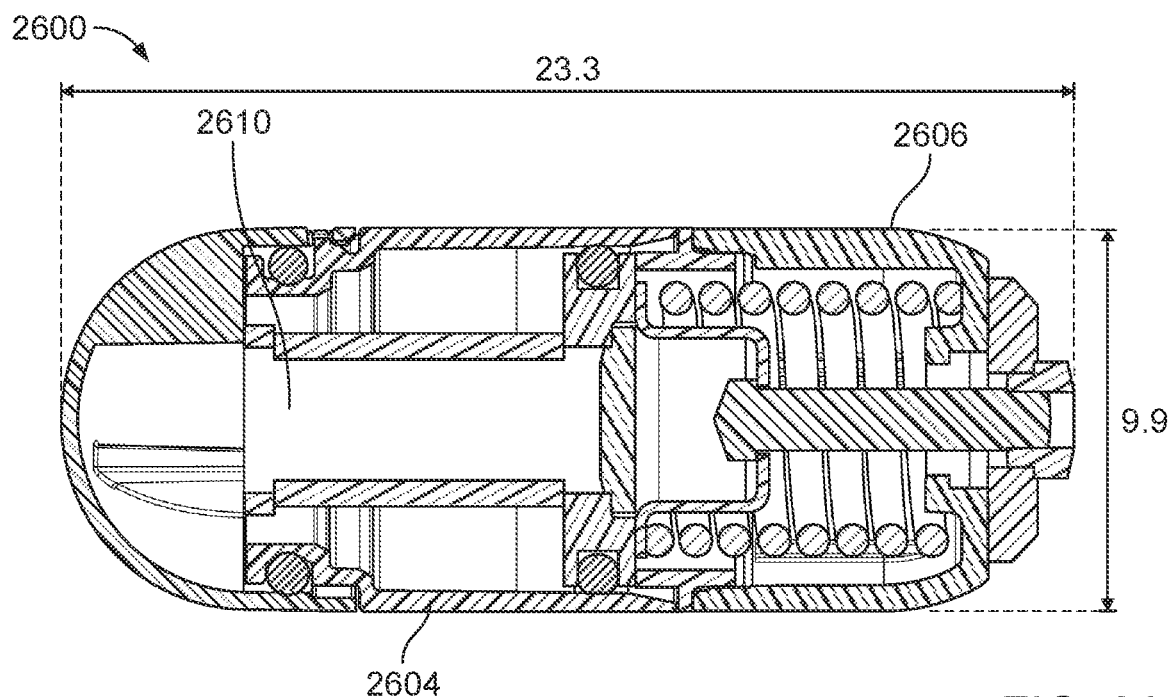
Figure 27:
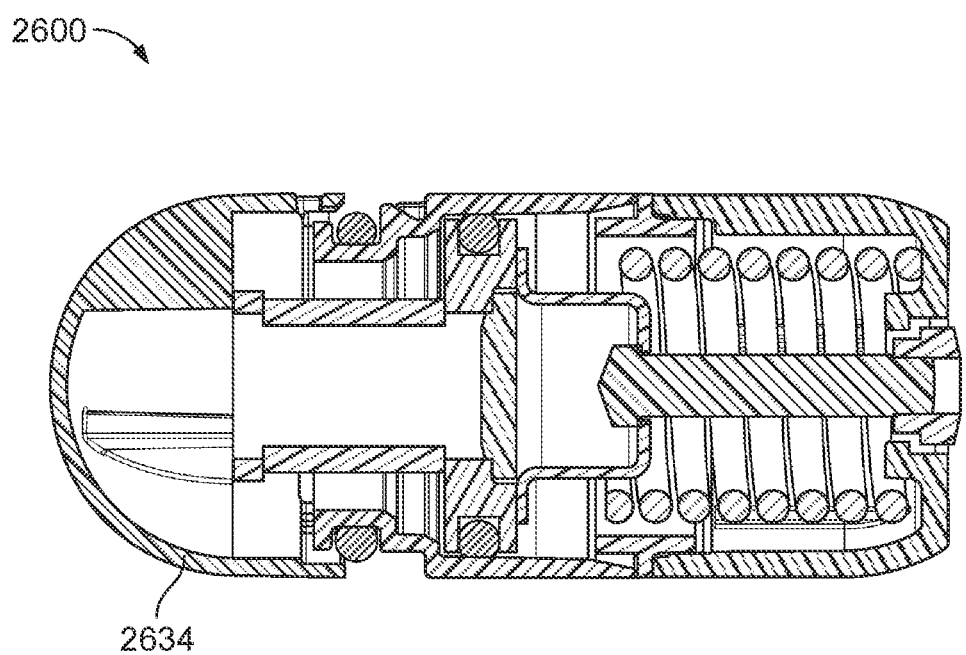

FIGS. 26 and 27 show an ingestible device 2600 in its closed and open states, respectively. The ingestible device 2600 is configured similarly to ingestible device 2500 and having housing components 2604 and 2606 with a smaller profile than the housing component of ingestible device 2500. Fluid volume 2610 of ingestible device 2600 can have a smaller capacity than fluid volume 2510 of ingestible device 2500.

In some embodiments, the housing of the ingestible device 2600 has a diameter from about 8 mm to about 11 mm (e.g., from about 9.8 mm to about 10 mm), a length from about 23 mm to about 26.5 mm (e.g., from about 23.3 mm to about 26.1 mm), a wall thickness from about 0.4 mm to about 0.6 mm (e.g., about 0.5 mm), a fluid volume from about 395 µL to about 570 µL (e.g., from about 403 µL to about 559 µL).

Figure 28:
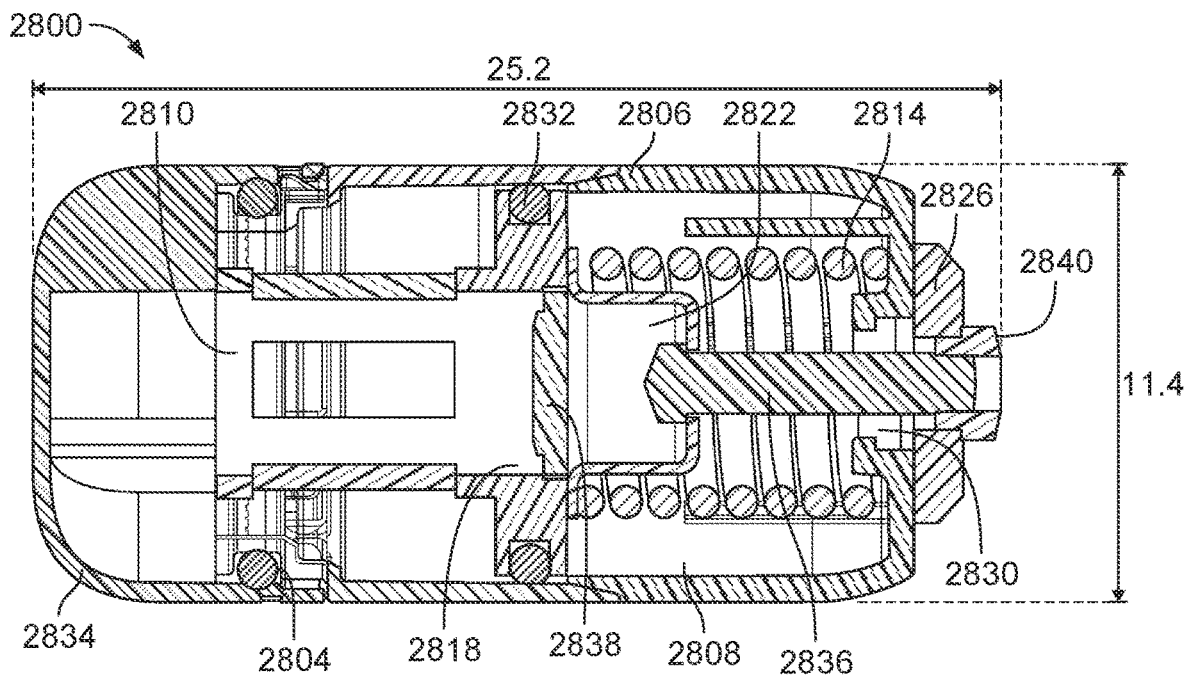
FIGS. 28-30 show states of an ingestible device.

FIG. 28 shows an embodiment of an ingestible device 2800, which contains a dispensable substance that is not under pressure when the subject swallows the ingestible device. The ingestible device 2800 has housing parts 2804 and 2806 connected by a union ring 2808 and with a fluid volume 2810 containing a dispensable substance, a spring 2814, a piston 2818, a spring retention pin 2836, and an O-ring 2832. A dispensable substance-containing cap 2838 seals in the dispensable substance (e.g., drug-containing liquid) after the housing part 2804 is filled with the dispensable substance (e.g., drug-containing liquid). A seal 2830 forms a gas seal between the spring retention pin 2836 and the housing 2806. A spring retention cup 2822 retains the spring retention pin 2836. A pin retainer 2840 holds the spring retention pin 2836 in place with an enteric trigger 2826 that retains the pin retainer in place until it dissolves and used as the triggering mechanism. When the device 2800 is swallowed by the subject, the enteric trigger 2826 prevents the dispensable substance in fluid volume 2810 from being under pressure by holding the spring 2814 and the spring retention pin 2836 in place. When the device 2800 reaches the appropriate location in the GI tract, the enteric trigger 2826 degrades and/or dissolves (e.g., due to pH, change in pH, presence of certain enzyme, and/or concentration of certain enzyme) that the pin retainer 2840 is no longer sufficient to hold back the spring retention pin 2836, releasing spring 2814. The spring 2814 pushes against the piston 2818 such that the piston 2818 applies pressure to the fluid volume 2810. The piston provides friction to cause the cap 2834 to open/deploy such that the dispensable substance is delivered out of the volume 2810. This results in delivery (e.g., topical delivery) of the therapeutic agent contained in the dispensable substance.

In some embodiments, the housing of the ingestible device 2800 has a diameter from about 10 mm to about 12 mm (e.g., from about 11.3 mm to about 11.5 mm), a length from about 23 mm to about 26.5 mm (e.g., from about 25.2 mm to about 26.2 mm), a wall thickness from about 0.4 mm to about 0.6 mm (e.g., about 0.5 mm), a fluid volume from about 790 µL to about 870 µL (e.g., from about 802 µL to about 855 µL).

Figure 29A:
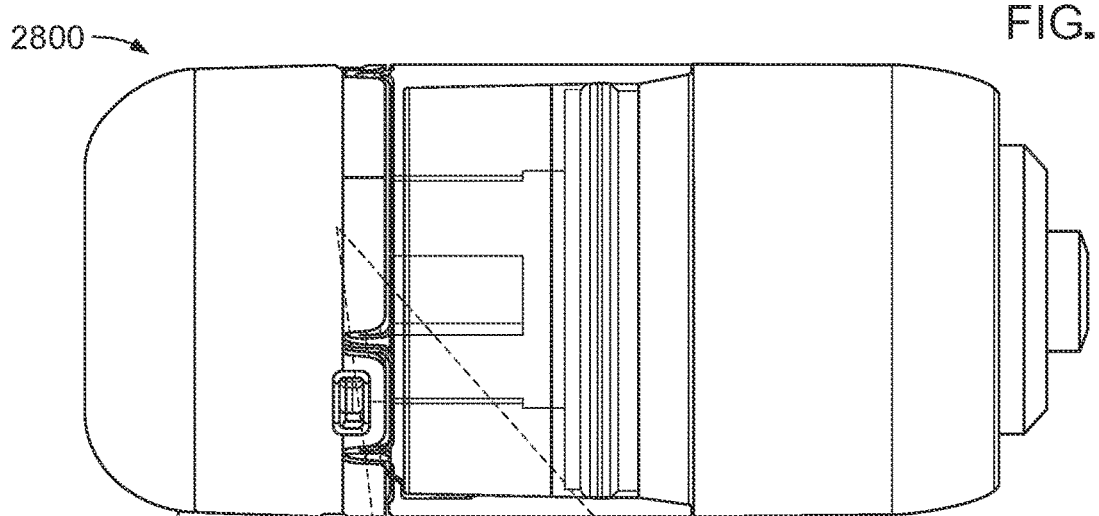
Figure 29B:
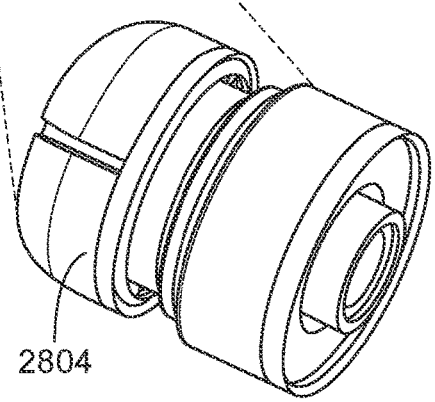

FIG. 29A shows an outer view of the embodiment of ingestible device 2800, and FIG. 29B shows and an outer view of the housing component 2804 that retains a fluid volume 2810.

Figure 30:
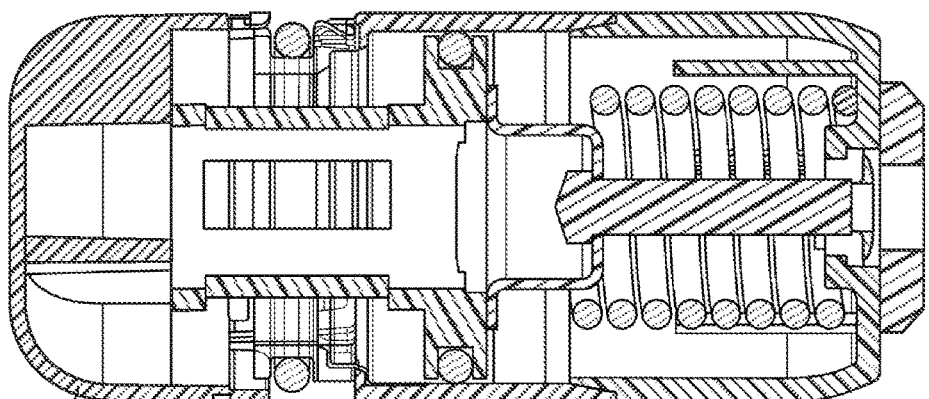

FIG. 30 shows the embodiment of the ingestible device 2800 in which the cap 2834 is opened/deployed.

Figure 31:
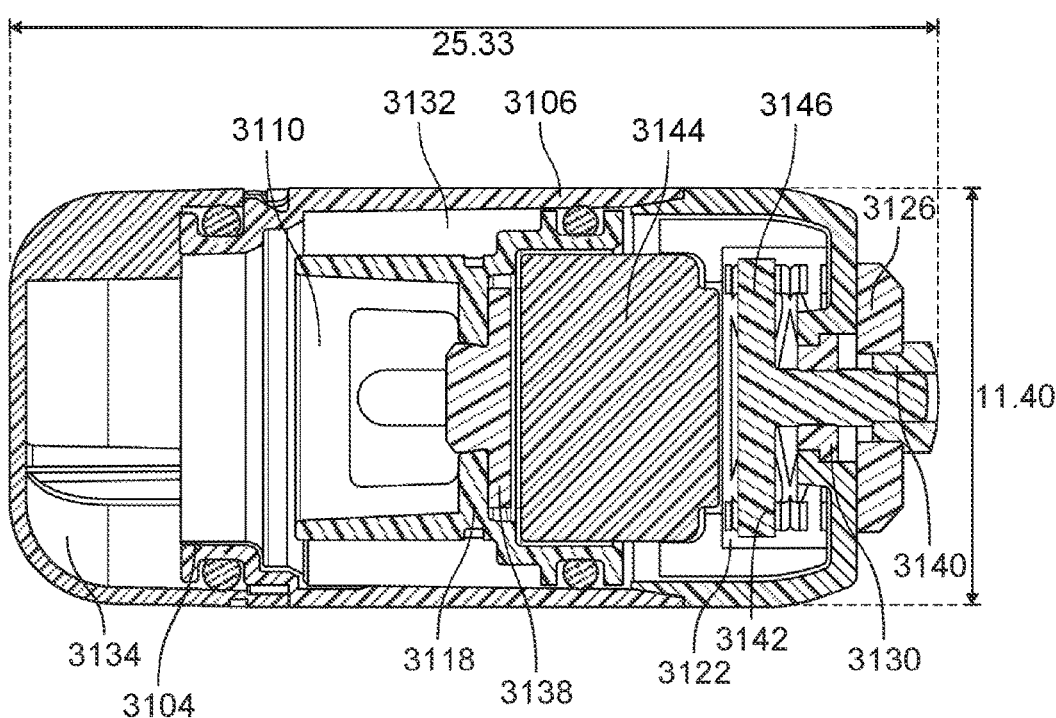
FIGS. 31-34 show states of an ingestible device.

FIG. 31 shows an embodiment of an ingestible device 3100, which contains a dispensable substance that is not under pressure when the subject swallows the ingestible device. The ingestible device 3100 has housing parts 3104 and 3106 and a fluid volume 3110 containing a dispensable substance, a piston 3118, a wave spring 3142, and an O-ring 3132. A dispensable substance-containing cap 3138 seals in the dispensable substance (e.g., drug-containing liquid) after the housing part 3104 is filled with the dispensable substance (e.g., the drug-containing liquid). A seal 3130 forms a gas seal between the switch 3146 and the housing 3106. A spring retention cup 3122 retains the wave spring 3142. A pin retainer 3140 holds the switch 3146 in place with an enteric trigger 3126 that retains the pin retainer in place until it dissolves and is used as the triggering mechanism. When the device 3100 is swallowed by the subject, the enteric trigger 3126 prevents the dispensable substance in fluid volume 3110 from being under pressure by holding the wave spring 3142 and the switch 3146 in place. When the device 3100 reaches the appropriate location in the GI tract, the enteric trigger 3126 degrades and/or dissolves (e.g., due to pH, change in pH, presence of certain enzyme, and/or concentration of certain enzyme) that the pin retainer 3140 is no longer sufficient to hold back the wave spring 3142 and releasing switch 3146. The switch 3146 completes a circuit with the gas cell 3144, which begins gas production. As pressure builds, piston 3118 slides along a trace and closes the circuit via a conductive O-ring 3132. The circuit opens when the trace ends at a defined travel distance to halt gas production by the gas cell 3144. The piston 3118 applies pressure to the fluid volume 3110 and provides friction to cause the cap 3134 to open/deploy such that the dispensable substance is delivered out of the volume 3110. This results in delivery (e.g., topical delivery) of the therapeutic agent contained in the dispensable substance.

In some embodiments, the housing of the ingestible device 3100 has a diameter from about 10 mm to about 12 mm (e.g., from about 11 mm to about 11.5 mm), a length from about 23 mm to about 26.5 mm (e.g., from about 25.2 mm to about 26.2 mm), a wall thickness from about 0.4 mm to about 0.6 mm (e.g., about 0.5 mm), a fluid volume from about 880 µL to about 940 µL (e.g., from about 890 µL to about 930 µL).

Figure 32:
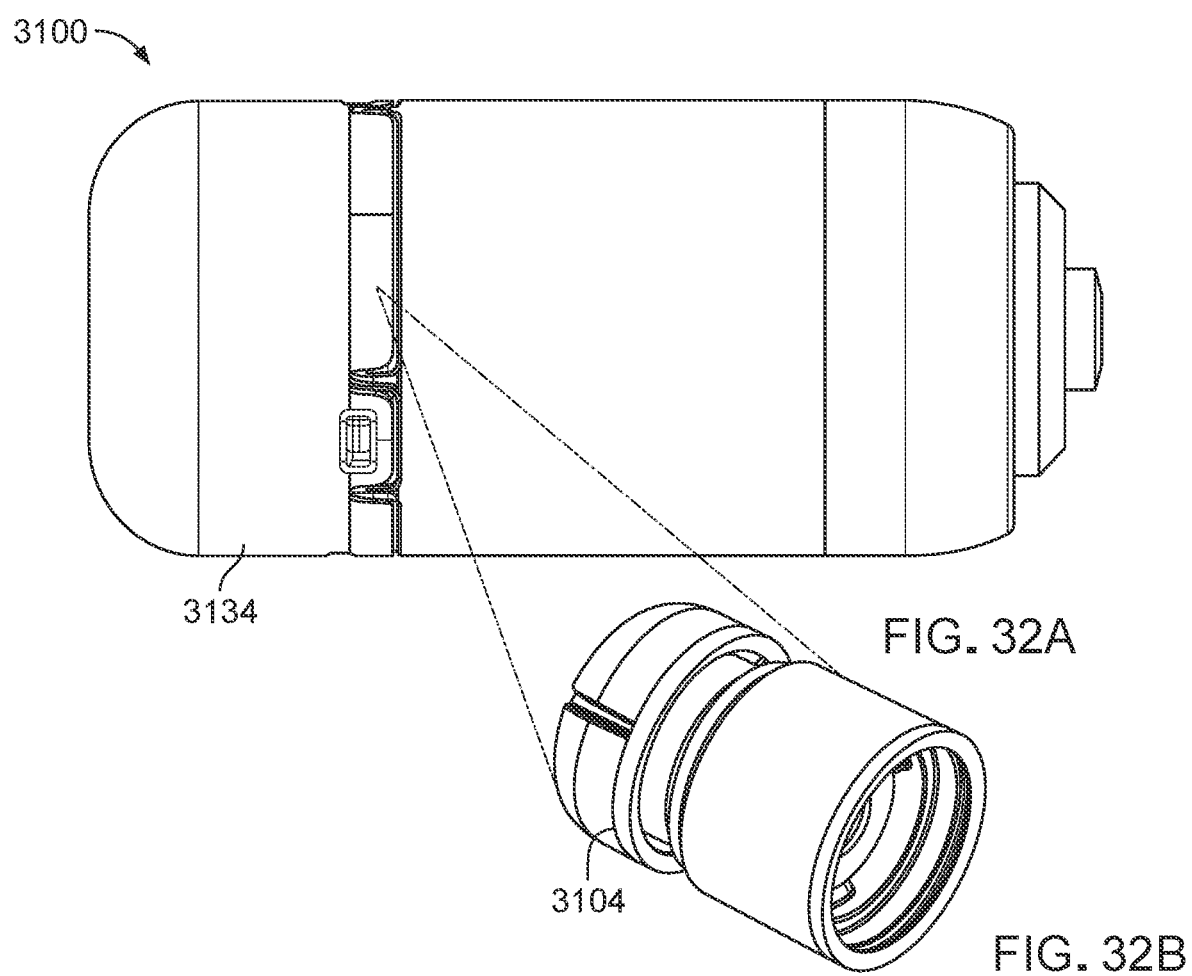

FIG. 32A shows an outer view of the embodiment of ingestible device 3100, and FIG. 32B shows an outer view of the housing component 3104 that retains a fluid volume 3110.

Figure 33:
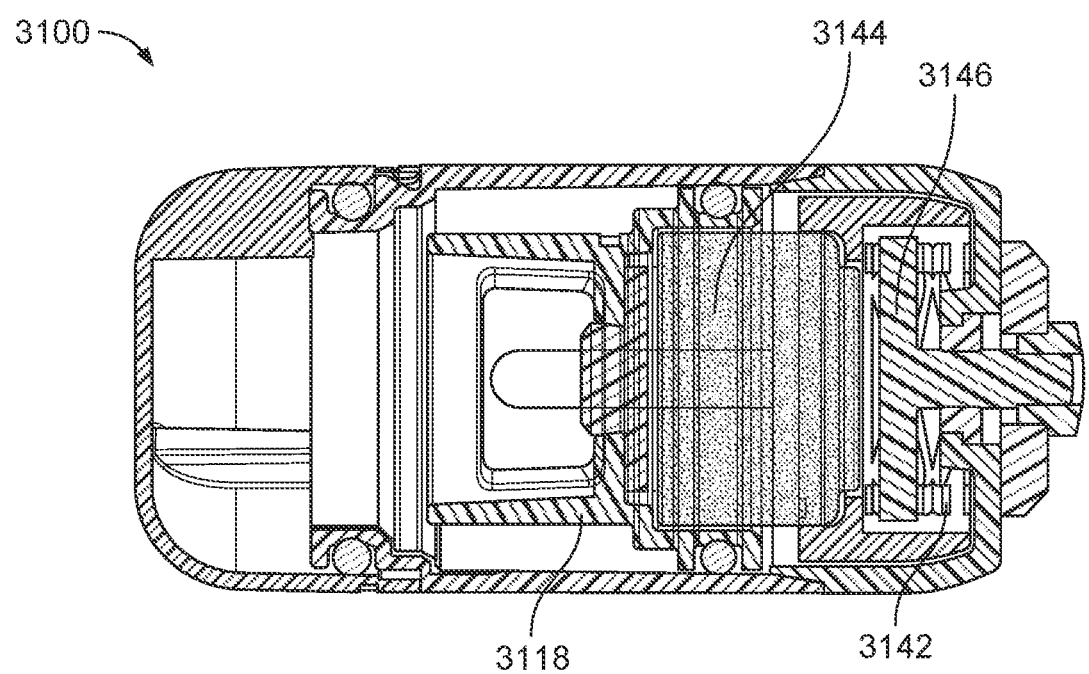

FIG. 33 shows another view of the embodiment of the ingestible device 3100.

Figure 34:
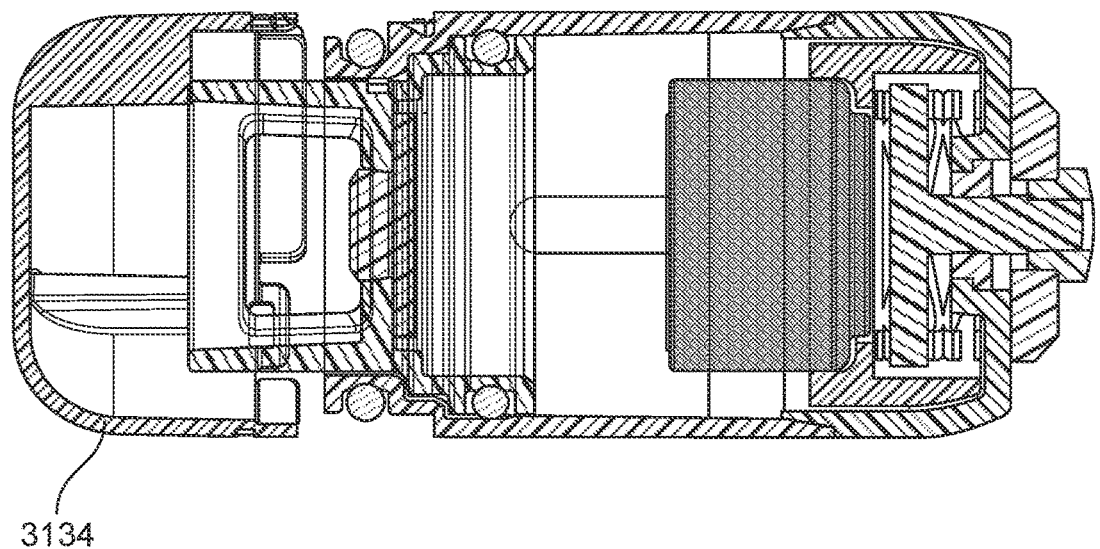

FIG. 34 shows the embodiment of the ingestible device 3100 in which the cap 3134 is opened/deployed.

In some embodiments, a length of an ingestible device can be reduced to achieve a modified 00 standardized length, e.g., approximately 23.3 mm in length, while maintaining a same diameter as a standard size 000. A reduced length of the ingestible device may result in a reduced volume available for the dispensable substance. Adjusting one or more dimensions of a gas cylinder within the ingestible device and/or altering a position of a piston may be utilized to increase an available volume for the dispensable substance, while maintaining a threshold dispensable substance volume and/or pressure provided by the gas cylinder for the ingestible device. Example embodiments are described with reference to FIGS. 35-40 herein.

Figure 35:
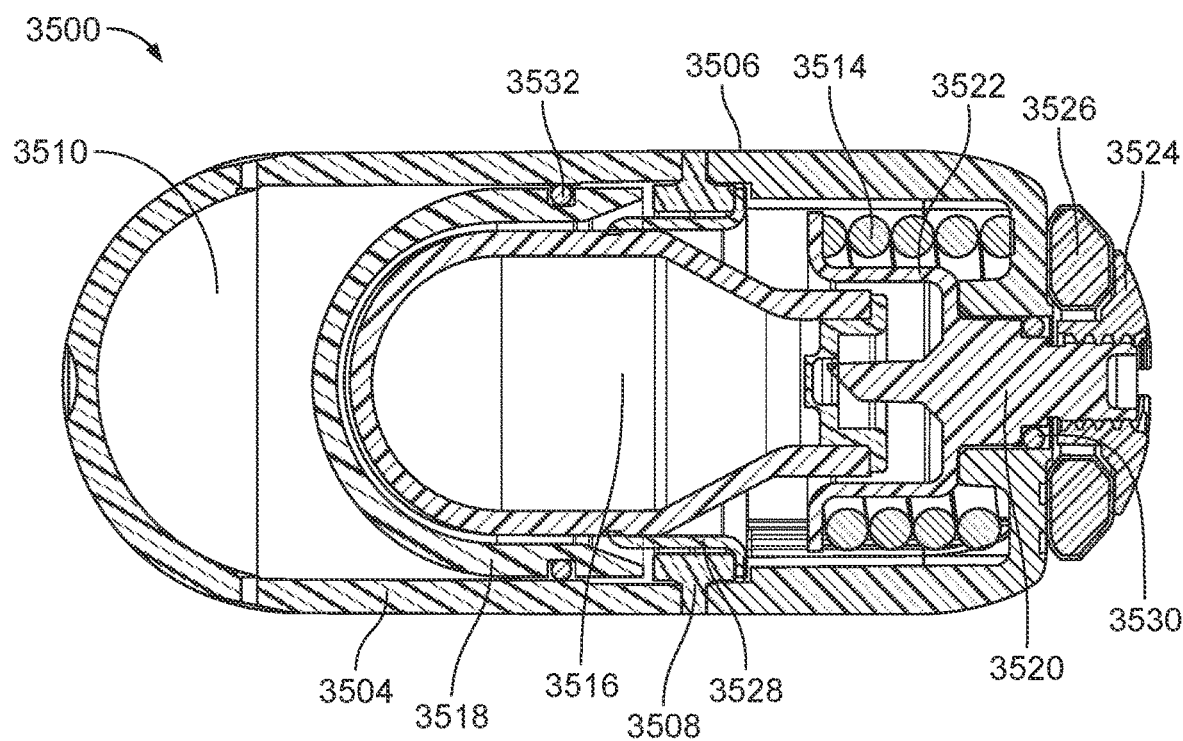
FIGS. 35-40 show ingestible devices.

FIG. 35 shows an embodiment of an ingestible device 3500 for epithelial delivery in which a length of the ingestible device is reduced to achieve a modified size 00 submucosal device, and which contains a dispensable substance that is not under pressure when the subject swallows the ingestible device. The ingestible device 3500 has housing parts 3504 and 3506 connected by a union ring 3508 and with a fluid volume 3510 containing a dispensable substance, a spring 3514, a gas cylinder 3516, a piston 3518, a piercer 3520, and an O-ring 3532. Gas cylinder 3516 is retained by retention element 3528. A seal 3530 forms a gas seal between the piercer 3520 and the housing 3506. A spring retention cup 3522 retains the spring-loaded piercer 3520. A piercer retainer 3524 holds the piercer 3520 in place with an enteric trigger 3526 that retains the piercer retainer in place until it dissolves and used as the triggering mechanism. When the device 3500 is swallowed by the subject, the enteric trigger 3526 prevents the dispensable substance in fluid volume 3510 from being under pressure by holding the spring 3514 and the piercer 3520 in place. When the device 3500 reaches the appropriate location in the GI tract, the enteric trigger 3526 degrades and/or dissolves (e.g., due to pH, change in pH, presence of certain enzyme, and/or concentration of certain enzyme) that the piercer retainer 3524 is no longer sufficient to hold back the pressure from the spring 3514. The spring 3514 forces the piercer 3520 into the gas cylinder 3516, puncturing the gas cylinder 3516 and causing gas at elevated pressure to 3534 leave the cylinder 3516. This causes the gas cylinder 3516 to press against the piston 3518 and apply pressure to the fluid volume 3510. The piston provides friction to cause the cap 3534 to open/deploy such that the dispensable substance is delivered out of the volume 3510. This results in epithelial delivery of the therapeutic agent contained in the dispensable substance.

In some embodiments, the ingestible device 3500 can retain a dispensable substance volume from about 250 µL to about 350 µL (e.g., about 267 µL), can have an expansion volume from about 230 µL to about 260 µL (e.g., about 243 µL), and can have a gas cylinder fill volume from about 140 µL to about 150 µL (e.g., about 160 µL).

In some embodiments, one or more adjustments to a piston length and/or gas cylinder dimensions can be modified for the ingestible device, e.g., ingestible device 3500. FIGS. 36-40 depict various modifications to piston length and/or gas cylinder dimensions of the ingestible device structure described with reference to FIG. 35.

Figure 36:
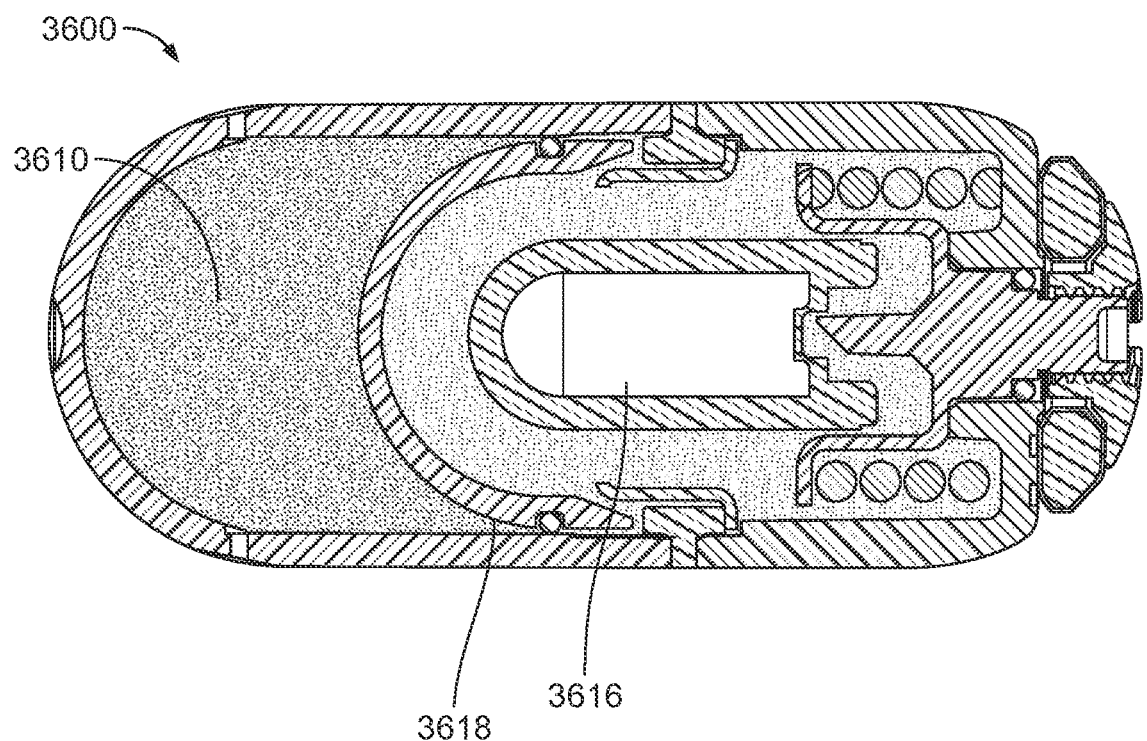

FIG. 36 shows an embodiment of an ingestible device 3600 in which a length of the ingestible device is reduced to achieve a modified size 00 submucosal device and a piston length is reduced. As depicted in FIG. 36, ingestible device 3600 includes a piston 3618, a gas cylinder 3616, and a fluid volume 3610. In some embodiments, the ingestible device 3600 can retain a dispensable substance volume from 300 µL to about 350 µL (e.g., about 322 µL), can have an expansion volume from about 350 µL to about 380 µL (e.g., about 372 µL), and can have a gas cylinder fill volume from about 35 µL to about 45 µL (e.g., about 40 µL). In some embodiments, a 280 PSIG fill pressure of the gas cylinder corresponds to a drive pressure volume from about 70-80 µL (e.g., about 75 µL). In some embodiments, a 240 PSIG fill pressure of the gas cylinder corresponds to a drive pressure volume from about 90-100 µL (e.g., about 95 µL).

Figure 37:
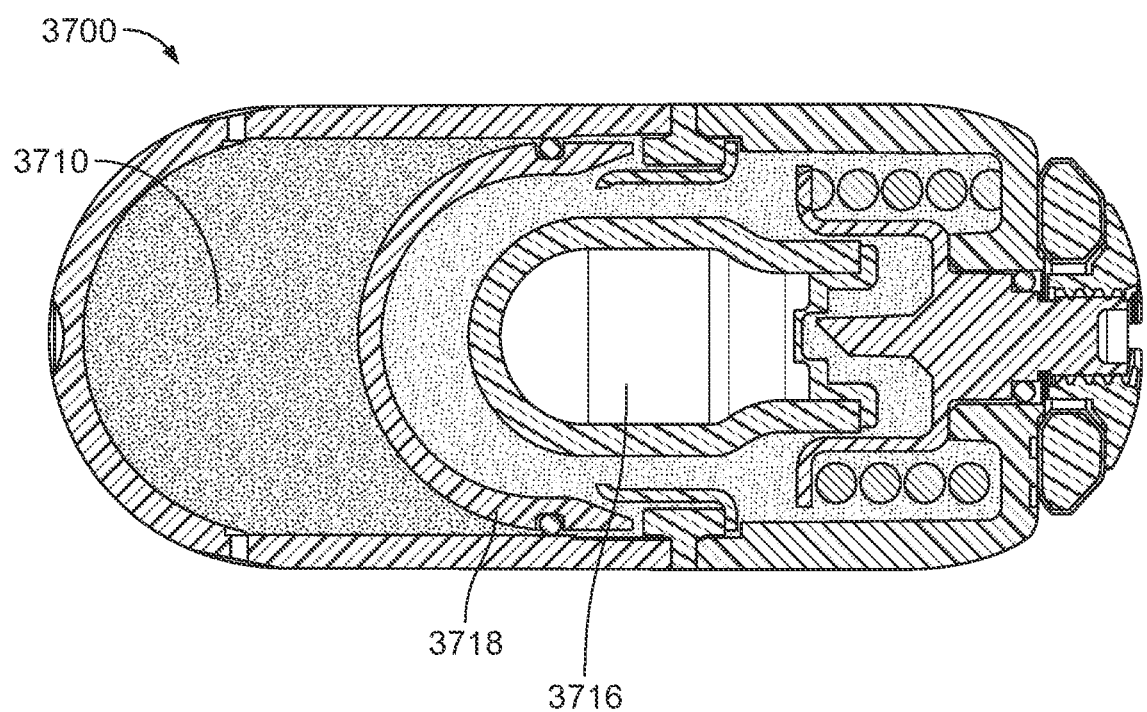

FIG. 37 shows an embodiment of an ingestible device 3700 in which a length of the ingestible device is reduced to achieve a modified size 00 submucosal device and a piston length is reduced. As depicted in FIG. 37, ingestible device 3700 includes a piston 3718, a gas cylinder 3716, and a fluid volume 3710. In some embodiments, the ingestible device 3700 can retain a dispensable substance volume from 300 µL to about 350 µL (e.g., about 332 µL), can have an expansion volume from about 320 µL to about 380 µL (e.g., about 336 µL), and can have a gas cylinder fill volume from about 65 µL to about 85 µL (e.g., about 75 µL). In some embodiments, a 280 PSIG fill pressure of the gas cylinder corresponds to a drive pressure volume from about 140-150 µL (e.g., about 145 µL). In some embodiments, a 240 PSIG fill pressure of the gas cylinder corresponds to a drive pressure volume from about 170-190 µL (e.g., about 180 µL).

Figure 38:
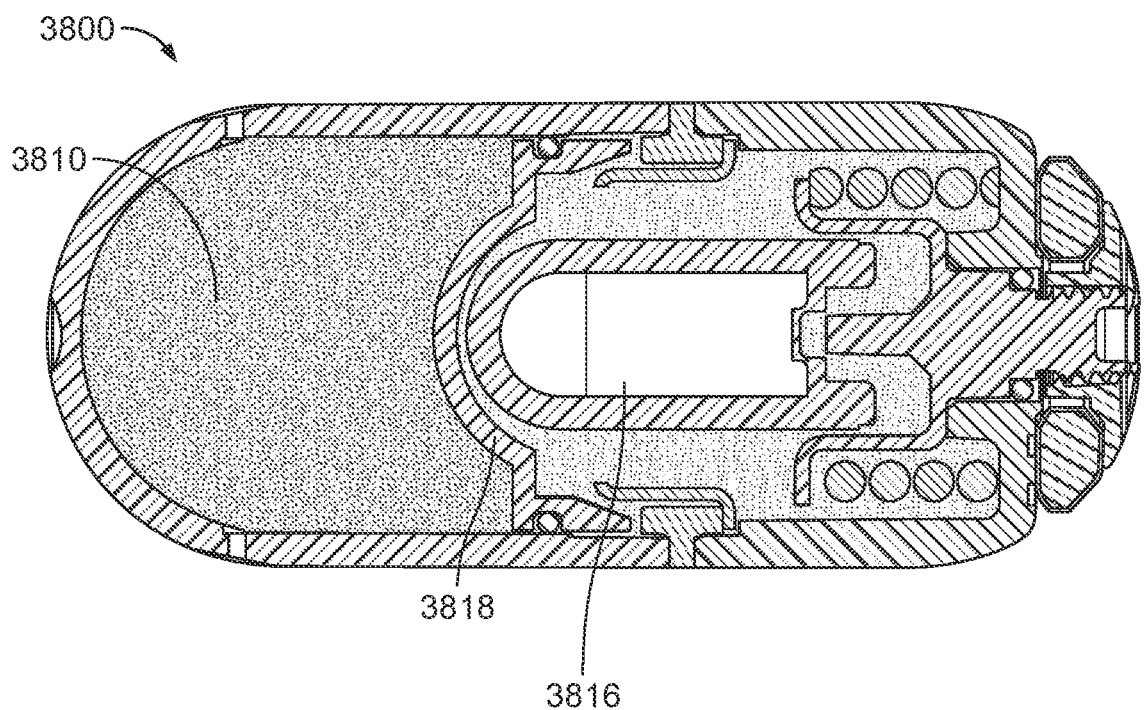

FIG. 38 shows an embodiment of an ingestible device 3800 in which a length of the ingestible device is reduced to achieve a modified size 00 submucosal device and a piston length is reduced. As depicted in FIG. 38, ingestible device 3800 includes a piston 3818, a gas cylinder 3816, and a fluid volume 3810. In some embodiments, the ingestible device 3800 can retain a dispensable substance volume from 300 µL to about 350 µL (e.g., about 335 µL), can have an expansion volume from about 300 µL to about 320 µL (e.g., about 306 µL), and can have a gas cylinder fill volume from about 35 µL to about 45 µL (e.g., about 40 µL). Piston shape of piston 3818 may result in residual dispensable substance volume of about 80 µL (of a total of 335 µL delivered) within the dispensable substance housing after delivery.

Figure 39:
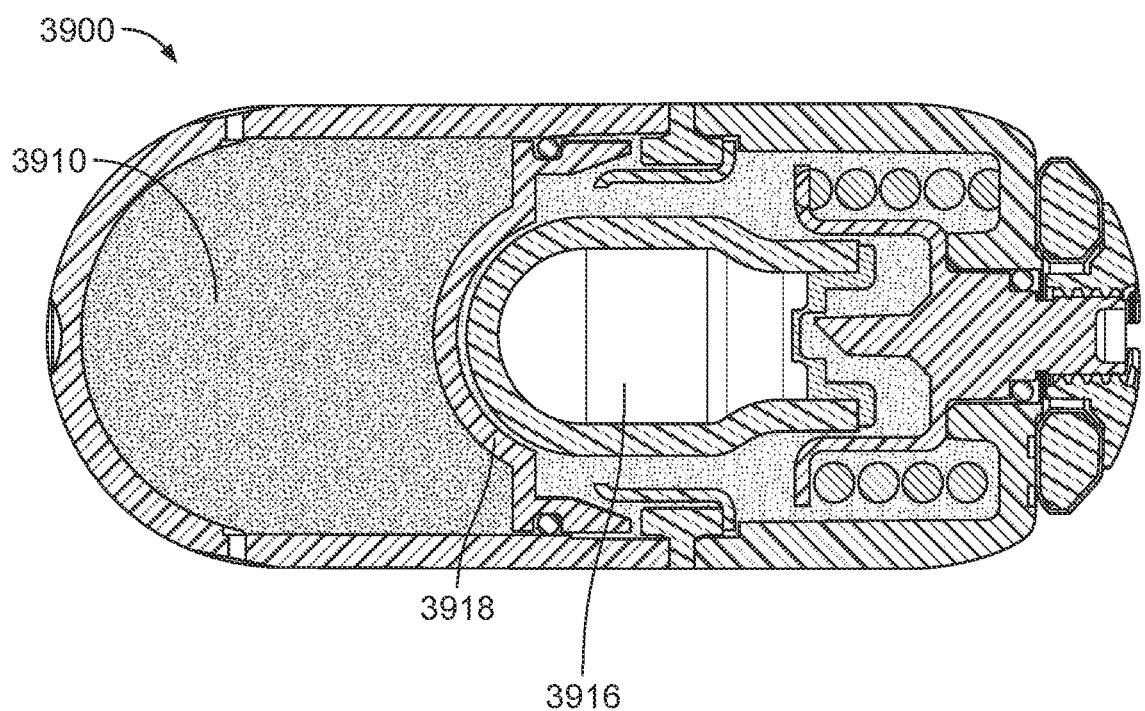

FIG. 39 shows an embodiment of an ingestible device 3900 in which a length of the ingestible device is reduced to achieve a modified size 00 submucosal device and a gas cylinder diameter is modified. As depicted in FIG. 39, ingestible device 3900 includes a piston 3918, a gas cylinder 3916, and a fluid volume 3910. In some embodiments, the ingestible device 3900 can retain a dispensable substance volume from 300 µL to about 350 µL (e.g., about 335 µL), can have an expansion volume from about 250 µL to about 290 µL (e.g., about 271 µL), and can have a gas cylinder fill volume from about 70 µL to about 80 µL (e.g., about 75 µL). Piston shape of piston 19166 may result in residual dispensable substance volume from about 70-90 µL (e.g., about 80 µL) of a total amount of dispensable substance volume delivered within the housing after delivery.

Figure 40:
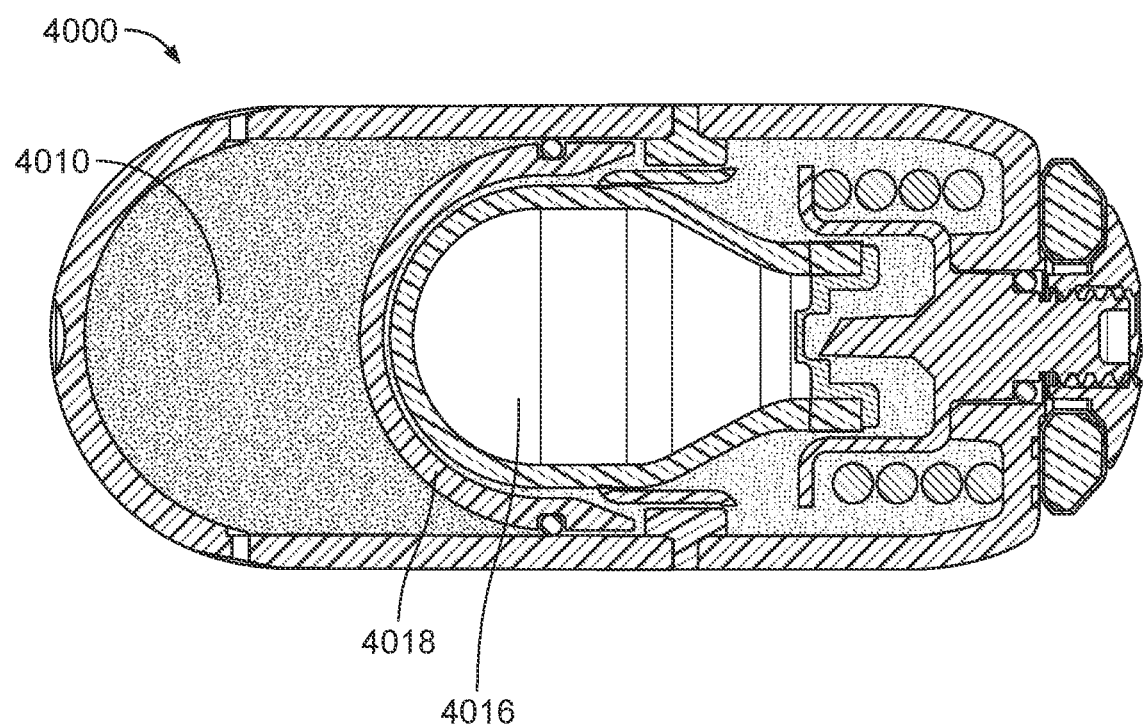

FIG. 40 shows an embodiment of an ingestible device 4000 in which a length of the ingestible device is reduced to achieve a modified size 00 submucosal device and a gas cylinder diameter is modified. As depicted in FIG. 40, ingestible device 4000 includes a piston 4018, a gas cylinder 4016, and a fluid volume 4010. In some embodiments, the ingestible device 4000 can retain a dispensable substance volume from 300 µL to about 350 µL (e.g., about 332 µL), can have an expansion volume from about 220 µL to about 270 µL (e.g., about 240 µL), and can have a gas cylinder fill volume from about 125 µL to about 145 µL (e.g., about 138 µL). In some embodiments, a 240 PSIG drive pressure of the gas cylinder corresponds to a fill pressure from about 780-800 PSIG (e.g., 792.7 PSIG). In some embodiments, 280 PSIG fill pressure of the gas cylinder corresponds to a drive pressure from about 910-930 PSIG (e.g., about 925 PSIG). In some embodiments, a 320 PSIG drive pressure of the gas cylinder corresponds to a fill pressure from about 1040-1060 PSIG (e.g., 1057 PSIG).

In some embodiments, a puncture force required to puncture a gas cylinder can be reduced such that a shorter/lower force spring can be utilized and/or a shorter/stiffer spring can be utilized.

Figure 41C:
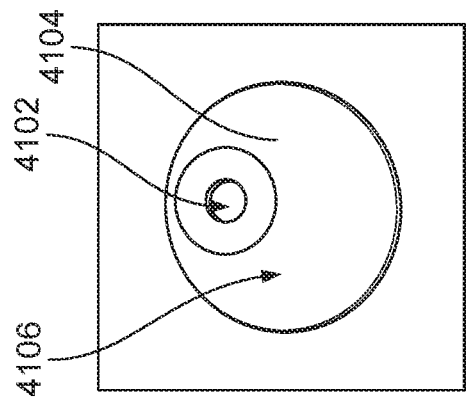
FIGS. 41A-41C show aspects of an ingestible device.
Figure 41B:
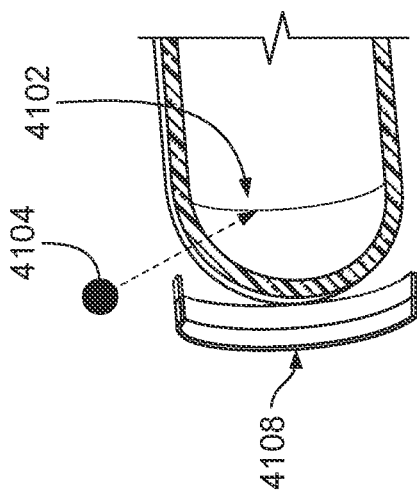
Figure 41A:
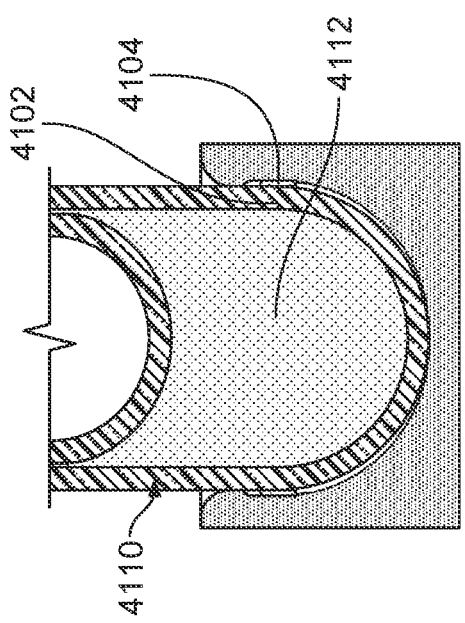

In some embodiments, as depicted in FIGS. 41A-41C, a nozzle opening 4102 can be covered by a covering including a member, e.g., a patch 4104, that forms a barrier between a dispensable substance 4112 retained within the housing 4110 and an environment external to the ingestible device. A patch 4104 can be formed of a materials that is a degradable material, an erodible material and a dissolvable material. A patch can be a barrier film composed of various materials, for example, polyethylene (PE), polypropylene, cyclic olefin copolymer (COC), cyclo-olefin-polymer (COP), polycarbonate, polyvinyl chloride (PVC), polyurethane, or the like. A patch may be a mutli-layer film, e.g., two or more layers of a same or different material, for enhanced barrier properties. Multi-layer construction of a patch 4104 can include, for example, PE/ethylene-vinyl alcohol copolymer (EVOH), ethylene-vinyl acetate (EVA)/EVOH/EVA, EVA/polyvinylidene chloride (PVDC)/EV, or the like. In some embodiments, multi-layer construction of a patch can include a metal layer.

A patch 4104 can have various shape profiles, for example, circular, rectangular, polygonal, or asymmetric profile. In some embodiments, as depicted in FIG. 41, a patch may be affixed off-center 4106 over the nozzle opening 4102 on an outside surface of the ingestible device such that a force of a jet expelled through the nozzle opening 4102, e.g., by pressurized release of the dispensable substance, may preferentially move the patch away from a direction of the formed jet.

A patch 4104 may be affixed loosely over a nozzle opening, e.g., using adhesive or another pressure sensitive method, or using static attraction. Adhesive to affix the patch may be utilized on a surface surrounding the nozzle but not directly on the nozzle. In some embodiments, a film, a coating, a foil, a band, or the like may be placed over the patch that is affixed over the nozzle opening, and may be composed on a dissolvable material, e.g., enteric material, such that the film, coating, foil, or band holds the patch in place over the nozzle opening during handling, storage, and ingestion of the ingestible device. In one example, a band 4108 is composed of a material that can dissolve upon entry into a body. The film or band may be composed of a material that is water soluble, e.g., hydroxypropyl methyl cellulose (HPMC), hydroxypropylmethylcellulose acetate succinate (HPMCAS), or gelatin. The film or band 4108 may be composed of a material that includes a pH-dependent solubility, e.g., composed of or including polymethacrylate, such that the material is more stable under acidic conditions, e.g., pH 1-4, and where a rate of dissolution increases when the material is exposed to higher pH, e.g., pH 5-7.

In some embodiments, a band covering a nozzle opening can be composed of a heat shrink material that is heat shrunk to the housing such that it provides a nozzle covering. An example of a heat shrink material is polyethylene terephthalate (PET). Additional examples of heat shrink materials include polyolefin, polyethylene, LDPE, PTFE, FEP and COC. In general, such a heat shrink material does not operate by being dissolved. Instead, it is broken (e.g., punctured) by the pressure of the dispensable material applied to the heat shrink material. Such a heat shrunk band can have a thickness of, for example, from about 5 μm to about 100 μm (e.g., from about 5 μm to about 50 μm, about 10 μm, about 12 μm, about 15 μm, about 50 μm). Specific examples include heat shrunk PET (e.g., medical film) having a thickness of about 12 μm, heat shrunk polyolefin (e.g., transit packing film) having a thickness of about 15 μm, and heat shrunk polyethyelene (e.g., transit packing film) having a thickness of about 50 μm.

In general, a covering (e.g., a film, a coating, a foil, a band) of a nozzle opening can be scored, e.g., to make it easier for the seal to be broken when desired. Generally, such scoring can be configured as desired. As an example, scoring can be configured as a series of parallel lines. As another example, scoring can be configured as a grid (cross-hatched). As a further example, scoring can be configured as a plurality of dots (e.g., equally spaced dots). In some embodiments of a scored seal, the seal is composed of LDPE, for example of having a thickness of from 20 μm to 75 μm (e.g., 25 μm, 50 μm). For example, a seal composed of LDPE can be scored with stripes or a grid or a plurality of dots, with the LDPE having a thickness of 25 μm or 50 μm.

In some embodiments, covering (e.g., a coating, a film, a band, or a patch has a minimal burst pressure. In some embodiments, for example, the minimal burst pressure is less than 420 psig.

Generally, the minimal burst pressure is more than 5 psig (e.g., more than 10 psig, more than 25 psig, more than 50 psig more than 80 psig). For example, in certain embodiments, the burst pressure can be in a range of from 5 psig to any one of the minimal burst pressures noted earlier in this paragraph.

In some embodiments, a coating or film can be applied over a nozzle opening 4102 that may dissolve/degrade or otherwise become unstable after the ingestion of the ingestible device. In some embodiments, the coating or film is hydrophobic. The coating or film can be structurally weakened by drilling/scoring, e.g., using laser drilling, and/or can be composed of a material that weakens based on an environment surrounding the material, e.g., an enteric material within the body. In one example, laser microtoming can be utilized to thin a coating or film, e.g., a sanding/polishing process, to reduce the coating or film thickness. In some embodiments, a coating or film of an enteric material can be applied over a nozzle opening 4102 and a portion of an outer surface of the ingestible device. A machining/polishing processes can be utilized to control a final thickness of the applied coating or film, e.g., centerless lapping or grinding. The coating or film can be further processed using a laser to drill, score, and/or perforate a portion of the coating or film to mechanically weaken the coating or film.

FIGS. 42A-47C depict embodiments of a patch, coating, film, foil and/or band that can be affixed to or in contact with the nozzle opening. While such embodiments are depicted in these figures, the disclosure is not limited in this sense. In some embodiments, a combination of more than one (e.g., more than two, more than three) such approaches to covering a nozzle opening may be used in a given ingestible device. Further, variations on the approaches disclosed herein are available so long as they generally comport with the relevant function(s), such as, for example, providing a barrier between a dispensable substance (e.g., drug-containing liquid) retained within the drug housing and an environment external to the ingestible device.

Figure 42B:
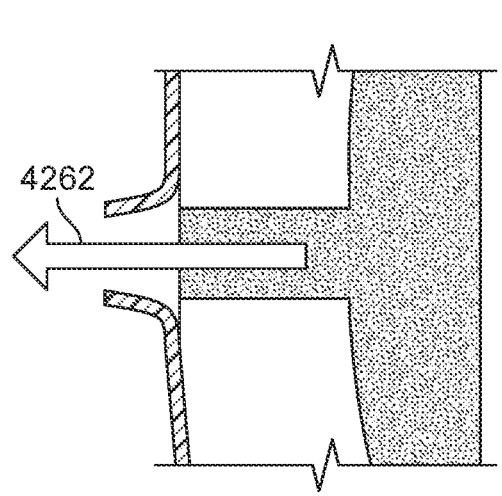
Figure 42A:
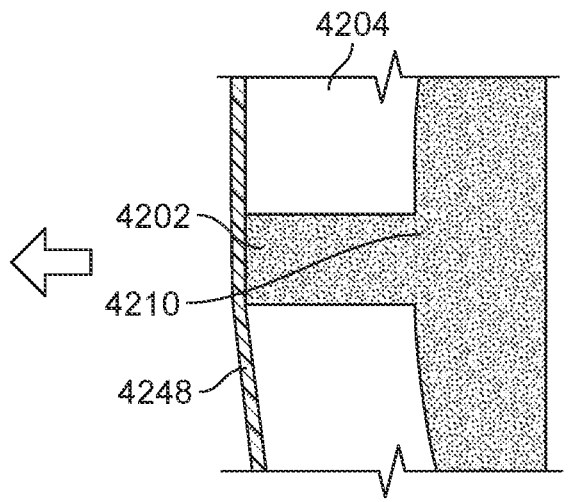

In some embodiments, as depicted in FIGS. 42A and 42B, a nozzle opening 4202 can be covered by a covering including a member 4248, e.g., a patch, film, foil, band, or the like, that forms a barrier between a fluid volume 4210 including a dispensable substance (e.g., drug-containing liquid) retained within the housing and an environment external to the ingestible device. Certain embodiments including a nozzle covering member 4202 formed of a film, foil, patch, band, or the like are discussed, for example, with reference to FIGS. 17, 18, 19A-N of U.S. Ser. No. 62/932, 459, and optionally applicable to FIGS. 42A and 42B.

Internal pressure from a pressurized dispensable substance, e.g., during pressurized dispensable substance release, can cause the dispensable substance to puncture the covering member or partially peel/detach the covering member from the outer surface of the ingestible device to allow dispensable substance-containing jets 4262 to form. The covering member 4248 can be composed of various materials, e.g., PE, PP, PVC, cellulose acetate, hot blocking film, and the like. In some embodiments, the covering member can be composed of material that is intended to be insoluble in gastric media but may break down in the small intestine based on pH (e.g., enteric materials) or one or more enzymes, such as, for example, one or more pancreatic enzymes (e.g., lipid-based materials). The covering member 4248 can be composed of material that can hydrate and/or soften when exposed to gastric media without substantially dissolving. The covering member 4248 in this embodiment and others described herein can be composed on a gas-permeable membrane, e.g., which may help with de-gassing during a process of filing the ingestible device. The covering member can be applied, for example, in a post-molding operation, e.g., from a reel.

In some embodiments, the covering member 4248 can be a thin shrink-fit film or adhesive label component applied to an external surface of the ingestible device to cover the nozzle openings. In certain embodiments, the thin film or adhesive label can be a thin barrier, e.g., having a thickness from 20 μm to 40 μm (e.g., from 25 μm to 35 μm, 30 μm).

In some embodiments, the covering member 4248 can be an external band that is applied to cover the nozzle openings 4202. In certain embodiments, the band can be, for example, from 100 μm to 200 μm (e.g., from 125 μm to 175 μm, e.g., 150 μm) thick. Optionally, the band can be composed of materials such as gelatin, HPMC, or other materials that are soluble in gastric media, or can be composed of enteric material.

In some embodiments, the covering member 4248 can be a partial film or covering, e.g., an external cap, that is applied to an outside of the ingestible device to cover the nozzle openings 4202. The cap can be, for example, from 100 μm to 200 μm (e.g., from 125 μm to 175 μm, e.g., 150 μm) thick and/or cover less than the full exterior of the ingestible device.

Figure 43B:
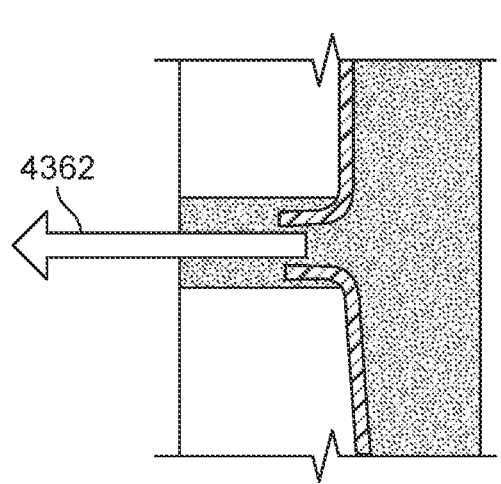
Figure 43A:
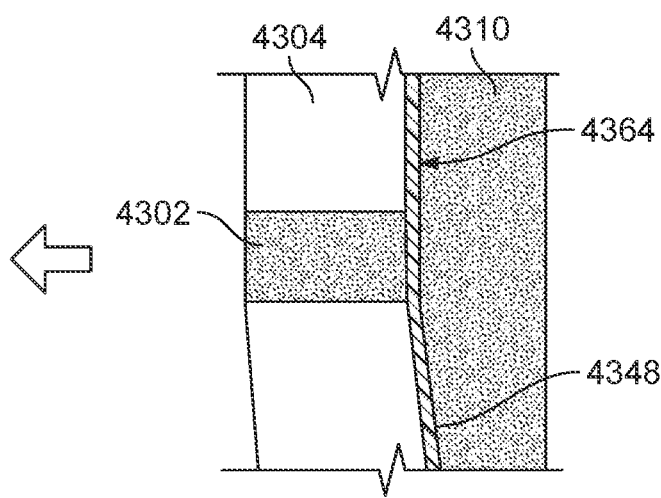

In some embodiments, as depicted in FIGS. 43A and 43B, a covering member 4348, e.g., patch, film, foil, band, coating, or the like, that forms a barrier between a fluid volume 4310 including a dispensable substance (e.g., a drug-containing liquid) retained within the housing 4304 and an environment external to the ingestible device can be applied and/or affixed to an interior surface 4364 of the ingestible device. In some embodiments, the covering member 4348 is a thin film that is applied to an internal surface of a primary container 4304 of the ingestible device, e.g., during a molding process, to cover the nozzle openings 4302. Internal pressure from a pressurized dispensable substance, e.g., during pressurized dispensable substance release, can cause the dispensable substance to puncture the covering member or partially peel/detach the covering member from the outer surface of the ingestible device to allow dispensable substance-containing jets 4362 to form. The covering member 4348 can be composed of various materials, e.g., COC-based films such as COC+LLDPE laminate, and the like. In some embodiments, the covering member 4348 can be composed of material that is intended to be insoluble in gastric media but may break down in the small intestine based on pH (e.g., enteric materials) and/or or one or more enzymes, such as, for example, one or more pancreatic enzymes (e.g., lipid-based materials). The covering member 4348 can be composed of material that can hydrate and/or soften when exposed to gastric media without substantially dissolving. The covering member 4348 in this embodiment and others described herein can be composed on a gas-permeable membrane, e.g., which may help with de-gassing during a process of filing the ingestible device. The covering member 4348 can be applied, for example, using a molding process, e.g., based on an in-molded label or blow molded onto an interior surface 4364 of the ingestible device. The covering member can be, for example, from 20 μm to 40 μm (e.g., from 25 μm to 35 μm, 30 μm) thick. In some embodiments, the covering member can be applied/affixed without an adhesive, e.g., molded bond.

Figures 44A, 44B:
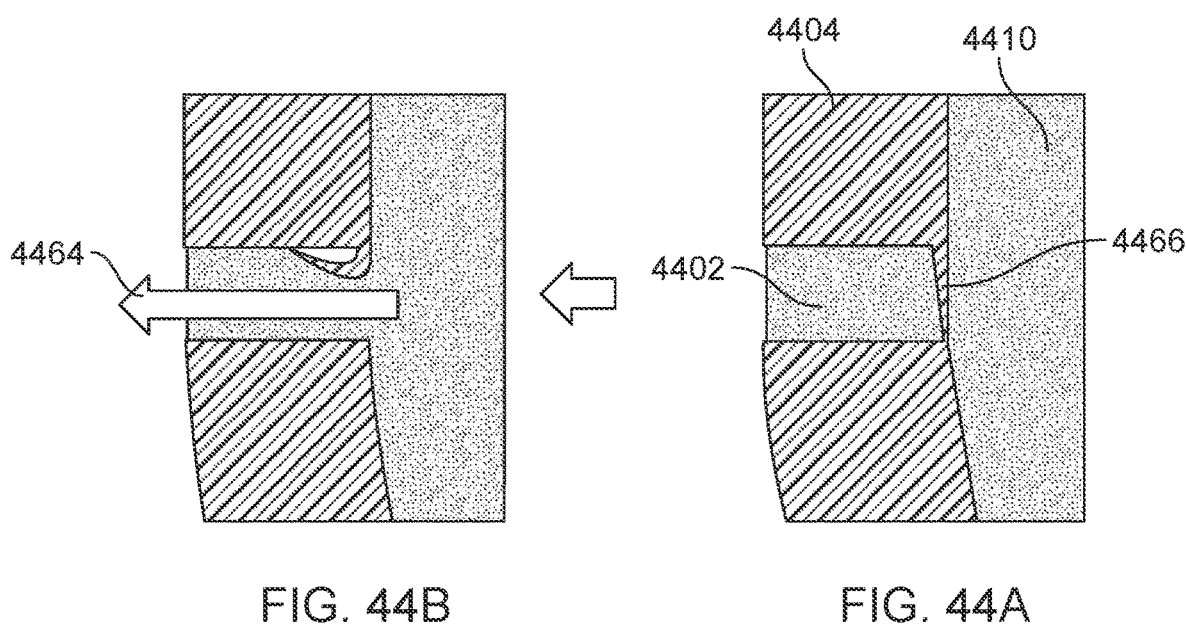

In some embodiments, as depicted in FIGS. 44A and 44B, a covering member can be a feature, such as, for example, a molded feature 4466 formed on (or adjacent to) an interior end of a nozzle opening 4402 and which forms a barrier between a fluid volume 4410 including a dispensable substance (e.g., drug-containing liquid) retained within the housing 4404 and an environment external to the ingestible device. Internal pressure from a pressurized dispensable substance, e.g., during pressurized dispensable substance release, can cause the dispensable substance to puncture the covering member 4466 fully or partially peel/detach the covering member from the outer surface of the ingestible device to allow dispensable substance-containing jets 4464 to form. The covering member can be composed of various materials, e.g., COC-based films such as COC+LLDPE laminate, and the like. In some embodiments, the covering member 4466 can be composed of material that is intended to be insoluble in gastric media but may break down in the small intestine based on pH (e.g., enteric materials) and/or one or more enzymes, such as, for example, one or more pancreatic enzymes (e.g., lipid-based materials). The covering member 4466 can be composed of material that can hydrate and/or soften when exposed to gastric media without substantially dissolving.

Figures 45A, 45B:
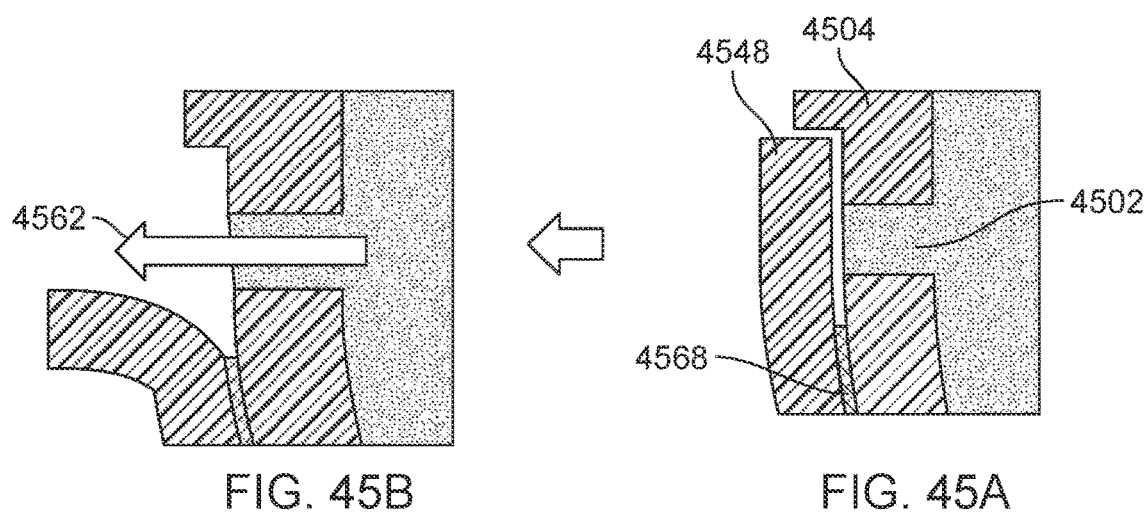

In some embodiments, as depicted in FIGS. 45A and 45B, a covering member 4548 can be a covering member that is tethered 4568 to the ingestible device, e.g., tethered to an outer portion of the housing 4504. The covering member 4548 can be formed of a flexible material, e.g., an elastomer material. Internal pressure from a pressurized dispensable substance, e.g., during pressurized dispensable substance release, can cause the dispensable substance to detach/displace a portion or all of the covering member from the nozzle opening 4502 of the ingestible device to allow dispensable substance-containing jets 4562 to form.

Figures 46A, 46B:
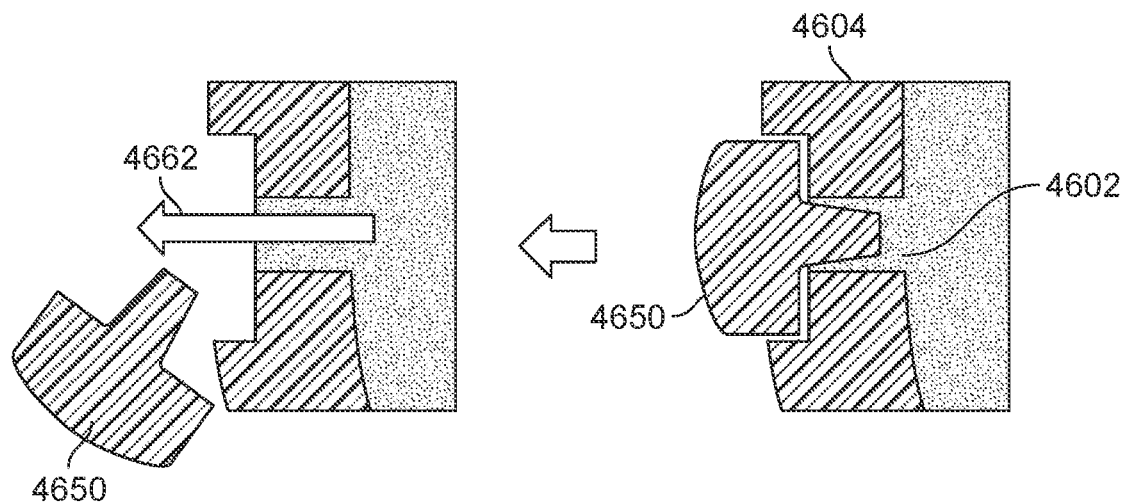

In some embodiments, as depicted in FIGS. 46A and 46B, a covering member can be a plug 4650, e.g., an elastomer plug, that can block the nozzle opening 4602 from an outside surface of the ingestible device. The plug can be tethered to a housing component 4604 of the ingestible device to prevent dispersion of the released plug into the body. The plug 4650 can be formed of biodegradable materials such that the plug can be processed by the body. Internal pressure from a pressurized dispensable substance, e.g., during pressurized dispensable substance release, can cause the dispensable substance to detach/displace the plug 4650 from the nozzle opening of the ingestible device to allow dispensable substance-containing jets 4662 to form.

Figures 47A, 47B, 47C:
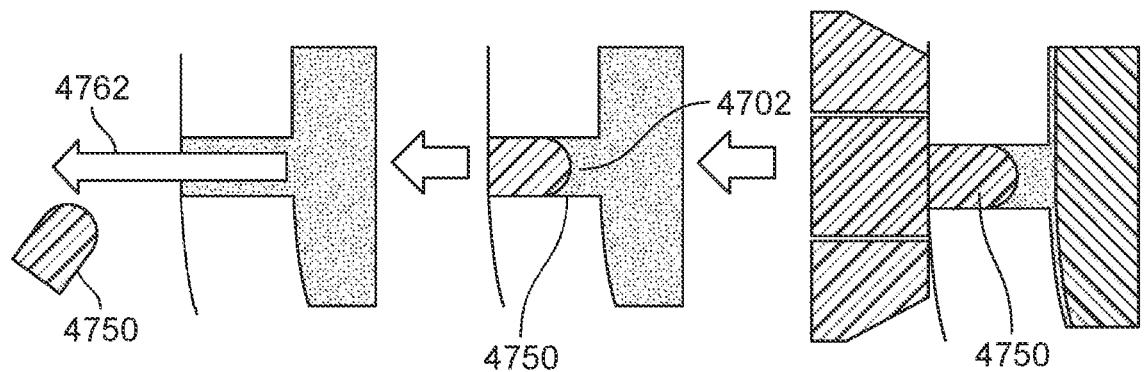

In some embodiments, as depicted in FIGS. 47A-47C, a nozzle opening 4702 can be blocked by a plug 4750 that is formed by applying a liquid-fil gel from an outside apparatus 4770 of the ingestible device, e.g., via a nozzle or rotating mandrel. The liquid-fill gel can harden before a dispensable substance filling process to provide a plug 4750. The gel can be composed of a material that is substantially insoluble in gastric media/dispensable substance, but can break down in small intestine-based pH (e.g., an enteric material) and/or one or more enzymes, such as for example, one or more pancreatic enzymes (e.g., lipid-based material). Internal pressure from a pressurized dispensable substance, e.g., during pressurized dispensable substance release, can cause the dispensable substance to displace the gel from the nozzle opening 4702 of the ingestible device to allow dispensable substance-containing jets 4762 to form.

Figure 48:
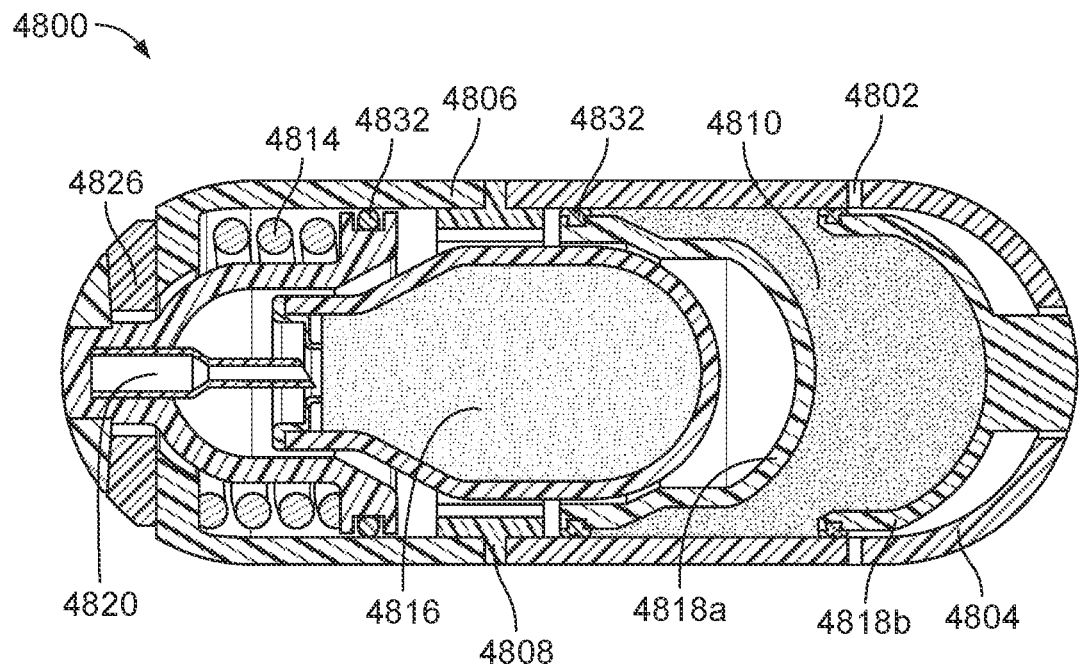
FIGS. 48 and 49 show states of an ingestible device.
Figure 49:
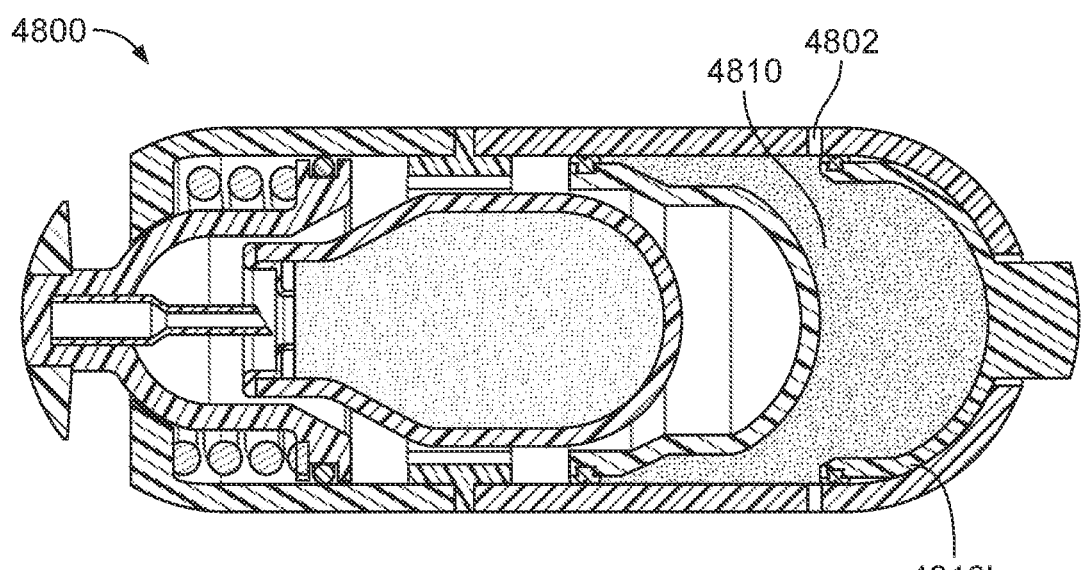

FIGS. 48 and 49 depict an embodiment of an ingestible device 4800 utilizing an internal piston. Ingestible device 4800 contains a dispensable substance that is not under pressure when the subject swallows the ingestible device. In FIG. 48, the nozzles 4802 are depicted as covered, and in FIG. 49 the nozzles 4802 are uncovered. The ingestible device 4800 has housing parts 4804 and 4806 connected by a union ring 4808 and with a fluid volume 4810 containing a dispensable substance, a spring 4814, a gas cylinder 4816, a first piston 4818*a* and a second piston 4818*b*, a piercer 4820, and an O-ring 4832. The piercer 4820 is held in place with an enteric trigger 4826 that dissolves and used as the triggering mechanism. When the device 4800 is swallowed by the subject, the enteric trigger 4826 prevents the dispensable substance in fluid volume 4810 from being under pressure by holding the spring 4814 and the piercer 4820 in place. When the device 4800 reaches the appropriate location in the GI tract, the enteric trigger 4826 degrades and/or dissolves (e.g., due to pH, change in pH, presence of certain enzyme, and/or concentration of certain enzyme) such that the spring 4814 forces the piercer 4820 into the gas cylinder 4816, puncturing the gas cylinder 4816 and causing gas at elevated pressure to leave the cylinder 4816. This causes the gas cylinder 4816 to press against the first piston 4818*a* and apply pressure to the fluid volume 4810. The pressurized fluid volume 4810 applies pressure to the second piston 4818*b* cause the second piston 4818*b* to slide and expose the nozzles 4802 such that the dispensable substance is delivered out of the nozzles 4802 in the form of a jet. This can result in trans-epithelial and/or epithelial delivery of the therapeutic agent contained in the dispensable substance.

In some embodiments, a plug/cover can be affixed over a nozzle opening, where the plug/cover is further connected to a piercer component of the ingestible device via connectors and a ring component. FIGS. 50A and 50B depict an embodiment of an ingestible device 5000 including a plug/cover assembly. Ingestible device 5000 includes nozzle opening(s) 5002, a drug container 5004, a drive housing 5006, an o-ring 5032, a retention element 5028, a piercer 5020, a gas seal 5030, a trigger element 5026, a trigger support 5024, a spring 5014, a gas cylinder 5016, a union ring 5008, and a piston 5018. The ingestible device 5000 optionally includes a nozzle cover 5048.

A plug/cover assembly can be a single formed piece, e.g., composed of a plastic material, and fitted externally to the ingestible device such that the plug(s) 5050 cover the nozzle opening(s) 5002 on the ingestible device 5000. The plug/cover assembly can further include connectors 5052 that connect the plug/cover assembly to a ring 5054 component that can be attached to a top of the piercer 5020 and external to a trigger element 5026, such that the ring component 5054 is pulled down by the piercer 5020 when the piercer is released, e.g., after the trigger element 5026 dissolves/ degrades, and the plug/cover 5050 are pulled away from the nozzle opening 5002 by the movement of the ring 5054. In some embodiments, the plug/cover 5050 are pulled away from the nozzle opening 5002 by the movement of the ring 5054 in a direction parallel to a length of the ingestible device 5000, e.g., along the outer surface of the ingestible device. In some embodiments, the plug/cover 5050 are pulled away from the nozzle opening 5002 by the movement of the ring 5054 in a direction outwards, e.g., normal, or angled-away, from an outer surface of the ingestible device 5000.

In some embodiments, a band can be affixed over one or more nozzle openings, where the band is further connected to a piercer component of the ingestible device via connectors and a ring component. FIGS. 51A and 51B depicts an embodiment of an ingestible device 5100 including a band assembly. Ingestible device 5100 includes nozzle opening(s) 5102, a drug container 5104, a drive housing 5106, an o-ring 5132, a retention element 5128, a piercer 5120, a gas seal 5130, a trigger element 5126, a trigger support 5124, a spring 5114, a gas cylinder 5116, a union ring 5108, and a piston 5118. The ingestible device 5100 optionally includes a nozzle cover 5148.

A band assembly can be a single formed piece, e.g., composed of a plastic material, including a band 5156, connectors 5152, and a ring component 5154. A band assembly can be instead multi-piece assembly composed of a band 5156 that is placed around the ingestible device 5100 during a filling process and a connector/ring assembly that are affixed to the band 5156 and piercer component 5120. The band assembly can be connected to the piercer 5120 by a ring component 5154 that can be attached to a top of the piercer component and external to a trigger element 5126, such that the ring component 5154 is pulled down by the piercer 5120 when the piercer is released, e.g., after the trigger element 5126 dissolves/degrades, and the band 5156 is pulled away from the nozzle opening(s) 5102, e.g., along a length of the ingestible device 5100, to expose the nozzle opening(s) 5102 by the movement of the ring 5154 prior or simultaneously to the delivery of the dispensable substance via the nozzle openings 5102.

In some embodiments, as depicted in FIGS. 52A-52D, an ingestible device 5200 includes a sliding cover 5248. The sliding cover 5248 can be a single formed piece, e.g., a sleeve composed of a plastic material, and fitted externally to the ingestible device 5200 such that a portion of the sliding cover covers the nozzle opening(s) 5202 on the ingestible device 5200. The sliding cover 5248 can be attached to a top of the piercer component 5220 and external to a trigger element 5226, such that the sliding cover 5248 is pulled down by the piercer 5220 when the piercer is released, e.g., after the trigger element 5226 dissolves/ degrades, and the sliding cover 5248 is pulled away from the nozzle opening 5202 by the movement of the piercer 5220. The sliding cover 5248 can be pulled away from the nozzle openings 5202 by the movement of the sliding cover in a direction parallel to a length of the ingestible device 5200, e.g., along the outer surface of the ingestible device, prior or simultaneously to the delivery of the dispensable substance within fluid volume 5210 via the nozzle openings 5202.

Figure 53A:
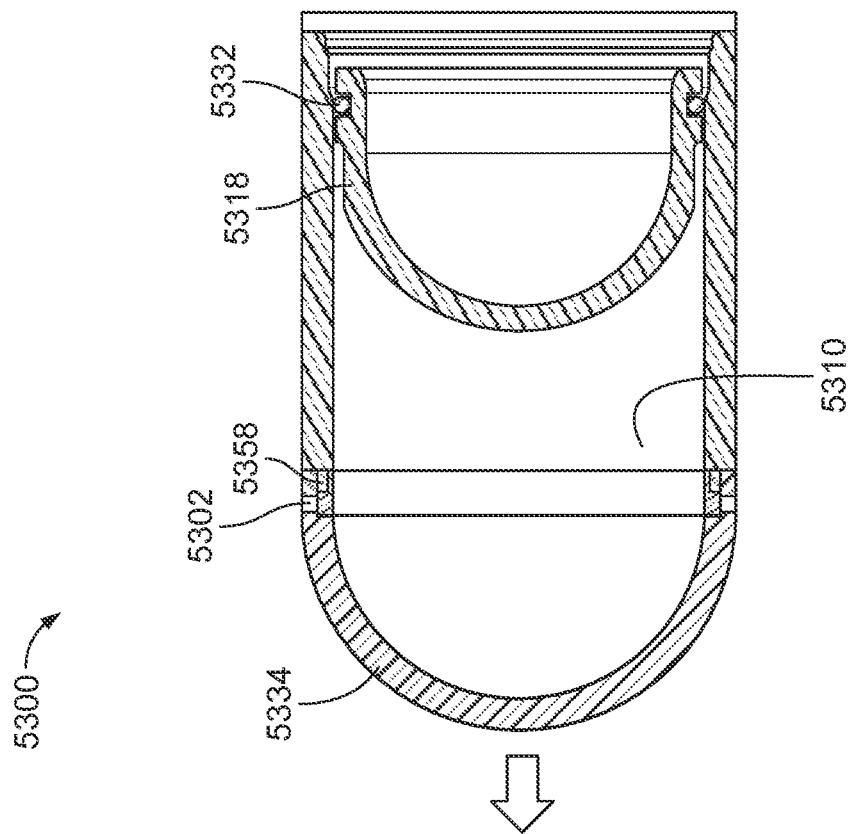
FIGS. 53A and 53B show views of a portion of an ingestible device.
Figure 53B:
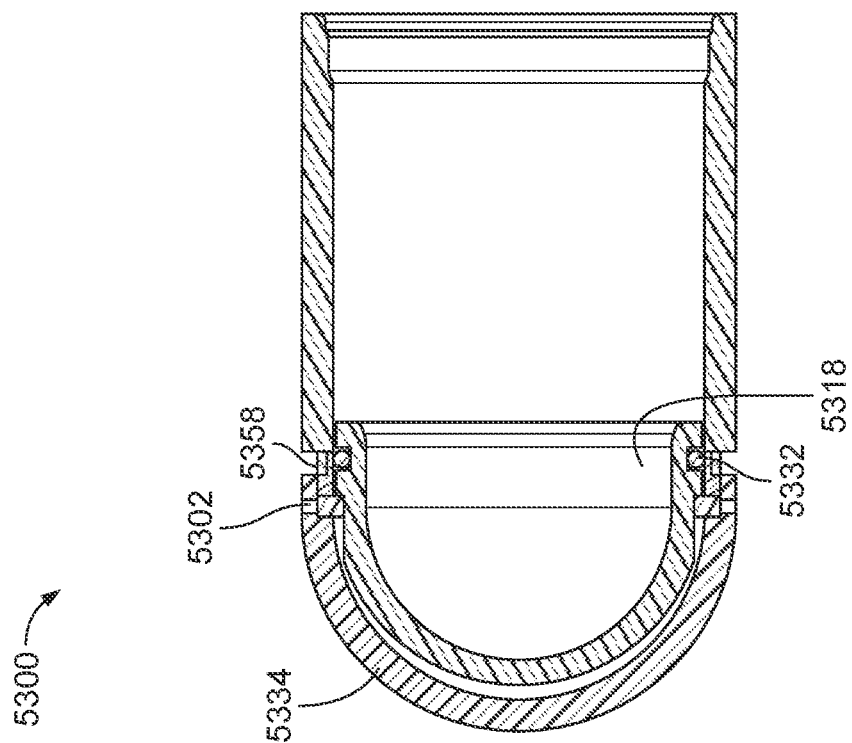

In some embodiments, as depicted in a partial rendering of an ingestible device 5300 in FIGS. 53A and 53B, ingestible device 5300 includes a cap 5334 affixed over one end of an ingestible device 5300 and partially enclosing a volume 5310. A seal 5358, e.g., an over-molded elastomer based seal, can be utilized to seal a dispensable substance within the volume 5310 and prevent the dispensing of the dispensable substance while the cap 5334 is affixed over the end of the ingestible device 5300. The seal 5358 can additionally prevent movement of the cap 5334 prior to a delivery of the dispensable substance. When the device 5300 is swallowed by the subject, the enteric trigger prevents the dispensable substance in the fluid volume from being under pressure by holding the spring and the piercer in place. When the device reaches the appropriate location in the GI tract, the enteric trigger degrades and/or dissolves (e.g., due to pH, change in pH, presence of certain enzyme, and/or concentration of certain enzyme) such that the spring forces the piercer into the gas cylinder, puncturing the gas cylinder and causing gas at elevated pressure to leave the cylinder. This causes the gas cylinder to press against the piston and apply pressure to the fluid volume. The pressurized fluid volume applies pressure to the cap and causes the cap to slide open and expose the nozzles such that the dispensable substance is delivered out of the nozzles in the form of a jet. This can result in trans-epithelial and/or epithelial delivery of the therapeutic agent contained in the dispensable substance.

In some embodiments, as depicted in a partial rendering of an ingestible device in FIGS. 54A and 54B, an ingestible device 5400 includes an inflated membrane volume 5460, e.g., a gas balloon or similar, located within the volume 5410 including a dispensable substance and arranged to seal the nozzle openings 5402 while the inflated volume 5460 is inflated. In some embodiments, the inflated membrane volume 5460 may conform to one or more contours, e.g., an inner curvature, of the ingestible device housing 5404. The inflated membrane volume 5460 can be composed of a balloon and/or soft material, e.g., a low durometer elastomer. When the device 5400 is swallowed by the subject, the enteric trigger prevents the dispensable substance in the fluid volume from being under pressure by holding the spring and the piercer in place. When the device reaches the appropriate location in the GI tract, the enteric trigger degrades and/or dissolves (e.g., due to pH, change in pH, presence of certain enzyme, and/or concentration of certain enzyme) such that the spring forces the piercer into the gas cylinder, puncturing the gas cylinder and causing gas at elevated pressure to leave the cylinder. This causes the gas cylinder to press against the piston and apply pressure to the fluid volume. The pressurized fluid volume applies pressure to the inflated membrane volume 5460 and causes the inflated membrane volume to deflate or otherwise reposition to expose the nozzles openings 5402 such that the dispensable substance is delivered out of the nozzles in the form of a jet. This can result in trans-epithelial and/or epithelial delivery of the therapeutic agent contained in the dispensable substance.

In some embodiments, as depicted in a partial rendering of an ingestible device in FIG. 55, the ingestible device 5500 does not include a covering member. For example, the nozzle openings 5502 may be exposed such that when the ingestible device 5500 is swallowed/inserted, an air gap in the nozzle openings 5502 and/or surface tension effects may prevent or deter gastric media from damaging the internal components or dispensable substance (e.g., drug-containing liquid) within the ingestible device. In other words, a differential force may be generated by the movement of the ingestible device within the gastric region between external intestinal forces/pressure and internal forces of the dispensable substance within the volume of the ingestible device. For example, a surface tension of the dispensable substance within a volume 5510 of the ingestible device can be higher than a surrounding environment, e.g., external intestinal forces/pressure within a gastric region in the body, such that a substantial percentage of the dispensable substance is retained within the volume of the ingestible device until a point of delivery of the dispensable substance, e.g., until piston 5518 applies pressure to the volume 5510 to force the dispensable substance retained within the volume 5510 out of the nozzle opening(s) 5502. In one example, at least 75% of the dispensable substance (e.g., at least 85%, at least 95% of the dispensable substance) is retained within the volume of the ingestible device until a point of delivery of the dispensable substance within a gastric region in the body.

Device for Epithelial Delivery

Generally, epithelial delivery can be achieved at any desired location within the GI tract of a subject. In some embodiments, epithelial delivery is achieved in the small intestine of the subject, such as, for example, in the duodenum, the jejunum and/or the ileum. In certain embodiments, epithelial delivery is achieved in the large intestine of the subject, such as, for example, the cecum or the colon.

In some embodiments, epithelial delivery can be achieved using any one of the ingestible devices described above with respect to epithelial delivery. In such embodiments, the relevant parameters are usually modified accordingly. Typically, this modification involves modifying the values for the relevant parameters. Examples are provided in the following paragraphs.

In general, an ingestible device for epithelial delivery is configured to deliver a jet of the dispensable substance having a minimum jet velocity of from at least about 2 m/s (e.g., at least about 3 m/s, at least about 4 m/s, at least about 5 m/s) and/or at most about 20 m/s (e.g., at most about 15 m/s, at most about 10 m/s, at most about 8 m/s). In some embodiments, an ingestible device for epithelial delivery is configured to deliver a jet of the dispensable substance having a peak jet velocity of from about 2 m/s to about 20 m/s (e.g., from about 3 m/s to about 15 m/s, from about 4 m/s to about 10 m/s, from about 5 m/s to about 8 m/s).

In general, an ingestible device for epithelial delivery contains the dispensable substance at an initial fluid volume of at least about 50 microliters ($\mu$L) (e.g., at least about 100 $\mu$L, at least about 150 $\mu$L, at least about 200 $\mu$L, at least about 250 $\mu$L) and/or at most about 800 $\mu$L (e.g., at most about 700 $\mu$L, at most about 600 $\mu$L, at most about 500 $\mu$L, at most about 400 $\mu$L). In some embodiments, an ingestible device for epithelial delivery contains the dispensable substance at an initial fluid volume of from about 50 $\mu$L to about 800 $\mu$L (e.g., from about 100 $\mu$L to about 600 $\mu$L, from about 200 $\mu$L to about 400 $\mu$L).

Generally, an ingestible device for epithelial delivery is configured to provide a delivered fluid volume of dispensable substance of at least about 50 microliters ($\mu$L) (e.g., at least about 100 $\mu$L, at least about 150 $\mu$L, at least about 200 $\mu$L, at least about 250 $\mu$L) and/or at most about 800 $\mu$L (e.g., at most about 700 $\mu$L, at most about 600 $\mu$L, at most about 500 $\mu$L, at most about 400 $\mu$L). In some embodiments, an ingestible device for epithelial delivery has a fluid volume of dispensable substance of from about 50 $\mu$L to about 800 $\mu$L (e.g., from about 100 $\mu$L to about 600 $\mu$L, from about 200 $\mu$L to about 400 $\mu$L).

In general, an ingestible device for epithelial delivery contains the dispensable substance at a final fluid volume of at most about 100 microliters ($\mu$L) (e.g., at least about 90 $\mu$L, at least about 80 $\mu$L, at least about 70 $\mu$L, at least about 60 $\mu$L) and/or at most least 5 $\mu$L (e.g., at most about 10 $\mu$L, at most about 20 $\mu$L, at most about 30 $\mu$L, at most about 40 $\mu$L). In some embodiments, an ingestible device for epithelial delivery contains the dispensable substance at a fluid volume of from about 30 $\mu$L to about 70 $\mu$L (e.g., from about 40 $\mu$L to about 60 $\mu$L, from about 45 $\mu$L to about 55 $\mu$L).

In general, an ingestible device for epithelial delivery is configured to directly deliver at least about 50% (e.g., at least about 60%, at least about 70%, at least about 80%, at least about 90%, at least about 95%, at least about 97%) of the dispensable substance from the ingestible device to the mucus.

In general, an ingestible device for epithelial delivery is configured to provide a delivered fluid volume per opening for delivery of dispensable substance (e.g., per nozzle) of at least about 20 microliters (μL) (e.g., at least about 25 μL, at least about μL, at least about 50 μL, at least about 75 μL, at least about 100 μL) and/or at most about 800 μL (e.g., at most about 700 μL, at most about 600 μL, at most about 500 μL, at most about 400 μL, at most about 300 μL). In some embodiments, an ingestible device for epithelial delivery is configured to provide a delivered fluid volume per opening for delivery of dispensable substance (e.g., per nozzle) of from about 25 μL to about 400 μL (e.g., from about 25 μL to about 300 μL, from about 100 μL to about 300 μL).

Each nozzle can have a diameter, for example, of at least about 1 mm (e.g., at least about 1.5 mm, at least about 2 mm) and/or at most about 3 mm (e.g., at most about 2.5 mm). For example, in such an ingestible device, each nozzle can have a diameter of from about 1 mm to about 3 mm (e.g., from about 1 mm to about 2.5 mm, from about 2 to about 2.5 mm).

Device for Topical Delivery

Generally, topical delivery can be achieved at any desired location within the GI tract of a subject. In some embodiments, topical delivery is achieved in the small intestine of the subject, such as, for example, in the duodenum, the jejunum and/or the ileum. In certain embodiments, topical delivery is achieved in the large intestine of the subject, such as, for example, the cecum or the colon.

In general, an ingestible device for topical delivery is configured to deliver at least about 50% (e.g., at least about 60%, at least about 70%, at least about 80%, at least about 90%, at least about 95%, at least about 97%) of the dispensable substance from the ingestible device into the lumen of the GI tract.

In general, an ingestible device for topical delivery contains the dispensable substance at an initial fluid volume of at least about 50 microliters (μL) (e.g., at least about 100 μL, at least about 150 μL, at least about 200 μL, at least about 250 μL) and/or at most about 800 μL (e.g., at most about 700 μL, at most about 600 μL, at most about 500 μL, at most about 400 μL). In some embodiments, an ingestible device for topical delivery contains the dispensable substance at an initial fluid volume of from about 50 μL to about 800 μL (e.g., from about 100 μL to about 600 μL, from about 200 μL to about 400 μL).

In general, an ingestible device for topical delivery contains the dispensable substance at a final fluid volume of at most about 100 microliters (μL) (e.g., at least about 90 μL, at least about 80 μL, at least about 70 μL, at least about 60 μL) and/or at most least 5 μL (e.g., at most about 10 μL, at most about 20 μL, at most about 30 μL, at most about 40 μL). In some embodiments, an ingestible device for topical delivery contains the dispensable substance at a fluid volume of from about 30 μL to about 70 μL (e.g., from about 40 μL to about 60 μL, from about 45 μL to about 55 μL).

EXAMPLES

Example 1—Modelling Device Performance

In this Example, modelling was used to determine the performance parameters of an ingestible device for delivering a dispensable substance.

Model

The driving pressure, for a given point in the dose delivery, is related to the delivered liquid volume, and the resulting increase in gas volume, by equations of state for adiabatic expansion. The velocity (e.g., peak jet velocity, average jet velocity, or minimum jet velocity) through the orifice is in turn given by the driving pressure. This is a steady state approximation in which transient effects of fluid acceleration/deceleration are ignored. In other words, the gas expansion is rapid allowing little time for heat transfer/thermal equilibration to the surroundings. Thus, this is treated as an adiabatic (no energy loss).

Device and Fluid Properties

Nozzle diameter=0.35 mm

Nozzle length=2 mm

Number of nozzles=2 or 4

Nozzle throat geometry=circular, sharp-edged orifice (Piston diameter=9.6 mm)

Piston friction=10 N due to one O-ring surrounding the piston

Friction pressure loss=about 20 psig

Dispensable substance (fluid)=100 mg/mL adalimumab formulation

Fluid density=1000 kg/m3

Fluid viscosity=7.5 centiPoise

Ratios of specific heat (air)=1.4

Results—Initial Internal Pressure of 320 psig-2 Nozzles

The following properties were used in the model.

Initial internal pressure=320 psig

Fluid pressure=about 300 psig (peak; initial)

Nozzle pressure=about 300 psig (peak; initial)

Initial dose volume of dispensable substance=450 μL

Initial gas volume=370 μL

With these parameters, the modelling yielded the results shown in Tables 1A-1D (liquid pressure is the same as fluid pressure).

TABLE 1A

| Model No. | Delivered Dose (μL) | Gas Vol. (μL) | Gas Pressure (bar) | Liquid Pressure (bar) | Liquid pressure (psi) | Velocity (m/s) |
|---|---|---|---|---|---|---|
| 1 | 0 | 370 | 22.1 | 20.7 | 300.0 | 36.5 |
| 2 | 50 | 420 | 18.5 | 17.1 | 247.9 | 33.1 |
| 3 | 100 | 470 | 15.8 | 14.4 | 208.9 | 30.3 |
| 4 | 150 | 520 | 13.7 | 12.3 | 178.7 | 28.0 |
| 5 | 200 | 570 | 12.0 | 10.7 | 154.7 | 26.0 |
| 6 | 250 | 620 | 10.7 | 9.3 | 135.3 | 24.3 |
| 7 | 300 | 670 | 9.6 | 8.2 | 119.3 | 22.8 |
| 8 | 350 | 720 | 8.7 | 7.3 | 160.0 | 21.5 |
| 9 | 400 | 770 | 7.9 | 6.5 | 94.7 | 20.3 |

TABLE 1B

| Model No. | Re | Friction Factor | Est. Pressure Drop (Pa) | Est. Pressure Drop (bar) | Difference: P Est. v. P Set (bar) |
|---|---|---|---|---|---|
| 1 | 1.70E+03 | 7.23E−02 | 2.07E+06 | 20.68 | 0.00 |
| 2 | 1.54E+03 | 7.37E−02 | 1.71E+06 | 17.09 | 0.00 |
| 3 | 1.42E+03 | 7.51E−02 | 1.44E+06 | 14.40 | 0.00 |
| 4 | 1.31E+03 | 7.65E−02 | 1.23E+06 | 12.32 | 0.00 |
| 5 | 1.22E+03 | 7.78E−02 | 1.07E+06 | 10.67 | 0.00 |
| 6 | 1.14E+03 | 7.92E−02 | 9.33E+05 | 9.33 | 0.00 |
| 7 | 1.06E+03 | 8.05E−02 | 8.23E+05 | 8.23 | 0.00 |
| 8 | 1.00E+03 | 8.18E−02 | 7.31E+05 | 7.31 | 0.00 |
| 9 | 9.46E+02 | 8.31E−02 | 6.53E+05 | 6.53 | 0.00 |

TABLE 1C

| Model No. | Jet Impact Force (N) | Jet Impact Pressure (psi) | Jet Power (W) |
|---|---|---|---|
| 1 | 0.128 | 192.7 | 2.3 |
| 2 | 0.105 | 158.9 | 1.7 |
| 3 | 0.089 | 133.5 | 1.3 |
| 4 | 0.076 | 113.9 | 1.1 |
| 5 | 0.065 | 98.4 | 0.8 |
| 6 | 0.057 | 85.8 | 0.7 |
| 7 | 0.050 | 75.5 | 0.6 |
| 8 | 0.044 | 66.9 | 0.5 |
| 9 | 0.040 | 59.6 | 0.4 |

TABLE 1D

| Model No. | Flowrate per Orifice (m/s) | Total Flowrate (μL/s) | Time for Delivered Vol (ms) | Time from Start of Dose (ms) |
|---|---|---|---|---|
| 1 | 3.51E−06 | 7014.2 | | 0.0 |
| 2 | 3.18E−06 | 6368.4 | 7.47 | 7.5 |
| 3 | 2.92E−06 | 5838.1 | 8.19 | 15.7 |
| 4 | 2.70E−06 | 5392.7 | 8.90 | 24.6 |
| 5 | 2.51E−06 | 5011.8 | 9.61 | 34.2 |
| 6 | 2.34E−06 | 4681.3 | 10.32 | 44.5 |
| 7 | 2.20E−06 | 4390.9 | 11.02 | 55.5 |
| 8 | 2.07E−06 | 4133.0 | 11.73 | 67.3 |
| 9 | 1.95E−06 | 3901.7 | 12.45 | 79.7 |

The minimum (final) fluid pressure is about 95 psig, and the minimum (final) nozzle pressure is about 95 psig. The delivered volume of dispensable substance is 400 μL, and the final gas volume is 770 μL. The average velocity is 27.0 m/s. The total delivery time is 79.7 ms. The average velocity based on dispense time is 26.1 m/s.

Results—Initial Internal Pressure of 300 psig-2 Nozzles
  The following properties were used in the model.
  Initial internal pressure=300 psig
  Fluid pressure=about 280 psig (peak; initial)
  Nozzle pressure=about 280 psig (peak; initial)
  Initial dose volume of dispensable substance=450 μL
  Initial gas volume=370 μL With these parameters, the modelling yielded the results shown in Tables 2A-2D (liquid pressure is the same as fluid pressure).

TABLE 2A

| Model No. | Delivered Dose (μL) | Gas Vol. (μL) | Gas Pressure (bar) | Liquid Pressure (bar) | Liquid pressure (psi) | Velocity (m/s) |
|---|---|---|---|---|---|---|
| 1 | 0 | 370 | 20.7 | 19.3 | 280.0 | 35.2 |
| 2 | 50 | 420 | 17.3 | 15.9 | 231.2 | 31.9 |
| 3 | 100 | 470 | 14.8 | 13.4 | 194.6 | 29.3 |
| 4 | 150 | 520 | 12.8 | 11.5 | 166.3 | 27.0 |
| 5 | 200 | 570 | 11.3 | 9.9 | 143.8 | 25.1 |
| 6 | 250 | 620 | 10.0 | 8.7 | 125.6 | 23.4 |
| 7 | 300 | 670 | 9.0 | 7.6 | 110.6 | 22.0 |
| 8 | 350 | 720 | 8.1 | 6.8 | 98.1 | 20.6 |
| 9 | 400 | 770 | 7.4 | 6.0 | 87.5 | 19.5 |

TABLE 2B

| Model No. | Re | Friction Factor | Est. Pressure Drop (Pa) | Est. Pressure Drop (bar) | Difference P Est. v. P Set (bar) |
|---|---|---|---|---|---|
| 1 | 1.64E+03 | 7.28E−02 | 1.93E+06 | 19.30 | 0.00 |
| 2 | 1.49E+03 | 7.43E−02 | 1.59E+06 | 15.94 | 0.00 |
| 3 | 1.37E+03 | 7.57E−02 | 1.34E+06 | 13.42 | 0.00 |
| 4 | 1.26E+03 | 7.71E−02 | 1.15E+06 | 11.46 | 0.00 |
| 5 | 1.17E+03 | 7.85E−02 | 9.91E+05 | 9.91 | 0.00 |
| 6 | 1.09E+03 | 7.99E−02 | 8.66E+05 | 8.66 | 0.00 |
| 7 | 1.02E+03 | 8.13E−02 | 7.63E+05 | 7.63 | 0.00 |
| 8 | 9.64E+02 | 8.26E−02 | 6.76E+05 | 6.76 | 0.00 |
| 9 | 9.09E+02 | 8.40E−02 | 6.03E+05 | 6.03 | 0.00 |

TABLE 2C

| Model No. | Jet Impact Force (N) | Jet Impact Pressure (psi) | Jet Power (W) |
|---|---|---|---|
| 1 | 0.119 | 179.7 | 2.10 |
| 2 | 0.098 | 148.0 | 1.57 |
| 3 | 0.082 | 124.2 | 1.21 |
| 4 | 0.070 | 105.9 | 0.95 |
| 5 | 0.061 | 91.3 | 0.76 |
| 6 | 0.053 | 79.6 | 0.62 |
| 7 | 0.046 | 69.9 | 0.51 |
| 8 | 0.041 | 61.8 | 0.42 |
| 9 | 0.037 | 55.0 | 0.36 |

TABLE 2D

| Model No. | Flowrate per Orifice (m/s) | Total Flowrate (μL/s) | Time for Delivered Vol (ms) | Time from Start of Dose (ms) |
|---|---|---|---|---|
| 1 | 3.39E−06 | 6773.1 | | 0.0 |
| 2 | 3.07E−06 | 6146.4 | 7.74 | 7.7 |
| 3 | 2.82E−06 | 5631.4 | 8.49 | 16.2 |
| 4 | 2.60E−06 | 5198.7 | 9.23 | 25.5 |
| 5 | 2.41E−06 | 4828.6 | 9.97 | 35.4 |
| 6 | 2.25E−06 | 4507.1 | 10.71 | 46.1 |
| 7 | 2.11E−06 | 4224.7 | 11.45 | 57.6 |
| 8 | 1.99E−06 | 3973.3 | 12.20 | 69.8 |
| 9 | 1.87E−06 | 3747.9 | 12.95 | 82.8 |

The minimum (final) fluid pressure is about 87.5 psig, and the minimum (final) nozzle pressure is about 87.5 psig. The delivered volume of dispensable substance is 400 μL, and the final gas volume is 770 μL. The average velocity is 26.0 m/s. The total delivery time is 82.8 ms. The average velocity based on dispense time is 25.1 m/s.

Results—Initial Internal Pressure of 270 psig—2 Nozzles
  The following properties were used in the model.
  Initial internal pressure=270 psig
  Fluid pressure=about 250 psig (peak; initial)
  Nozzle pressure=about 250 psig (peak; initial)
  Initial dose volume of dispensable substance=450 μL
  Initial gas volume=370 μL With these parameters, the modelling yielded the results shown in Tables 3A-3D (liquid pressure is the same as fluid pressure).

TABLE 3A

| Model No. | Delivered Dose (μL) | Gas Vol. (μL) | Gas Pressure (bar) | Liquid Pressure (bar) | Liquid pressure (psi) | Velocity (m/s) |
|---|---|---|---|---|---|---|
| 1 | 0 | 370 | 18.6 | 17.2 | 250.0 | 33.2 |

TABLE 3A-continued

| Model No. | Delivered Dose (μL) | Gas Vol. (μL) | Gas Pressure (bar) | Liquid Pressure (bar) | Liquid pressure (psi) | Velocity (m/s) |
|---|---|---|---|---|---|---|
| 2 | 50 | 420 | 15.6 | 14.2 | 206.1 | 30.1 |
| 3 | 100 | 470 | 13.3 | 11.9 | 173.1 | 27.6 |
| 4 | 150 | 520 | 11.6 | 10.2 | 147.6 | 25.4 |
| 5 | 200 | 570 | 10.2 | 8.8 | 127.4 | 23.6 |
| 6 | 250 | 620 | 9.0 | 7.7 | 111.0 | 22.0 |
| 7 | 300 | 670 | 8.1 | 6.7 | 97.5 | 20.6 |
| 8 | 350 | 720 | 7.3 | 5.9 | 86.3 | 19.3 |
| 9 | 400 | 770 | 6.7 | 5.3 | 76.7 | 18.2 |

TABLE 3B

| Model No. | Re | Friction Factor | Est. Pressure Drop (Pa) | Est. Pressure Drop (bar) | Difference P Est. v. P Set (bar) |
|---|---|---|---|---|---|
| 1 | 1.55E+03 | 7.36E−02 | 1.72E+06 | 17.23 | 0.00 |
| 2 | 1.41E+03 | 7.52E−02 | 1.42E+06 | 14.21 | 0.00 |
| 3 | 1.29E+03 | 7.68E−02 | 1.19E+06 | 11.94 | 0.00 |
| 4 | 1.19E+03 | 7.83E−02 | 1.02E+06 | 10.18 | 0.00 |
| 5 | 1.10E+03 | 7.98E−02 | 8.78E+05 | 8.78 | 0.00 |
| 6 | 1.03E+03 | 8.12E−02 | 7.66E+05 | 7.66 | 0.00 |
| 7 | 9.61E+02 | 8.27E−02 | 6.73E+05 | 6.73 | 0.00 |
| 8 | 9.02E+02 | 8.42E−02 | 5.95E+05 | 5.95 | 0.00 |
| 9 | 8.50E+02 | 8.57E−02 | 5.29E+05 | 5.29 | 0.00 |

TABLE 3C

| Model No. | Jet Impact Force (N) | Jet Impact Pressure (psi) | Jet Power (W) |
|---|---|---|---|
| 1 | 0.106 | 160.2 | 1.8 |
| 2 | 0.087 | 131.7 | 1.3 |
| 3 | 0.073 | 110.3 | 1.0 |
| 4 | 0.062 | 93.8 | 0.8 |
| 5 | 0.054 | 80.7 | 0.6 |
| 6 | 0.047 | 70.2 | 0.5 |
| 7 | 0.041 | 61.5 | 0.4 |
| 8 | 0.036 | 54.2 | 0.3 |
| 9 | 0.032 | 48.1 | 0.3 |

TABLE 3D

| Model No. | Flowrate per Orifice (m/s) | Total Flowrate (μL/s) | Time for Delivered Vol (ms) | Time from Start of Dose (ms) |
|---|---|---|---|---|
| 1 | 3.20E−06 | 6394.9 | | 0.0 |
| 2 | 2.90E−06 | 5797.8 | 8.20 | 8.2 |
| 3 | 2.65E−06 | 5306.7 | 9.01 | 17.2 |
| 4 | 2.45E−06 | 4893.8 | 9.80 | 27.0 |
| 5 | 2.27E−06 | 4540.1 | 10.60 | 37.6 |
| 6 | 2.12E−06 | 4232.7 | 11.40 | 49.0 |
| 7 | 1.98E−06 | 3962.1 | 12.20 | 61.2 |
| 8 | 1.86E−06 | 3721.2 | 13.02 | 74.2 |
| 9 | 1.75E−06 | 3504.9 | 13.84 | 88.1 |

The minimum (final) fluid pressure was about 77 psig, and the minimum (final) nozzle pressure was about 77 psig. The delivered volume of dispensable substance was 400 μL, and the final gas volume was 770 μL. The average velocity was 24.5 m/s. The total delivery time was 88.1 ms. The average velocity based on dispense time was 23.6 m/s.

Results—Initial Internal Pressure of 220 psig—2 Nozzles

The following properties were used in the model.
Initial internal pressure=220 psig
Fluid pressure=about 200 psig (peak; initial)
Nozzle pressure=about 200 psig (peak; initial)
Initial dose volume of dispensable substance=450 μL
Initial gas volume=370 μL With these parameters, the modelling yielded the results shown in Tables 4A-4D (liquid pressure is the same as fluid pressure).

TABLE 4A

| Model No. | Delivered Dose (μL) | Gas Vol. (μL) | Gas Pressure (bar) | Liquid Pressure (bar) | Liquid pressure (psi) | Velocity (m/s) |
|---|---|---|---|---|---|---|
| 1 | 0 | 370 | 15.2 | 13.8 | 200.0 | 29.7 |
| 2 | 50 | 420 | 12.7 | 11.3 | 164.2 | 26.8 |
| 3 | 100 | 470 | 10.9 | 9.5 | 137.3 | 24.5 |
| 4 | 150 | 520 | 9.4 | 8.0 | 116.6 | 22.6 |
| 5 | 200 | 570 | 8.3 | 6.9 | 100.1 | 20.9 |
| 6 | 250 | 620 | 7.4 | 6.0 | 86.8 | 19.4 |
| 7 | 300 | 670 | 6.6 | 5.2 | 75.8 | 18.1 |
| 8 | 350 | 720 | 6.0 | 4.6 | 66.6 | 16.9 |
| 9 | 400 | 770 | 5.4 | 4.1 | 58.8 | 15.9 |

TABLE 4B

| Model No. | Re | Friction Factor | Est. Pressure Drop (Pa) | Est. Pressure Drop (bar) | Difference P Est. v. P Set (bar) |
|---|---|---|---|---|---|
| 1 | 1.38E+03 | 7.55E−02 | 1.38E+06 | 13.79 | 0.00 |
| 2 | 1.25E+03 | 7.73E−02 | 1.13E+06 | 11.32 | 0.00 |
| 3 | 1.14E+03 | 7.90E−02 | 9.47E+05 | 9.47 | 0.00 |
| 4 | 1.05E+03 | 8.07E−02 | 8.04E+05 | 8.04 | 0.00 |
| 5 | 9.74E+02 | 8.24E−02 | 6.90E+05 | 6.90 | 0.00 |
| 6 | 9.05E+02 | 8.41E−02 | 5.98E+05 | 5.98 | 0.00 |
| 7 | 8.45E+02 | 8.58E−02 | 5.22E+05 | 5.22 | 0.00 |
| 8 | 7.90E+02 | 8.75E−02 | 4.59E+05 | 4.59 | 0.00 |
| 9 | 7.42E+02 | 8.93E−02 | 4.06E+05 | 4.06 | 0.00 |

TABLE 4C

| Model No. | Jet Impact Force (N) | Jet Impact Pressure (psi) | Jet Power (W) |
|---|---|---|---|
| 1 | 0.085 | 127.7 | 1.3 |
| 2 | 0.069 | 104.5 | 0.9 |
| 3 | 0.058 | 87.2 | 0.7 |
| 4 | 0.049 | 73.8 | 0.6 |
| 5 | 0.042 | 63.1 | 0.4 |
| 6 | 0.036 | 54.6 | 0.4 |
| 7 | 0.032 | 47.5 | 0.3 |
| 8 | 0.028 | 41.6 | 0.2 |
| 9 | 0.024 | 36.6 | 0.2 |

TABLE 4D

| Model No. | Flowrate per Orifice (m/s) | Total Flowrate (μL/s) | Time for Delivered Vol (ms) | Time from Start of Dose (ms) |
|---|---|---|---|---|
| 1 | 2.86E−06 | 5710.0 | | 0.0 |
| 2 | 2.85E−06 | 5165.8 | 9.19 | 9.2 |
| 3 | 2.36E−06 | 4717.3 | 10.12 | 19.3 |
| 4 | 2.17E−06 | 4339.2 | 11.04 | 30.4 |
| 5 | 2.01E−06 | 4014.7 | 11.97 | 42.3 |
| 6 | 1.87E−06 | 3731.9 | 12.91 | 55.2 |
| 7 | 1.74E−06 | 3482.2 | 13.86 | 69.1 |
| 8 | 1.63E−06 | 3259.4 | 14.83 | 83.9 |
| 9 | 1.53E−06 | 3058.5 | 15.83 | 99.8 |

The minimum (final) fluid pressure was about 59 psig, and the minimum (final) nozzle pressure was about 59 psig. The delivered volume of dispensable substance was 400 μL, and the final gas volume was 770 μL. The average velocity was 21.6 m/s. The total delivery time was 99.8 ms. The average velocity based on dispense time was 20.8 m/s.

Results—Initial Internal Pressure of 350 psig-4 Nozzles

The following properties were used in the model.
Initial internal pressure=350 psig
Fluid pressure=about 330 psig (peak; initial)
Nozzle pressure=about 330 psig (peak; initial)
Initial dose volume of dispensable substance=450 μL
Initial gas volume=370 μL With these parameters, the modelling yielded the results shown in Tables 5A-5D (liquid pressure is the same as fluid pressure).

TABLE 5A

| Model No. | Delivered Dose (μL) | Gas Vol. (μL) | Gas Pressure (bar) | Liquid Pressure (bar) | Liquid pressure (psi) | Velocity (m/s) |
| --- | --- | --- | --- | --- | --- | --- |
| 1 | 0 | 370 | 24.1 | 22.8 | 330.0 | 38.3 |
| 2 | 50 | 420 | 20.2 | 18.8 | 273.1 | 34.8 |
| 3 | 100 | 470 | 17.3 | 15.9 | 230.4 | 31.9 |
| 4 | 150 | 520 | 15.0 | 13.6 | 197.3 | 29.5 |
| 5 | 200 | 570 | 13.2 | 11.8 | 171.1 | 27.4 |
| 6 | 250 | 620 | 11.7 | 10.3 | 149.9 | 25.6 |
| 7 | 300 | 670 | 10.5 | 9.1 | 132.4 | 24.1 |
| 8 | 350 | 720 | 9.5 | 8.1 | 117.8 | 22.7 |
| 9 | 400 | 770 | 8.6 | 7.3 | 105.4 | 21.4 |

TABLE 5B

| Model No. | Re | Friction Factor | Est. Pressure Drop (Pa) | Est. Pressure Drop (bar) | Difference P Est. v. P Set (bar) |
| --- | --- | --- | --- | --- | --- |
| 1 | 1.79E+03 | 7.16E−02 | 2.28E+06 | 22.75 | 0.00 |
| 2 | 1.62E+03 | 7.30E−02 | 1.88E+06 | 18.83 | 0.00 |
| 3 | 1.49E+03 | 7.43E−02 | 1.59E+06 | 15.88 | 0.00 |
| 4 | 1.38E+03 | 7.56E−02 | 1.36E+06 | 13.60 | 0.00 |
| 5 | 1.28E+03 | 7.69E−02 | 1.18E+06 | 11.80 | 0.00 |
| 6 | 1.20E+03 | 7.81E−02 | 1.03E+06 | 10.33 | 0.00 |
| 7 | 1.12E+03 | 7.94E−02 | 9.13E+05 | 9.13 | 0.00 |
| 8 | 1.06E+03 | 8.06E−02 | 8.12E+05 | 8.12 | 0.00 |
| 9 | 1.00E+03 | 8.18E−02 | 7.27E+05 | 7.27 | 0.00 |

TABLE 5C

| Model No. | Jet Impact Force (N) | Jet Impact Pressure (psi) | Jet Power (W) |
| --- | --- | --- | --- |
| 1 | 0.141 | 212.3 | 2.7 |
| 2 | 0.116 | 175.2 | 2.0 |
| 3 | 0.098 | 147.4 | 1.6 |
| 4 | 0.084 | 126.0 | 1.2 |
| 5 | 0.072 | 109.0 | 1.0 |
| 6 | 0.063 | 95.3 | 0.8 |
| 7 | 0.056 | 84.0 | 0.7 |
| 8 | 0.049 | 74.5 | 0.6 |
| 9 | 0.044 | 66.6 | 0.5 |

TABLE 5D

| Model No. | Flowrate per Orifice (m/s) | Total Flowrate (μL/s) | Time for Delivered Vol (ms) | Time from Start of Dose (ms) |
| --- | --- | --- | --- | --- |
| 1 | 3.68E−06 | 14722.3 | | 0.0 |
| 2 | 3.34E−06 | 13375.8 | 3.56 | 3.6 |
| 3 | 3.07E−06 | 12270.4 | 3.90 | 7.5 |
| 4 | 2.84E−06 | 11342.7 | 4.23 | 11.7 |
| 5 | 2.64E−06 | 10550.1 | 4.57 | 16.3 |
| 6 | 2.47E−06 | 9862.8 | 4.90 | 21.2 |
| 7 | 2.31E−06 | 9259.3 | 5.23 | 26.4 |
| 8 | 2.18E−06 | 8723.7 | 5.56 | 32.0 |
| 9 | 2.06E−06 | 8244.0 | 5.89 | 37.8 |

The minimum (final) fluid pressure is about 105.4 psig, and the minimum (final) nozzle pressure is about 105.4 psig. The delivered volume of dispensable substance is 400 μL, and the final gas volume is 770 μL. The average velocity is 28.4 m/s. The total delivery time is 37.8 ms. The average velocity based on dispense time is 27.5 m/s.

Results—Initial Internal Pressure of 320 psig-4 Nozzles

The following properties were used in the model.
Initial internal pressure=320 psig
Fluid pressure=about 300 psig (peak; initial)
Nozzle pressure=about 300 psig (peak; initial)
Initial dose volume of dispensable substance=450 μL
Initial gas volume=370 μL With these parameters, the modelling yielded the results shown in Tables 6A-6D (liquid pressure is the same as fluid pressure).

TABLE 6A

| Model No. | Delivered Dose (μL) | Gas Vol. (μL) | Gas Pressure (bar) | Liquid Pressure (bar) | Liquid pressure (psi) | Velocity (m/s) |
| --- | --- | --- | --- | --- | --- | --- |
| 1 | 0 | 370 | 22.1 | 20.7 | 300.0 | 36.5 |
| 2 | 50 | 420 | 18.5 | 17.1 | 247.9 | 33.1 |
| 3 | 100 | 470 | 15.8 | 14.4 | 208.9 | 30.3 |
| 4 | 150 | 520 | 13.7 | 12.3 | 178.7 | 28.0 |
| 5 | 200 | 570 | 12.0 | 10.7 | 154.7 | 26.0 |
| 6 | 250 | 620 | 10.7 | 9.3 | 135.3 | 24.3 |
| 7 | 300 | 670 | 9.6 | 8.2 | 119.3 | 22.8 |
| 8 | 350 | 720 | 8.7 | 7.3 | 106.0 | 21.5 |
| 9 | 400 | 770 | 7.9 | 6.5 | 94.7 | 20.3 |

TABLE 6B

| Model No. | Re | Friction Factor | Est. Pressure Drop (Pa) | Est. Pressure Drop (bar) | Difference P Est. v. P Set (bar) |
| --- | --- | --- | --- | --- | --- |
| 1 | 1.70E+03 | 7.23E−02 | 2.07E+06 | 20.68 | 0.00 |
| 2 | 1.54E+03 | 7.37E−02 | 1.71E+06 | 17.09 | 0.00 |
| 3 | 1.42E+03 | 7.51E−02 | 1.44E+06 | 14.40 | 0.00 |
| 4 | 1.31E+03 | 7.65E−02 | 1.23E+06 | 12.32 | 0.00 |
| 5 | 1.22E+03 | 7.78E−02 | 1.07E+06 | 10.67 | 0.00 |
| 6 | 1.14E+03 | 7.92E−02 | 9.33E+05 | 9.33 | 0.00 |
| 7 | 1.06E+03 | 8.05E−02 | 8.23E+05 | 8.23 | 0.00 |
| 8 | 1.00E+03 | 8.18E−02 | 7.31E+05 | 7.31 | 0.00 |
| 9 | 9.46E+02 | 8.31E−02 | 6.53E+05 | 6.53 | 0.00 |

TABLE 6C

| Model No. | Jet Impact Force (N) | Jet Impact Pressure (psi) | Jet Power (W) |
| --- | --- | --- | --- |
| 1 | 0.128 | 192.7 | 2.3 |

TABLE 6C-continued

| Model No. | Jet Impact Force (N) | Jet Impact Pressure (psi) | Jet Power (W) |
|---|---|---|---|
| 2 | 0.105 | 158.9 | 1.7 |
| 3 | 0.089 | 133.5 | 1.3 |
| 4 | 0.076 | 113.9 | 1.1 |
| 5 | 0.065 | 98.4 | 0.8 |
| 6 | 0.057 | 85.8 | 0.7 |
| 7 | 0.050 | 75.5 | 0.6 |
| 8 | 0.044 | 66.9 | 0.5 |
| 9 | 0.040 | 59.6 | 0.4 |

TABLE 6D

| Model No. | Flowrate per Orifice (m/s) | Total Flowrate (μL/s) | Time for Delivered Vol (ms) | Time from Start of Dose (ms) |
|---|---|---|---|---|
| 1 | 3.51E−06 | 14028.4 |  | 0.0 |
| 2 | 3.18E−06 | 12736.9 | 3.74 | 3.7 |
| 3 | 2.92E−06 | 11676.1 | 4.10 | 7.8 |
| 4 | 2.70E−06 | 10785.3 | 4.45 | 12.3 |
| 5 | 2.51E−06 | 10023.7 | 4.81 | 17.1 |
| 6 | 2.34E−06 | 9362.7 | 5.16 | 22.2 |
| 7 | 2.20E−06 | 8781.9 | 5.51 | 27.8 |
| 8 | 2.07E−06 | 8266.0 | 5.87 | 33.6 |
| 9 | 1.95E−06 | 7803.5 | 6.22 | 39.8 |

The minimum (final) fluid pressure is about 94.7 psig, and the minimum (final) nozzle pressure is about 94.7 psig. The delivered volume of dispensable substance is 400 μL, and the final gas volume is 770 μL. The average velocity is 27.0 m/s. The total delivery time is 39.8 ins. The average velocity based on dispense time is 26.1 m/s.

Results—Summary

A summary of certain data for the ingestible devices with two nozzles is provided in Table 7. The pre-compressed gas pressure (psig) is the initial internal pressure, and liquid pressure is fluid pressure.

TABLE 7

| Drive Force Generator: Pre- compressed gas pressure (psig) | Peak Liquid Pressure (psig) | Peak Jet Velocity (m/s) | Peak Jet Power (W) |
|---|---|---|---|
| 320 | 300 | 36.5 | 2.3 |
| 300 | 280 | 35.2 | 2.1 |
| 270 | 250 | 33.2 | 1.8 |
| 220 | 200 | 29.7 | 1.3 |

A summary of certain data for the ingestible devices with four nozzles is provided in Table 8. "Drive Force Generator: Pre-compressed gas pressure (psig)" was the initial internal pressure, and "liquid pressure" is fluid pressure.

TABLE 8

| Drive Force Generator: Pre- compressed gas pressure (psig) | Peak Liquid Pressure (psig) | Peak Jet Velocity (m/s) | Peak Jet Power (W) |
|---|---|---|---|
| 350 | 330 | 38.3 | 2.7 |
| 320 | 300 | 36.5 | 2.3 |

Example 2—Modelling Device Performance

In this Example, modelling was used to determine the performance parameters of an ingestible device for delivering a dispensable substance. The model was the same as described in Example 1.

Device and Fluid Properties

Number of nozzles=2

Nozzle throat geometry=circular, sharp-edged orifice

Piston diameter=7 mm

Piston friction=3.7 N

Friction pressure loss=14 psig

Dispensable substance (fluid)=Water

Fluid density=1,000 kg/m3

Fluid viscosity=1 centiPoise

Ratios of specific heat (air)=1.4

Initial dose volume of dispensable substance=300 μL

Initial gas volume=400 μL

With these parameters, the modelling yielded the results shown in Table 9 (liquid pressure is the same as fluid pressure).

TABLE 9

| Nozzle Diameter (mm) | Nozzle Length (mm) | Initial Internal Pressure (psig) | Peak Fluid Pressure (psig) | Peak Jet Velocity (m/s) | Peak Jet Force (mN) | Peak Jet Power (W) |
|---|---|---|---|---|---|---|
| 0.35 | 2.0 | 320 | 306 | 47.7 | 231 | 5.5 |
| 0.35 | 0.70 | 320 | 306 | 50.6 | 260 | 6.6 |
| 0.20 | 0.70 | 320 | 306 | 48.4 | 74 | 1.8 |
| 0.10 | 0.70 | 320 | 306 | 43.0 | 15 | 0.31 |
| 0.20 | 0.25 | 320 | 306 | 50.8 | 81 | 2.1 |
| 0.10 | 0.25 | 320 | 306 | 48.4 | 18 | 0.44 |
| 0.20 | 0.70 | 20 | 6 | 6.7 | 1.4 | 0.0048 |
| 0.10 | 0.70 | 20 | 6 | 6 | 0.27 | 0.0008 |
| 0.20 | 0.25 | 20 | 6 | 7.1 | 1.6 | 0.0057 |
| 0.10 | 0.25 | 20 | 6 | 7 | 0.35 | 0.0012 |
| 0.20 | 0.70 | 660 | 646 | 70.4 | 156 | 5.5 |
| 0.10 | 0.70 | 2070 | 2056 | 111.9 | 98 | 5.5 |
| 0.20 | 0.25 | 600 | 586 | 70.4 | 156 | 5.5 |
| 0.10 | 0.25 | 1650 | 1636 | 112.0 | 98 | 5.5 |
| 0.10 | 0.25 | 34 | 20 | 12.3 | 1.2 | 0.007 |
| 0.10 | 0.25 | 320 | 306 | 48.4 | 18.4 | 0.44 |
| 0.10 | 0.25 | 175 | 161 | 35.0 | 9.6 | 0.17 |

Example 3—Jet Measurements

High-speed video was used to measure parameters for jets of a dispensable substance (water) delivered from devices having different nozzle diameters and nozzle lengths. The parameters for the devices were as listed above in Example 2. The receiving medium (external environment) was air with gelatin (4% gelatin solution) located 5 mm from the nozzle exit. The nozzles were made of machined aluminum. The nozzle shape was a circular, sharp edged orifice.

The results are shown in the last two columns of Table 9. The first eight columns of Table 9 provide data for the nozzles based on modelling (see Example 2 and Table 9 above).

TABLE 10

| Nozzle Diameter (mm) | Nozzle Length (mm) | Initial Internal Pressure (psig) | Peak Fluid Pressure (psig) | Peak Jet Velocity (m/s) | Peak Jet Force (mN) | Peak Jet Power (W) | Dose Delivery Time (ms) | Test Peak Jet Force (mN) | Test Dose Delivery Time (ms) |
|---|---|---|---|---|---|---|---|---|---|
| 0.35 | 2.0 | 320 | 306 | 47.7 | 231 | 5.5 | 57 | 184 | 62 |
| 0.35 | 0.70 | 320 | 306 | 50.6 | 260 | 6.6 | 53 | 228 | 51 |
| 0.10 | 0.25 | 34 | 20 | 12.3 | 1.2 | 0.0007 | 3060 | 8 | 3600 |
| 0.10 | 0.25 | 320 | 306 | 48.4 | 18.4 | 0.44 | 725 | 15 | 600 |
| 0.10 | 0.25 | 175 | 161 | 35.0 | 9.6 | 0.17 | 1022 | 12 | 830 |

The experimental peak force values show some agreement with the experimental peak force values from modelling. The experimental dose delivery times also show good correlation with the dose delivery times from modelling.

The ability of the nozzles in Table 10 to deliver the dispensable substance into the gelatin was also investigated. At a gas pressure of 320 PSIG, the power of the high-speed liquid jet and its ability to penetrate the gelatin was significantly reduced for the 0.1 mm diameter nozzles compared to the 0.35 mm diameter nozzle. Decreasing the gas pressure below 320 PSIG further reduced the power of the jet and extended the dose delivery time. For the nozzle with a diameter of 0.1 mm and a length of 0.25, there was no penetration into the gelatin for a gas pressure of 34 PSIG.

From Examples 2 and 3, it appears that peak jet power is a particularly significant parameter in determining whether an ingestible device will be able to provide trans-epithelial delivery of a dispensable substance. For example, with the relatively smaller nozzle diameters but relatively high peak jet velocity, a relatively high peak jet force could be achieved, but the peak jet power could be insufficient to achieve trans-epithelial delivery of a dispensable substance. It is believed that it is the combination of both high peak jet pressure and a relatively large nozzle diameter (with a corresponding relatively large jet diameter) are involved in successfully providing trans-epithelial delivery.

A number of embodiments have been described. Nevertheless, various modifications may be made without departing from the spirit and scope of the disclosure. Accordingly, other embodiments are within the scope of the following claims.

The invention claimed is:

1. An ingestible device, comprising:
   a volume of liquid in a housing;
   at least one nozzle extending through the housing, the nozzle having an opening of 0.1 to 0.5 mm;
   a drive force generator in the housing for exerting a drive force on a piston in the housing, the piston between the drive force generator and the nozzle;
   the drive force generator, when actuated, exerting a drive force on the piston resulting in:
      a peak fluid pressure of about 100 psig to about 2056 psig; and
      a peak jet power of about 1 to about 6.6 Watts.

2. The ingestible device of claim 1 wherein the nozzle has a length of 0.25 to 2.0 mm.

3. The ingestible device of claim 1 wherein the drive force results in a peak jet velocity of 35 to 112 m/s.

4. The ingestible device of claim 1 wherein the drive force results in a peak jet force of 18 to 260 mN.

5. The ingestible device of claim 1 wherein the drive force generator comprises a compressed gas, the compressed gas, when released, acting on the piston to provide a jet of the liquid out of the nozzle.

6. The ingestible device of claim 1 wherein the nozzle is circular with a sharp-edged orifice.

7. The ingestible device of claim 1 further including a restraining mechanism having a first state in which the restraining mechanism prevents the liquid from being delivered out of the ingestible device; and a second state in which the restraining mechanism does not prevent the liquid from being delivered out of the ingestible device.

8. The ingestible device of claim 7 wherein the restraining mechanism comprises a material selected from the group consisting of an enteric material; a degradable material, an erodible material and a dissolvable material.

9. The ingestible device of claim 7 wherein the restraining mechanism comprises at least one member selected from the group consisting of a seal, a pin, a band, a dowel, a clasp, a clamp, a flange, and a rivet.

10. The ingestible device of claim 7 wherein the drive force generator comprises a gas container holding compressed gas and a spring acting on a piercing element, the piercing element restrained by the restraining mechanism until the ingestible device is actuated, the piercing element then piercing the gas container, allowing the compressed gas to flow out of the gas container and act on the piston, when the drive force generator is actuated.

11. The ingestible device of claim 10 wherein the compressed gas has an initial gas pressure in the gas container of about 500 to about 1200 psig.

12. The ingestible device of claim 10 wherein the gas is released into the housing and the piston slides against interior cylindrical walls of the housing.

13. The ingestible device of claim 1 wherein the nozzle is directed perpendicular to a longitudinal axis of the ingestible device.

14. An ingestible device, comprising:
   liquid in a housing;
   at least one nozzle in the housing, the nozzle having an opening of 0.1 to 0.5 mm;
   a compressed gas contained in the housing;
   a restraining mechanism adapted to release the compressed gas when the ingestible device is actuated, the compressed gas, when released, exerting drive force on the liquid to create a peak fluid pressure on the liquid of 100 psig to 450 psig, and a jet of the liquid out of the nozzle having a peak jet power of 1 to 6.6 Watts.

15. The ingestible device of claim 14 wherein the nozzle has an opening diameter of 0.1 to 0.3 mm.

16. The ingestible device of claim 14 wherein the liquid provides a dose with a delivery time of 38 to 600 ms.

17. The ingestible device of claim 14 wherein the peak jet power is 2.1 to 6.6 Watts.

18. The ingestible device of claim 14 wherein the drive force results in a peak jet velocity of 35 to 112 m/s.

19. The ingestible device of claim 14 wherein the drive force results in a peak jet force of 18 to 260 mN.

20. An ingestible device, comprising:
liquid in a housing;
the housing having at least one nozzle, the nozzle having an opening of 0.1 to 0.35 mm, and a nozzle length of 0.25 to 2.0 mm;
a compressed gas container in the housing, the compressed gas container containing compressed gas;
a restraining mechanism adapted to release the compressed gas when the ingestible device is actuated, the compressed gas, when released, exerting force on the liquid to create a peak fluid pressure on the liquid of 100 psig to 450 psig, a jet of the liquid out of the nozzle having a peak jet power of 1 to 6.6 Watts, and a peak jet force of 90 to 260 mN.

* * * * *